(12) United States Patent
Kim et al.

(10) Patent No.: US 12,325,693 B2
(45) Date of Patent: Jun. 10, 2025

(54) FERROELECTRIC FLUORESCENT SELF-ASSEMBLY COMPOUND AND ORGANIC ELECTRONIC ELEMENT INCLUDING THE SAME

(71) Applicant: INDUSTRY-ACADEMIC COOPERATION FOUNDATION, YONSEI UNIVERSITY, Seoul (KR)

(72) Inventors: Eunkyoung Kim, Seoul (KR); Jinbo Kim, Seoul (KR); Donghwan Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1117 days.

(21) Appl. No.: 17/107,669

(22) Filed: Nov. 30, 2020

(65) Prior Publication Data

US 2022/0009908 A1 Jan. 13, 2022

(30) Foreign Application Priority Data

Jul. 9, 2020 (KR) ........................ 10-2020-0084748

(51) Int. Cl.
*C07D 277/66* (2006.01)
*C07C 43/215* (2006.01)
(Continued)

(52) U.S. Cl.
CPC .......... *C07D 277/66* (2013.01); *C07C 43/215* (2013.01); *C07C 217/92* (2013.01); *C07D 209/86* (2013.01); *C07D 235/12* (2013.01); *C07D 251/24* (2013.01); *C07D 403/10* (2013.01); *C07D 403/12* (2013.01); *C07D 495/14* (2013.01); *H10K 50/868* (2023.02);
(Continued)

(58) Field of Classification Search
CPC ............... H10K 85/631; H10K 85/654; H10K 85/6572; H10K 85/6576; H10K 50/15; H10K 50/18; H10K 50/816; H10K 50/818; C07D 403/10; C07D 209/86; C07D 251/24; C07D 403/12; C07D 495/14; C07C 217/92
See application file for complete search history.

(56) References Cited

U.S. PATENT DOCUMENTS

2016/0181563 A1* 6/2016 Cho ........................ H10K 50/13
257/40

FOREIGN PATENT DOCUMENTS

CN 105339363 B * 3/2018 ........... C07D 251/24
CN 107502344 B 7/2019
(Continued)

OTHER PUBLICATIONS

Pradhan et al. J. Mater. Chem. C, 2016, 4, 6117. (Year: 2016).*
(Continued)

*Primary Examiner* — Joseph K McKane
*Assistant Examiner* — Ashli Ariana Chicks
(74) *Attorney, Agent, or Firm* — McCoy Russell LLP

(57) ABSTRACT

Provided are a ferroelectric fluorescent self-assembly compound and an organic electronic element including the same. The organic electronic element of the present invention includes the ferroelectric fluorescent self-assembly compound to which a specific skeleton and a specific function group are introduced, thereby having excellent light-emitting property, ferroelectricity, and piezoelectricity.

11 Claims, 1 Drawing Sheet

(51) Int. Cl.

| | |
|---|---|
| *C07C 217/92* | (2006.01) |
| *C07D 209/86* | (2006.01) |
| *C07D 235/12* | (2006.01) |
| *C07D 251/24* | (2006.01) |
| *C07D 403/10* | (2006.01) |
| *C07D 403/12* | (2006.01) |
| *C07D 495/14* | (2006.01) |
| *H10K 50/15* | (2023.01) |
| *H10K 50/18* | (2023.01) |
| *H10K 50/80* | (2023.01) |
| *H10K 85/60* | (2023.01) |
| *H10K 50/816* | (2023.01) |
| *H10K 50/818* | (2023.01) |

(52) U.S. Cl.
CPC ......... *H10K 85/631* (2023.02); *H10K 85/654* (2023.02); *H10K 85/6572* (2023.02); *H10K 85/6576* (2023.02); *H10K 50/15* (2023.02); *H10K 50/18* (2023.02); *H10K 50/181* (2023.02); *H10K 50/816* (2023.02); *H10K 50/818* (2023.02)

(56) References Cited

FOREIGN PATENT DOCUMENTS

| | | | |
|---|---|---|---|
| CN | 107188801 B | | 5/2020 |
| JP | 11260551 A | * | 9/1999 |
| KR | 20030021674 A | | 3/2003 |
| KR | 20110015454 A | | 2/2011 |
| KR | 20150143161 A | | 12/2015 |
| KR | 20190132130 A | | 11/2019 |

OTHER PUBLICATIONS

Anetai et al. J. Phys. Chem. Lett. 2015, 6, 1813-1818. (Year: 2015).*

Ekbote et al. J. Mater. Chem. C, 2018,6, 2077-2087. (Year: 2018).*

Qian, C. et al., "Luminescent organogels based on triphenylamine functionalized B-diketones and their difluoroboron complexes," Organic & Biomolecular Chemistry, vol. 13, No. 10, Jan. 8, 2015, 13 pages.

Pradhan, B. et al., "Star-shaped fluorescent liquid crystals derived from s-triazine and 1,3,4-oxadiazole moieties," Journal of Materials Chemistry C, vol. 4, No. 25, May 27, 2016, 15 pages.

* cited by examiner

FERROELECTRIC FLUORESCENT SELF-ASSEMBLY COMPOUND AND ORGANIC ELECTRONIC ELEMENT INCLUDING THE SAME

CROSS-REFERENCE TO RELATED APPLICATIONS

The present application claims priority to Korean Patent Application No. 10-2020-0084748, entitled "FERROELECTRIC LUMINESCENT SELF-ASSEMBLY COMPOUND AND ORGANIC ELECTRONIC DEVICE COMPRISING THE SAME", and filed on Jul. 9, 2020. The entire contents of the above-listed application is hereby incorporated by reference for all purposes.

TECHNICAL FIELD

The following disclosure relates to a ferroelectric fluorescent self-assembly compound and an organic electronic element including the same, and more particularly, to a ferroelectric fluorescent self-assembly compound having an excellent light-emitting property and ferroelectricity, an organic electronic element including the same, and an electronic device including the organic electronic element of the present invention.

BACKGROUND

Usually, ferroelectricity means a phenomenon in which insulators or dielectrics spontaneously have polarization without an external electric field. As ferroelectrics having ferroelectricity, metal oxides are mainly utilized, and $BaTiO_3$ corresponds to the most representative material.

The ferroelectrics have a change in a polarization value depending on an external electric field in the form of a hysteresis curve. That is, as the external electric field is increased, a domain such as an external electric field is increased to increase the polarization value. At a certain electric field or more, the polarization value is saturated, and thereafter, when the electric field is decreased, the polarization value is not 0 and has a constant polarization value. In order for the polarization value to be 0, the electric field should be further decreased.

The ferroelectrics which have a nature of changing a direction when a direction of the external electric field is changed, may be applied for various uses. Since ferroelectrics exhibit a piezoelectric effect to generate electricity when pressure is applied, it is used in daily life such as in piezoelectric fiber, a film sicker, and an initiator of a lighter or a gas stove. In particular, since the ferroelectrics have a large electric capacity and a small size, they are often used in an electronic circuit, and as an example, a multilayer ceramic capacitor (MLCC) adopts an electronic circuit in which a ceramic as dielectrics and a conductive layer are alternately stacked.

In addition, recently, many studies on applying the ferroelectrics to a memory unit have been conducted. A conventional semiconductor-based dynamic random access memory (DRAM) used common dielectrics, but a ferroelectric RAM (FeRAM) is DRAM having ferroelectrics therein instead of common dielectrics so that memory does not disappear even in the case in which the power is off.

Meanwhile, fluorescence refers to an emitted light or an emission phenomenon, when a material absorbing energy is transferred from an excited electronic state to an electronic state having lower energy. Fluorescence has been widely used for detection and analysis of a material in various science fields due to high sensitivity. In recent years, in particular, fluorescence microscopy which allows a fluorescence image of a sample to be obtained is being utilized in the field of life science, together with development of various fluorescent bodies.

However, a conventional fluorescent material exhibits luminescence, but lacks ferroelectricity or piezoelectricity, thereby having a limitation of not having a synesthesia characteristic. In order to overcome the limitation, a technology of using a mixture of a fluorescent material and ferroelectrics has been developed, but the fluorescent material and the ferroelectric material are not uniformly dispersed, or ferroelectricity and piezoelectricity are not sufficiently exhibited.

In addition, a study for self-assembling ferroelectrics for increasing ferroelectricity is being progressed, but in this case, a fluorescent property was deteriorated due to a quenching effect.

Accordingly, development of a material having both ferroelectricity and a fluorescent property is demanded.

RELATED ART DOCUMENTS

Patent Documents

Korean Patent Laid-Open Publication No. 2019-0132130 (Nov. 27, 2019)

SUMMARY

An embodiment of the present invention is directed to providing a ferroelectric fluorescent self-assembly compound having improved luminescence, ferroelectricity, and piezoelectricity by introducing a specific skeleton and a specific substituent.

Another embodiment of the present invention is directed to providing an organic electronic element having all of improved light-emitting property, ferroelectricity, and piezoelectricity.

The present invention provides a ferroelectric fluorescent self-assembly compound which is useful in various organic electronic elements and has excellent luminescence, ferroelectricity, and piezoelectricity.

In one general aspect, a ferroelectric fluorescent self-assembly compound to which a functional group capable of self-assembly is introduced is provided.

Preferably, the ferroelectric fluorescent self-assembly compound of the present invention may be represented by the following Chemical Formula 1:

[Chemical Formula 1]

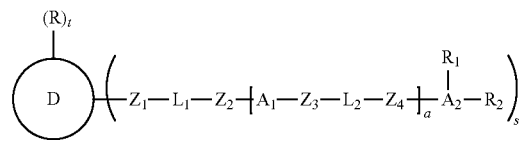

wherein

R is a halogen, CHO, or (C1-C30)alkoxy;

D is selected from the following structures as a main skeleton:

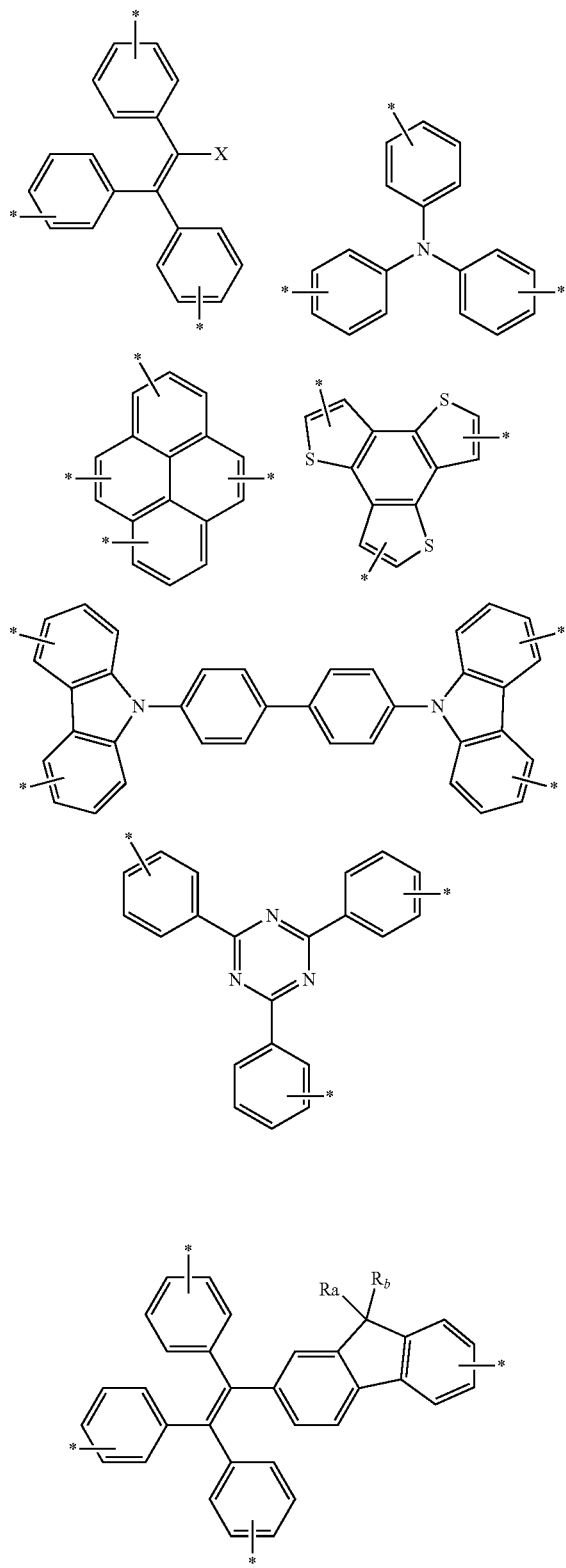

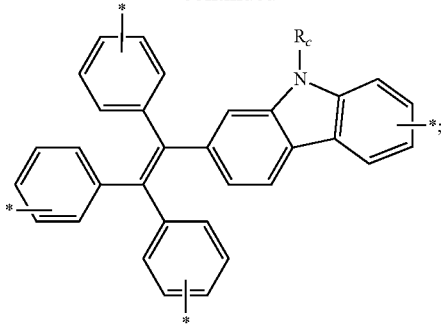

X is a halogen or

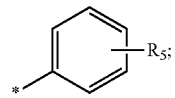

$R_a$, $R_b$, and $R_c$ are independently of one another (C1-C30) alkyl;

$Z_1$ to $Z_4$ are independently of one another a single bond, —O—, —CO—, —OCO—, —COO—, —NH—, —CONH—, —NHCO—, or C2-C30 alkenylene;

$L_1$ and $L_2$ are independently of each other a single bond, C1-C30 alkylene, C2-C30 alkenylene, or C6-C30 arylene;

$A_1$ is independently of each other C1-C30 alkylene, C6-C30 arylene, C1-C30 alkyl C6-C30 arylene or C3-C30 heteroarylene;

$A_2$ and $A_{11}$ are independently of each other a trivalent C1-C30 alkyl radical, a trivalent C6-C30 aryl radical, or a trivalent C6-C30 aryl radical or a trivalent C3-C30 heteroaryl radical substituted with C1-C30 alkyl;

a is an integer of 0 or 2;

$R_1$, $R_2$, and $R_5$ are independently of one another hydrogen, a halogen, C1-C30 alkoxy,

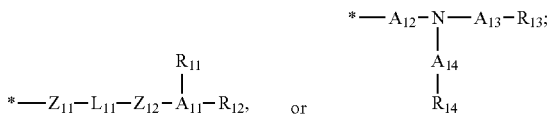

$Z_{11}$ and $Z_{12}$ are independently of each other a single bond, —O—, —OCO—, —COO—, —NH—, —CONH—, —NHCO—, or C2-C20 alkenylene;

$L_{11}$ is a single bond, C1-C30 alkylene, C2-C30 alkenylene, or C6-C30 arylene;

$A_{12}$ to $A_{14}$ are independently of one another C1-C30 alkylene, C6-C30 arylene, or C6-C30 arylene or C3-C30 heteroarylene substituted with C1-C30 alkyl;

$R_{11}$ to $R_{14}$ are independently of one another hydrogen, halogen, C1-C30 alkoxy, CHO, OH, or NHCOOH;

s is an integer of 1 to 4;

t is an integer of 0 to 3; and s+t≤an integer representing the number of substituent sites possessed by the main skeleton D is satisfied.

Preferably, Chemical Formula 1 according to an exemplary embodiment of the present invention may be represented by the following Chemical Formulae 2 to 9:

[Chemical Formula 2]
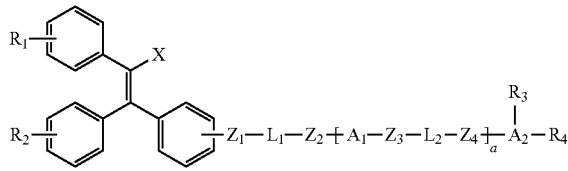
[Chemical Formula 3]
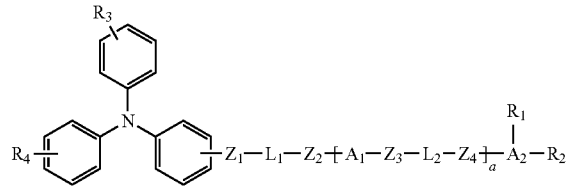
[Chemical Formula 4]
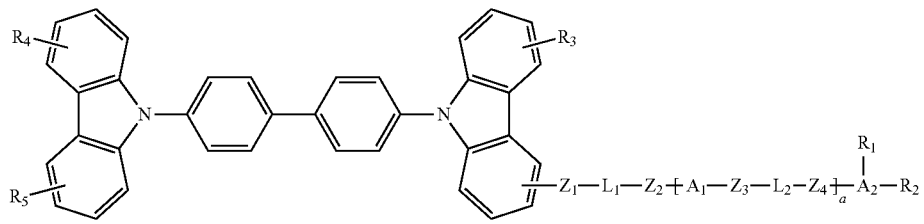
[Chemical Formula 5]
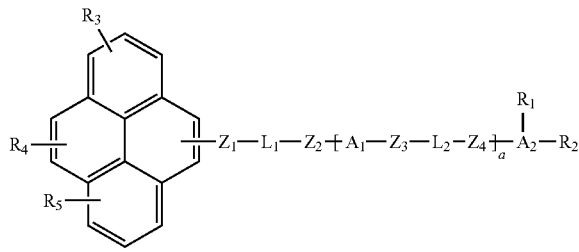
[Chemical Formula 6]
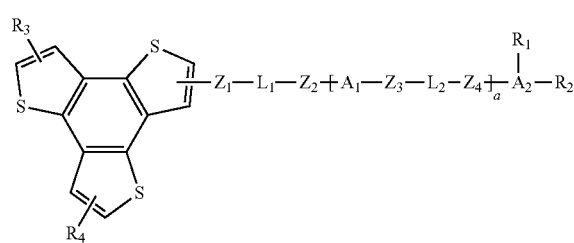
[Chemical Formula 7]
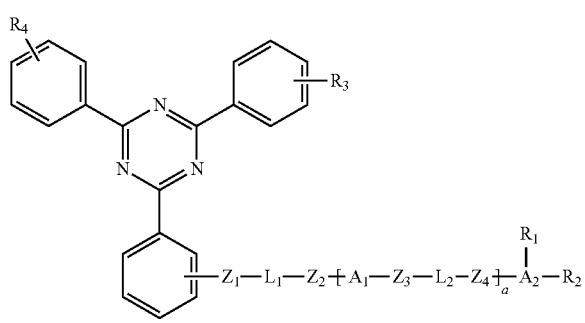
[Chemical Formula 8]
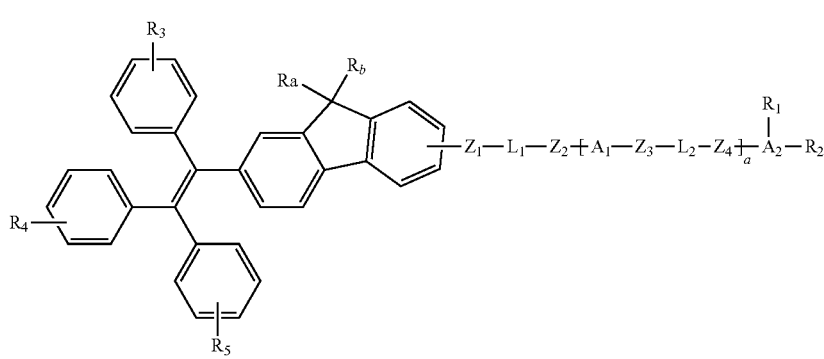

-continued

[Chemical Formula 9]

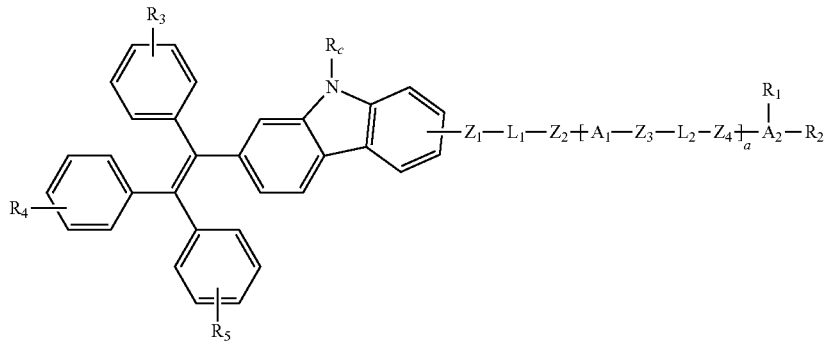

wherein

X is a halogen or

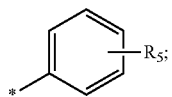

$Z_1$ to $Z_4$ are independently of one another a single bond, —O—, —CO—, —OCO—, —COO—, —NH—, —CONH—, —NHCO—, or C2-C30 alkenylene;

$L_1$ and $L_2$ are independently of each other a single bond, C1-C30 alkylene, C2-C30 alkenylene, or C6-C30 arylene;

$A_1$ is C1-C30 alkylene, C6-C30 arylene, C1-C30 alkyl C6-C30 arylene or C3-C30 heteroarylene;

$A_2$ and $A_{11}$ are independently of each other a trivalent C1-C30 alkyl radical, a trivalent C6-C30 aryl radical, or a trivalent C6-C30 aryl radical or a trivalent C3-C30 heteroaryl radical substituted with C1-C30 alkyl;

a is an integer of 0 or 2;

$R_a$, $R_b$, and $R_c$ are independently of one another (C1-C30) alkyl;

$R_1$ and $R_2$ are independently of each other hydrogen, a halogen, C1-C30 alkoxy,

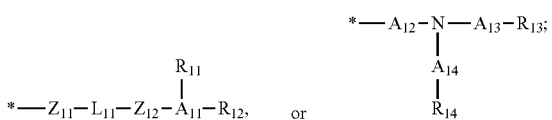

$R_3$ to $R_5$ are independently of one another hydrogen, halogen, C1-C30 alkoxy,

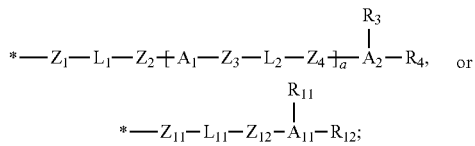

$Z_{11}$ and $Z_{12}$ are independently of each other a single bond, —O—, —OCO—, —COO—, —NH—, —CONH—, —NHCO—, or C2-C20 alkenylene;

$L_{11}$ is a single bond, C1-C30 alkylene, C2-C30 alkenylene, or C6-C30 arylene;

$A_{11}$ to $A_{14}$ are independently of one another C1-C30 alkylene, C6-C30 arylene, or C3-C30 heteroarylene; and $R_{11}$ to $R_{14}$ are independently of one another hydrogen, halogen, C1-C30 alkoxy, CHO, OH, or NHCOOH.

More preferably, in Chemical Formulae 2 to 9 according to an exemplary embodiment of the present invention, X may be a halogen or

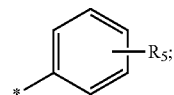

$Z_1$ to $Z_4$ may be independently of one another a single bond, —O—, —CO—, —OCO—, —NH—, —CONH—, or C2-C6 alkenylene;

$L_1$ and $L_2$ may be independently of each other a single bond, C1-C10 alkylene, C2-C10 alkenylene, or C6-C12 arylene;

$A_1$ may be C1-C20 alkylene, C6-C20 arylene, C1-C20 alkyl C6-C20 arylene, or C3-C20 heteroarylene;

$A_2$ and $A_{11}$ may be independently of each other a trivalent C1-C20 alkyl radical, a trivalent C6-C20 aryl radical, or a trivalent C6-C20 aryl radical or a trivalent C3-C20 heteroaryl radical substituted with C1-C20 alkyl;

a may be an integer of 0 or 1;

$R_a$, $R_b$, and $R_c$ may be independently of one another (C1-C20)alkyl;

$R_1$, $R_2$, and $R_5$ may be independently of one another hydrogen, a halogen, C1-C30 alkoxy,

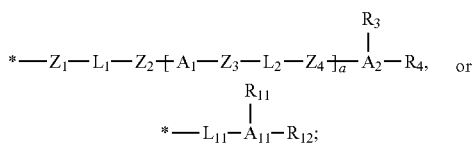

$R_3$ and $R_4$ may be independently of each other hydrogen, a halogen, C1-C30 alkoxy,

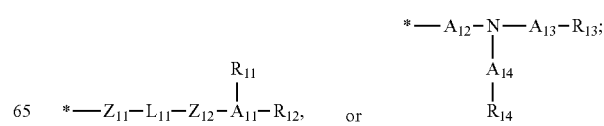

$Z_{11}$ and $Z_{12}$ may be independently of each other a single bond, —O—, —OCO—, —NH—, —CONH—, or C2-C6 alkenylene;

$L_{11}$ may be a single bond, C1-C10 alkylene, C2-C10 alkenylene, or C6-C12 arylene;

$A_{12}$ to $A_{14}$ may be independently of one another C1-C20 alkylene, C6-C20 arylene, or C3-C20 heteroarylene; and $R_{11}$ to $R_{14}$ may be independently of one another hydrogen, a halogen, C4-C25 alkoxy, CHO, or NHCOOH.

More preferably, in Chemical Formulae 2 to 9 according to an exemplary embodiment of the present invention, X may be a halogen or

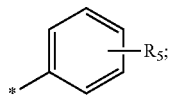

$Z_1$ and $Z_3$ may be independently of each other a single bond, —O—, —CO—, —OCO—, —NH—, or —CONH—;

$Z_2$ and $Z_4$ may be independently of each other a single bond, —O— or C2-C6 alkenylene;

$L_1$ and $L_2$ may be independently of each other a single bond, C1-C10 alkylene, C2-C10 alkenylene, or C6-C12 arylene;

$A_1$ may be C1-C6 alkylene, C6-C12 arylene, C1-C20 alkyl C6-C20 arylene or C3-C12 heteroarylene;

$A_2$ may be a trivalent C1-05 alkyl radical, a trivalent C6-C12 aryl radical, or a trivalent C6-C12 aryl radical or a trivalent C3-C12heteroaryl radical substituted with C1-C12 alkyl;

a may be an integer of 0 or 1;

$R_a$, $R_b$, and $R_c$ may be independently of one another (C1-C20)alkyl;

$R_1$, $R_2$, and $R_5$ may be independently of one another hydrogen, a halogen, C1-C20 alkoxy,

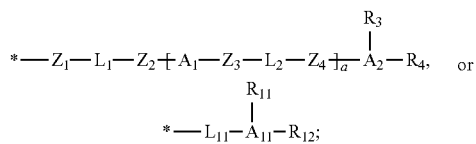

$R_3$ and $R_4$ may be independently of each other hydrogen, a halogen, C4-C25 alkoxy,

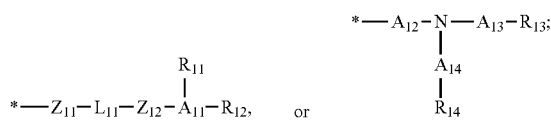

$Z_{11}$ may be a single bond, —O—, —OCO—, —NH—, or —CONH—;

$Z_{12}$ may be a single bond, —O—, or C2-C6 alkenylene;

$L_{11}$ may be a single bond, C1-C10 alkylene, C2-C10 alkenylene, or C6-C12 arylene;

$A_{11}$ may be a trivalent C1-C10 alkyl radical, a trivalent C6-C12 aryl radical, or a trivalent C6-C12 aryl radical or a trivalent C3-C12 heteroaryl radical substituted with C1-C10 alkyl;

$A_{12}$ to $A_{14}$ may be independently of one another C1-C10 alkylene, C6-C12 arylene, or C3-C12 heteroarylene; and $R_{11}$ to $R_{14}$ may be independently of one another hydrogen, a halogen, C4-C25 alkoxy, CHO, or NHCOOH.

In terms of having better optical properties, Chemical Formula 2 according to an exemplary embodiment of the present invention may be represented by the following Chemical Formula 11 or Chemical Formula 12:

[Chemical Formula 11]

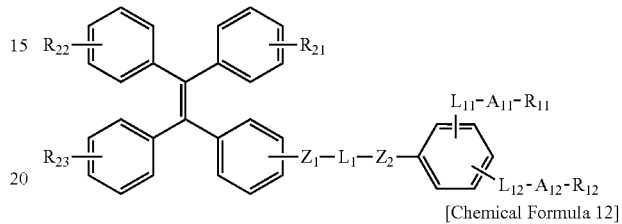

[Chemical Formula 12]

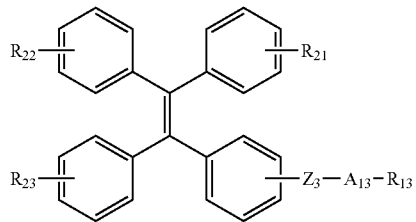

wherein $Z_1$ to $Z_3$ are independently of one another a single bond, —O—, —OCO—, —COO—, —NH—, —CONH—, —NHCO—, C2-C30 alkenylene, or C6-C30 arylene;

$L_1$, $L_{11}$, and $L_{12}$ are independently of one another a single bond, C1-C30 alkylene, C2-C30 alkenylene, or C6-C30 arylene;

$A_{11}$ to $A_{13}$ are independently of one another C1-C30 alkylene, C6-C30 arylene, or C3-C30 heteroarylene;

$R_{11}$ to $R_{13}$ are independently of one another hydrogen, a halogen, C1-C30 alkoxy, or NHCOOH;

$R_{21}$ to $R_{23}$ are independently of one another hydrogen, a halogen, C1-C30 alkoxy,

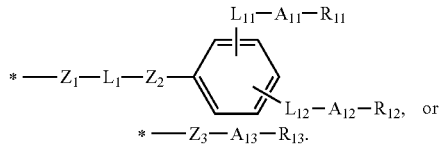

Preferably, in Chemical Formulae 11 and 12 according to an exemplary embodiment of the present invention, $Z_1$ may be a single bond; $Z_2$ may be C2-C20 alkenylene; $Z_3$ may be independently of each other a single bond, —O—, —NH—, —CONH—, or C6-C20 arylene; $L_1$ may be a single bond or C6-C20 arylene; $L_{11}$ and $L_{12}$ may be independently of each other C2-C20 alkenylene; $A_{11}$ to $A_{13}$ may be independently of each other C6-C20 arylene; $A_{13}$ may be C1-C20 alkylene, C6-C20 arylene, or C3-C30 heteroarylene; $R_{11}$ to $R_{13}$ may be independently of each other hydrogen, C4-C30 alkoxy, or NHCOOH; $R_{21}$ to $R_{23}$ may be independently of each other hydrogen, C1-C20 alkoxy,

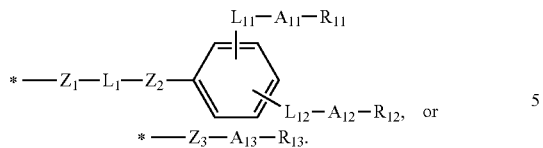

Preferably, the ferroelectric fluorescent self-assembly compound of Chemical Formula 2 according to an exemplary embodiment of the present invention may be represented by the following Chemical Formula 13 or Chemical Formula 14:

[Chemical Formula 13]

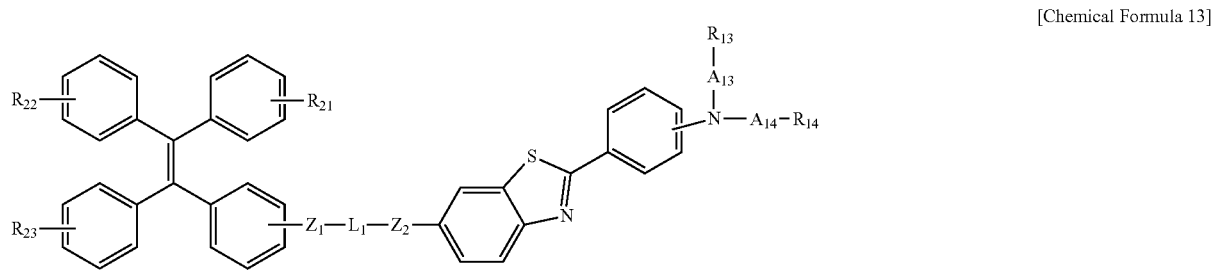

[Chemical Formula 14]

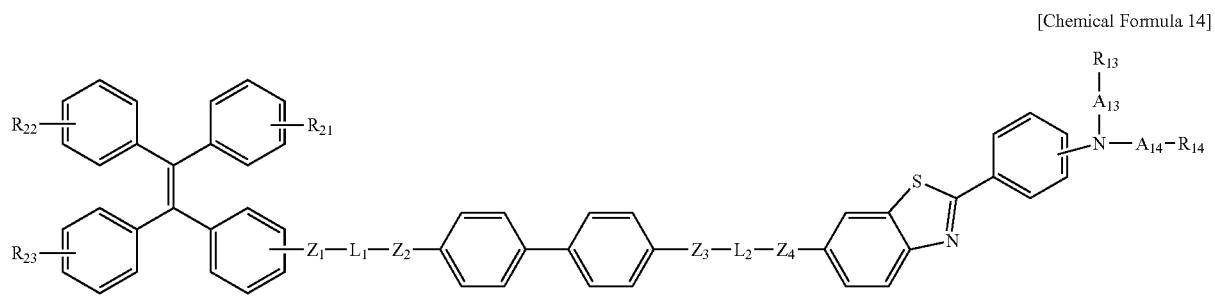

wherein
$Z_1$ to $Z_4$ are independently of one another a single bond, —O—, —OCO—, —COO—, —NH—, —CONH—, —NHCO—, or C2-C30 alkenylene;
$L_1$ and $L_2$ are independently of each other a single bond, C1-C30 alkylene, C2-C30 alkenylene, or C6-C30 arylene;
$A_{13}$ and $A_{14}$ are independently of each other C6-C30 arylene;
$R_{13}$ and $R_{14}$ are independently of each other hydrogen, a halogen, C1-C30 alkoxy, CHO, or NHCOOH; and
$R_{21}$ to $R_{23}$ are independently of one another hydrogen, a halogen, C1-C30 alkoxy, or in which a is an integer of 0 or 1.

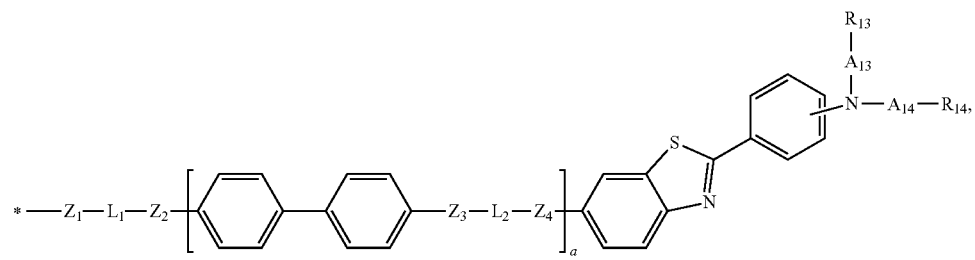

In terms of having better optical properties, preferably, in Chemical Formula 13 and Chemical Formula 14 according to an exemplary embodiment of the present invention, $Z_1$ to $Z_4$ may be independently of one another a single bond, —O—, or —OCO—; $L_1$ and $L_2$ may be independently of each other a single bond or C2-C20 alkenylene; $A_{13}$ and $A_{14}$ may be independently of each other C6-C12 arylene; $R_{13}$ and $R_{14}$ may be independently of each other hydrogen, a halogen, CHO, or NHCOOH; and $R_{21}$ to $R_{23}$ may be independently of one another hydrogen, C1-C30 alkoxy, or in which a may be an integer of 0 or 1.

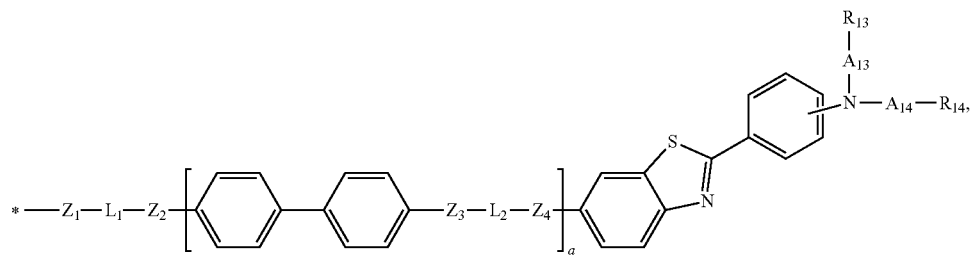

Specifically, the ferroelectric fluorescent self-assembly compound according to an exemplary embodiment of the present invention may be selected from the following compounds, but is not limited thereto:

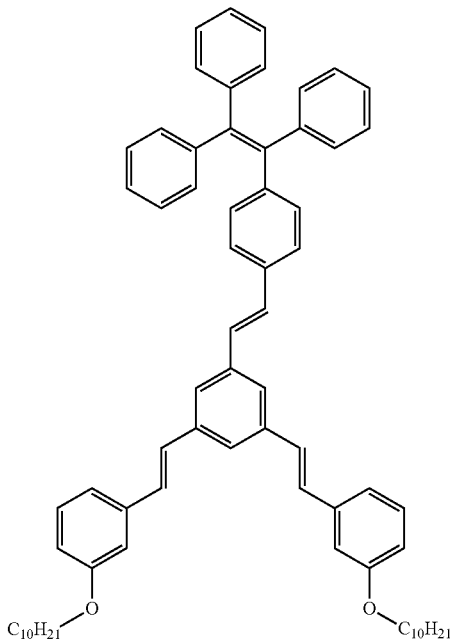

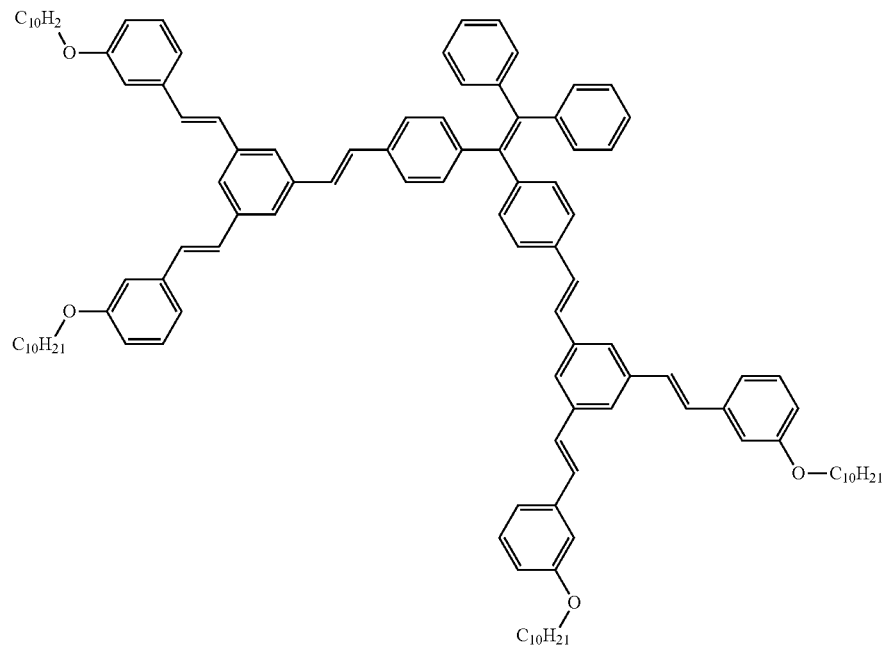
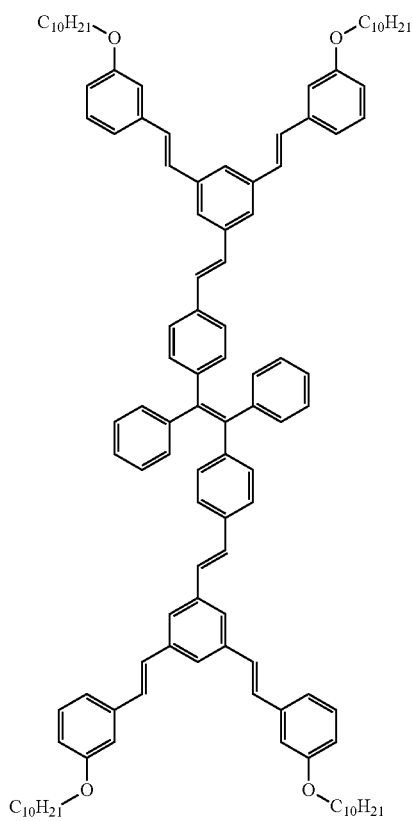
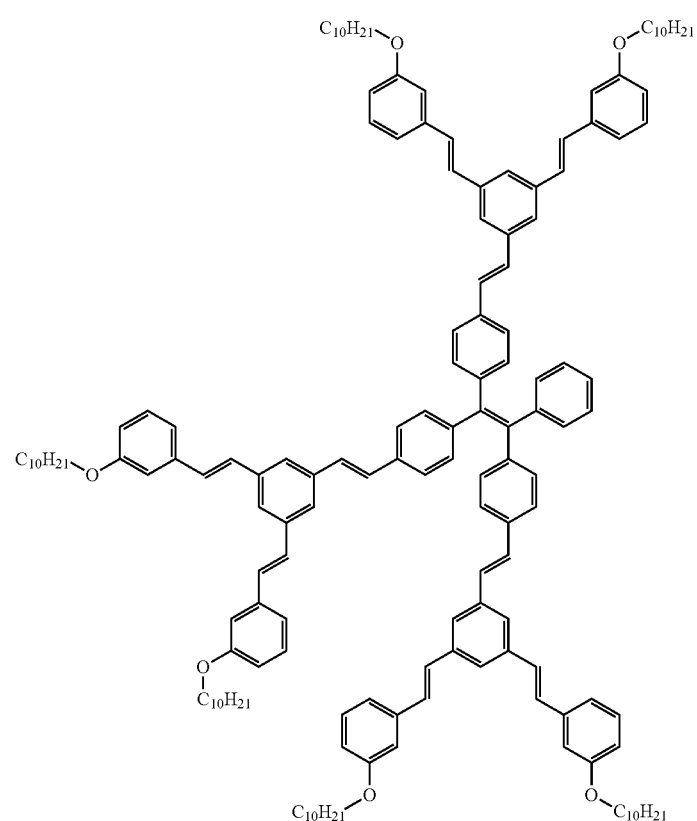

-continued
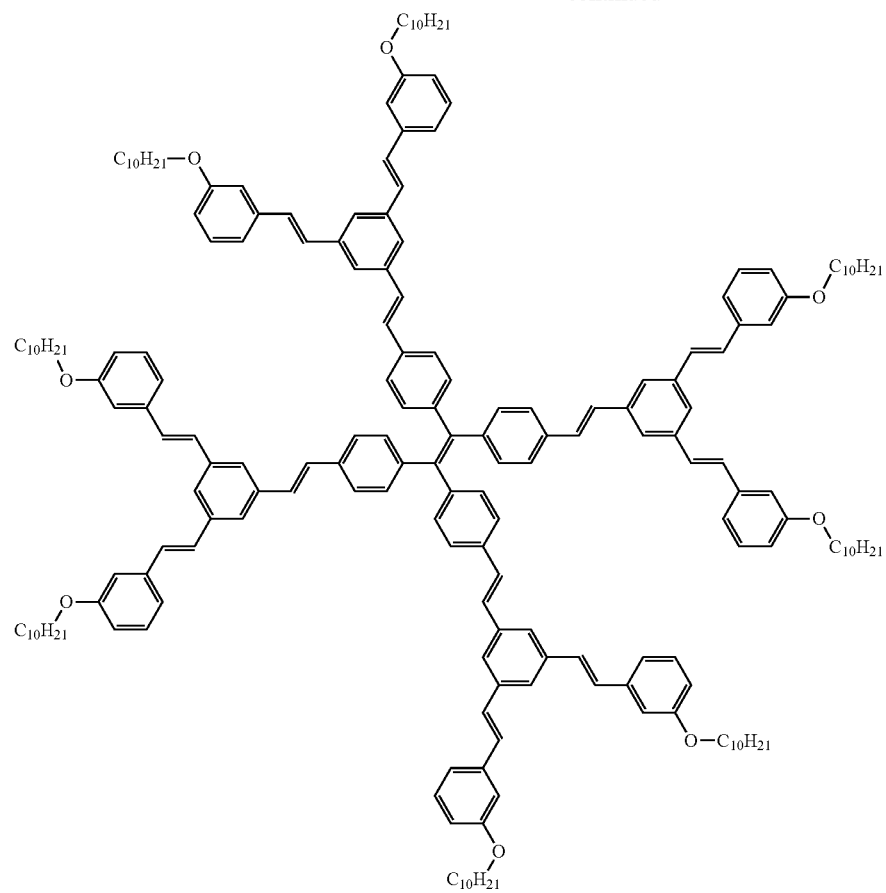
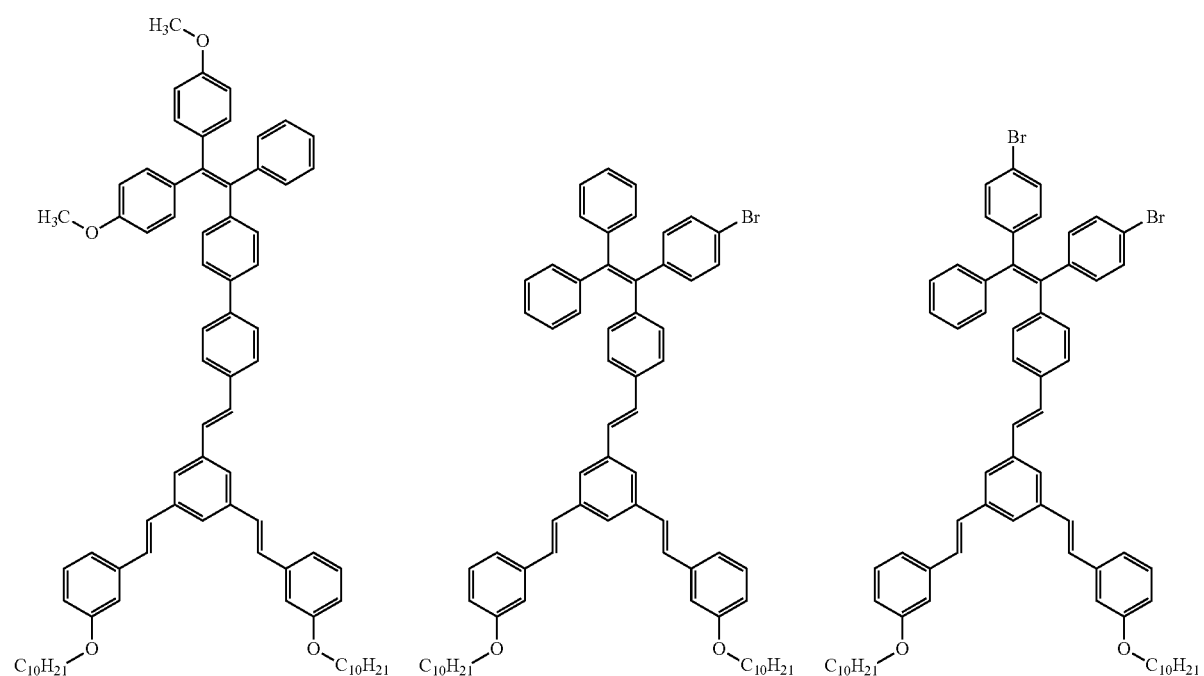

-continued
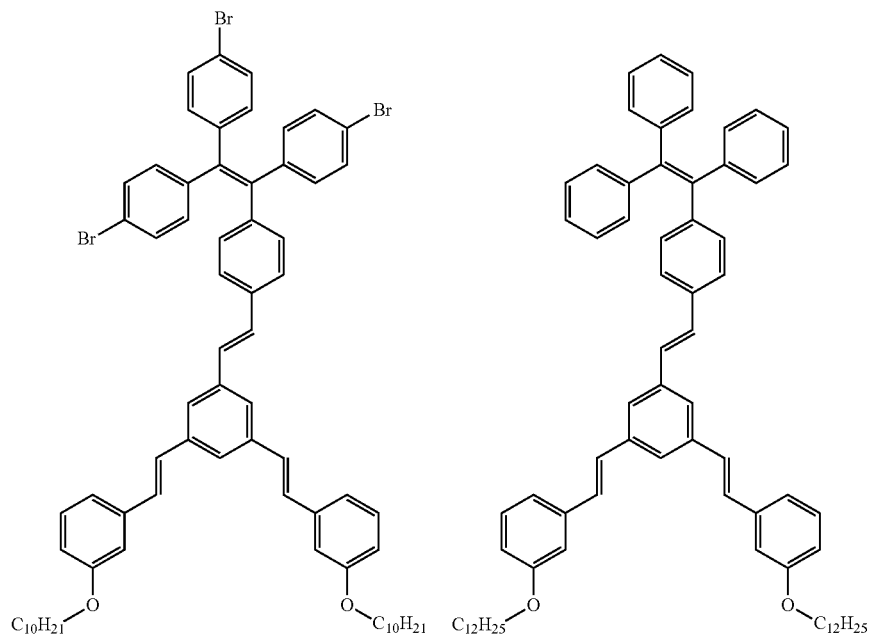
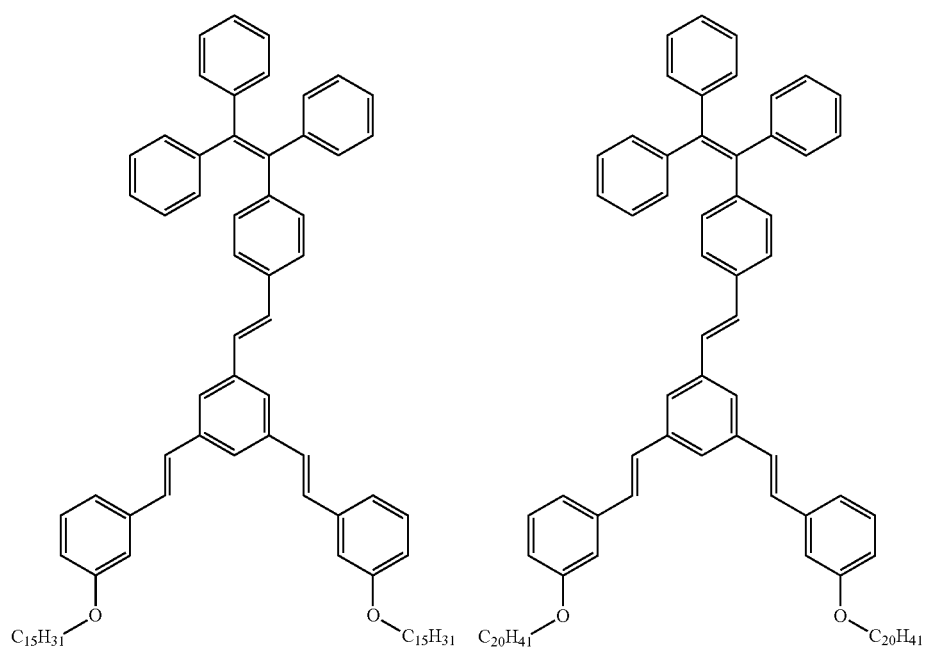

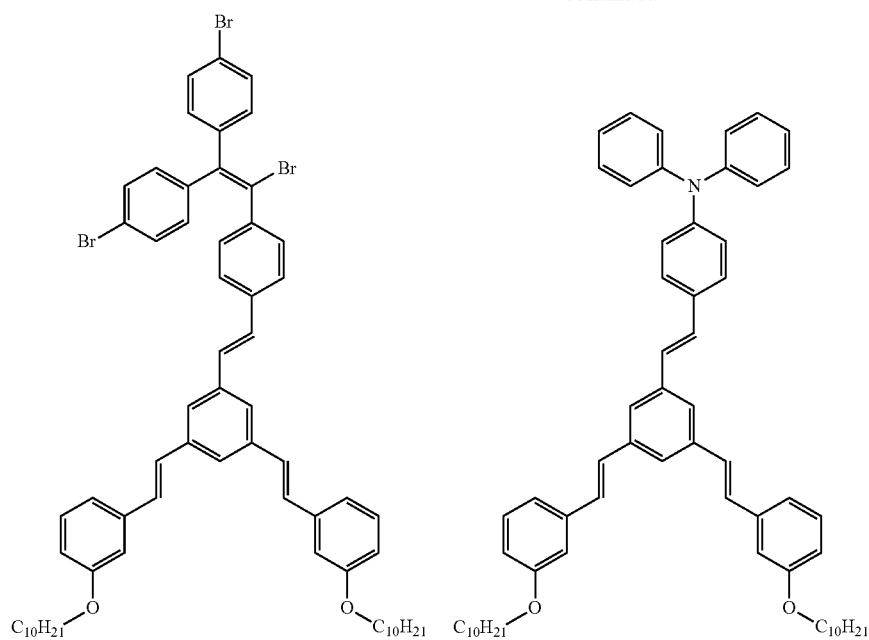
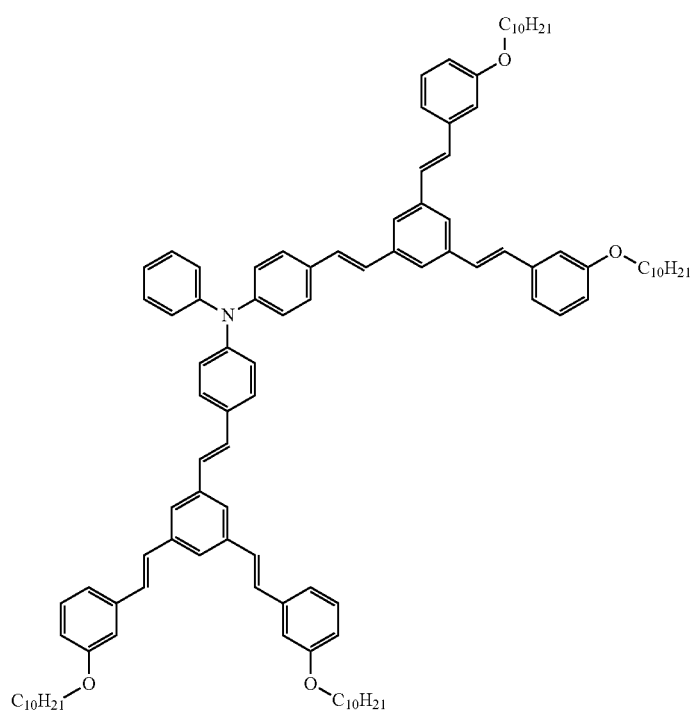

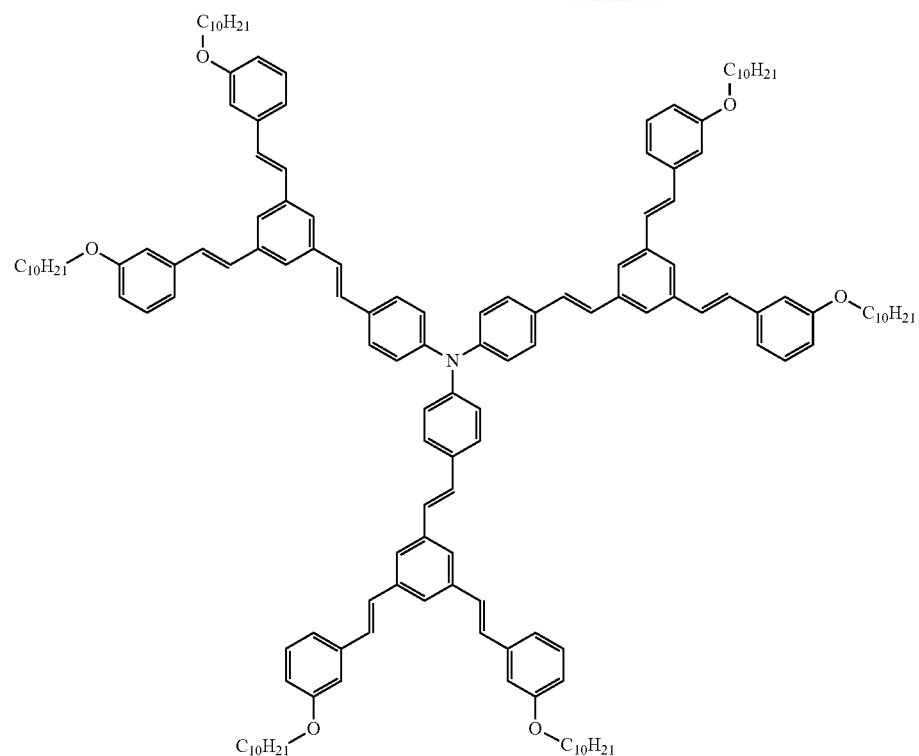
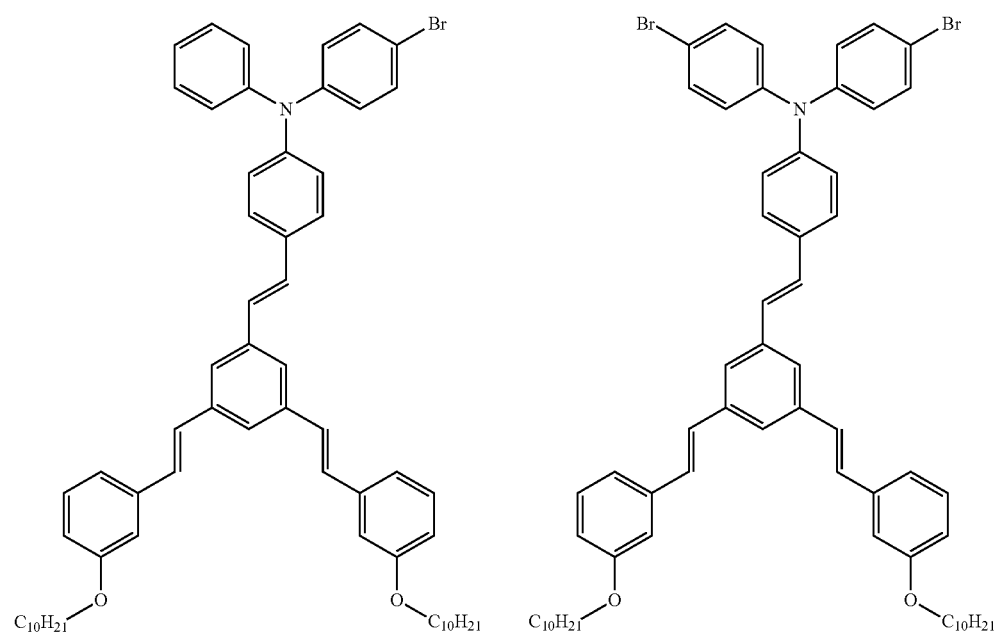

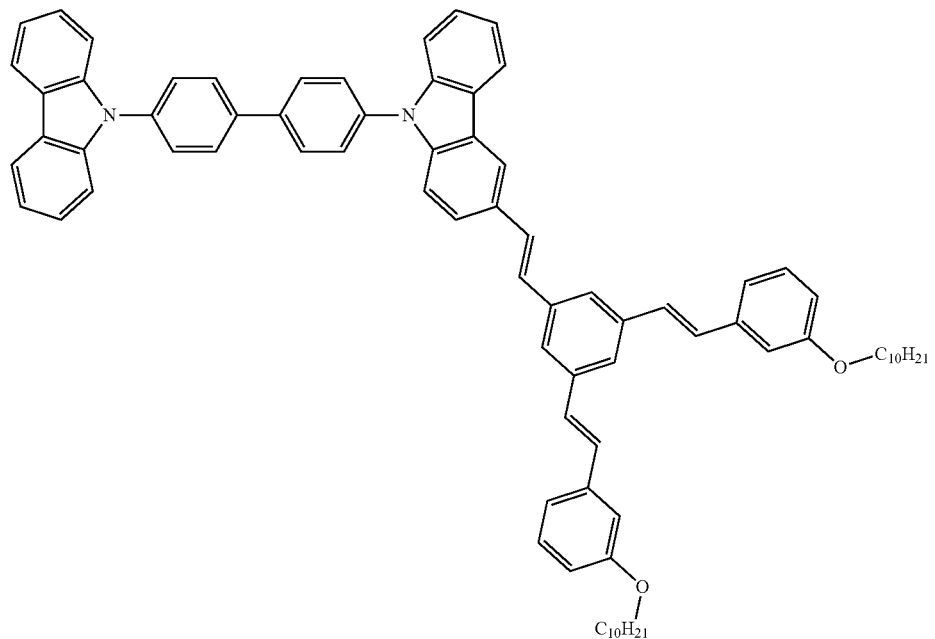
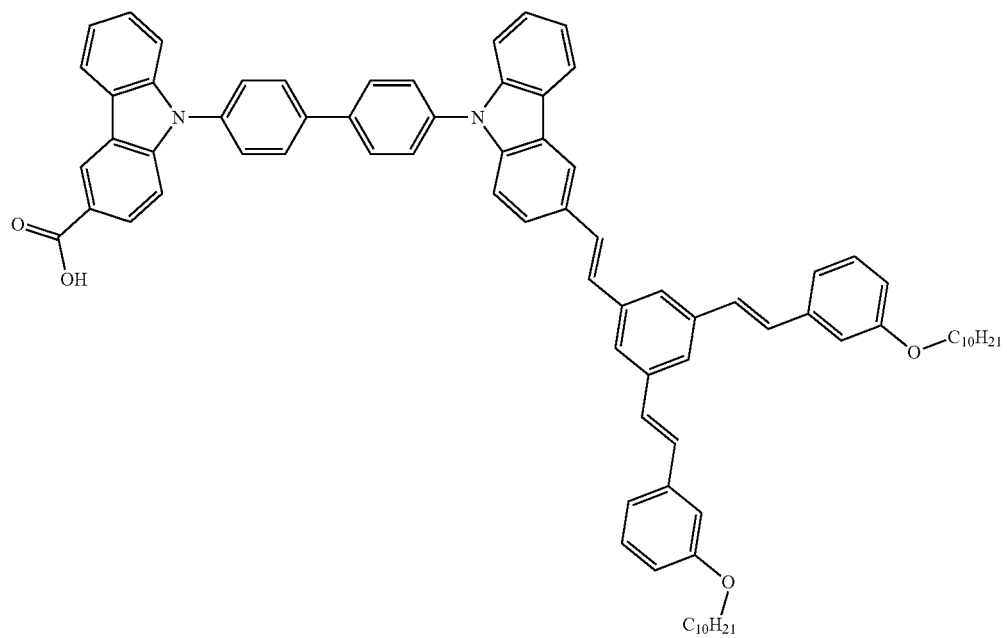

-continued
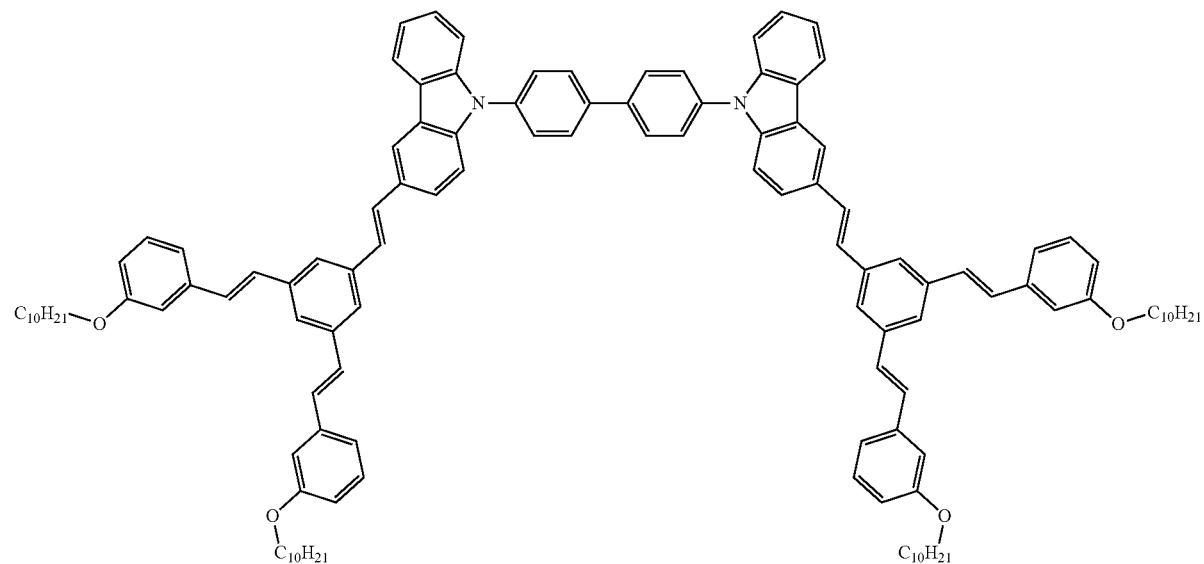
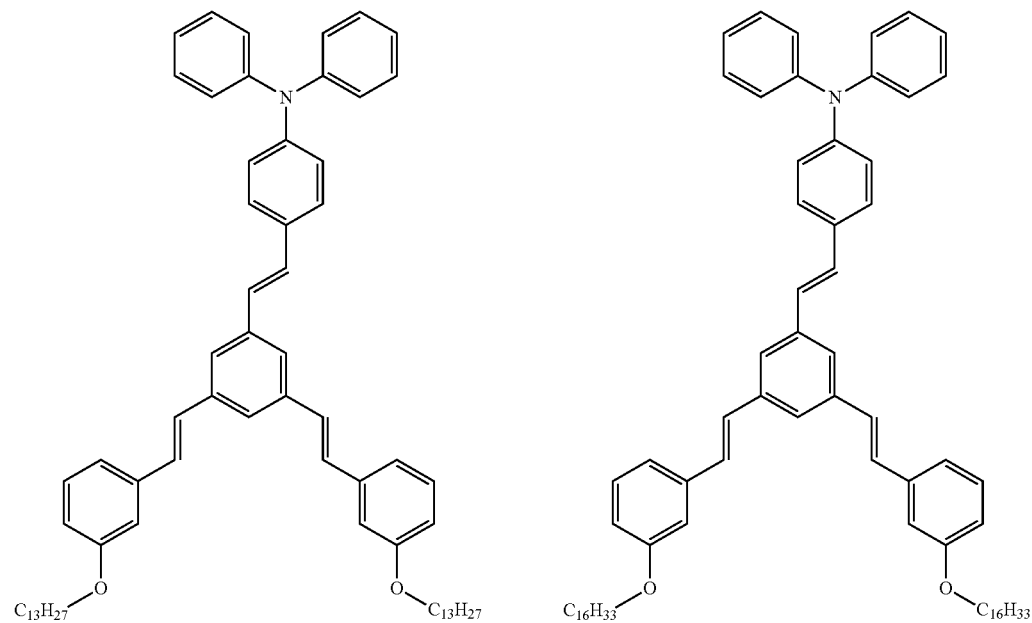

-continued
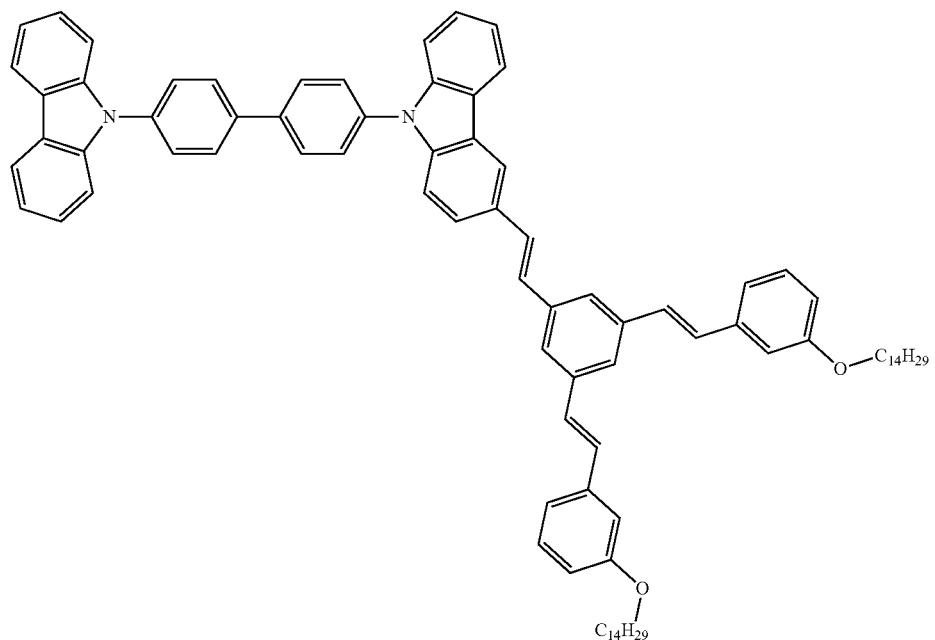
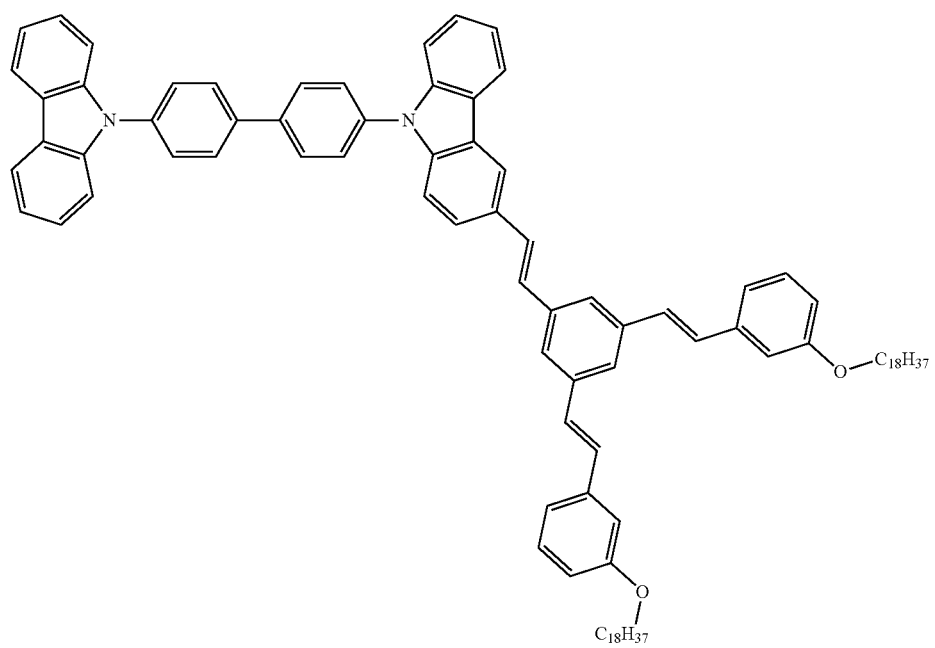

31
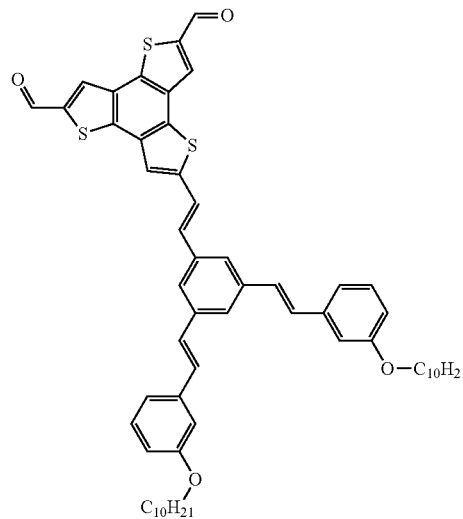
32
-continued
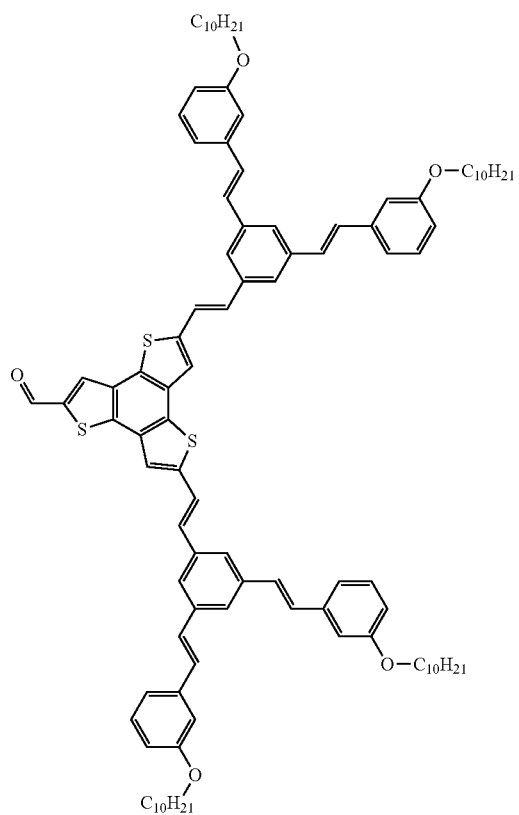
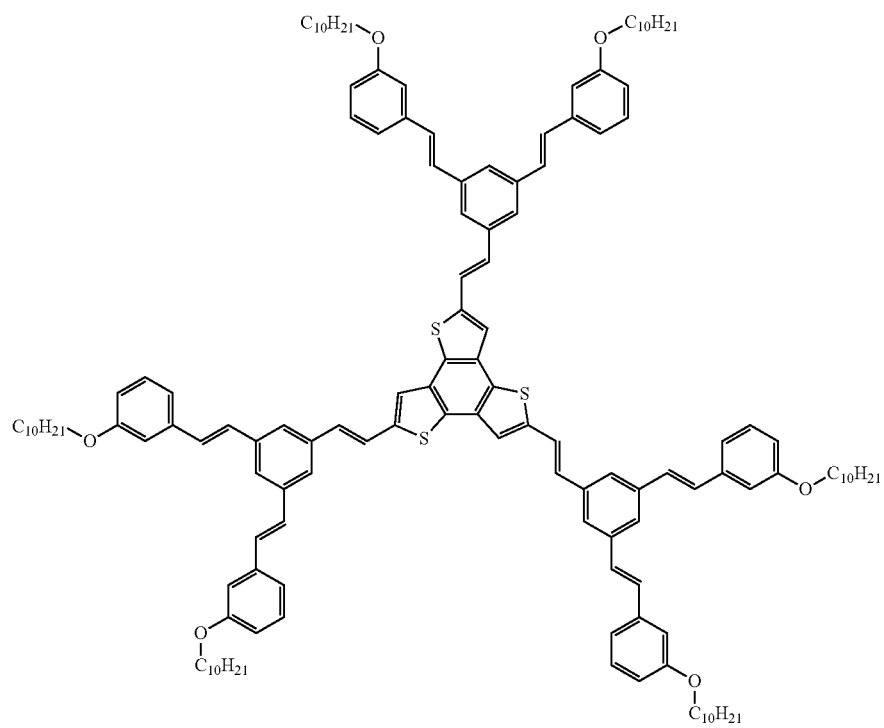

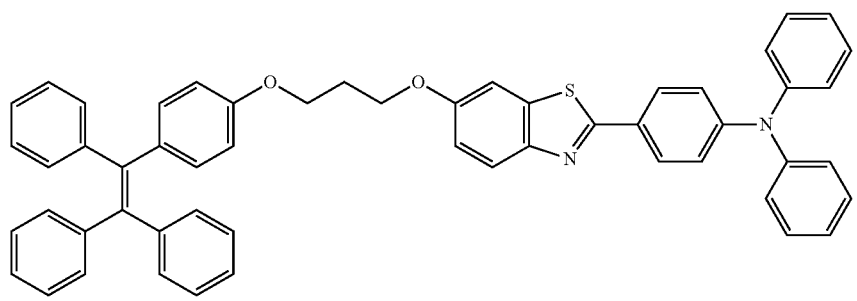
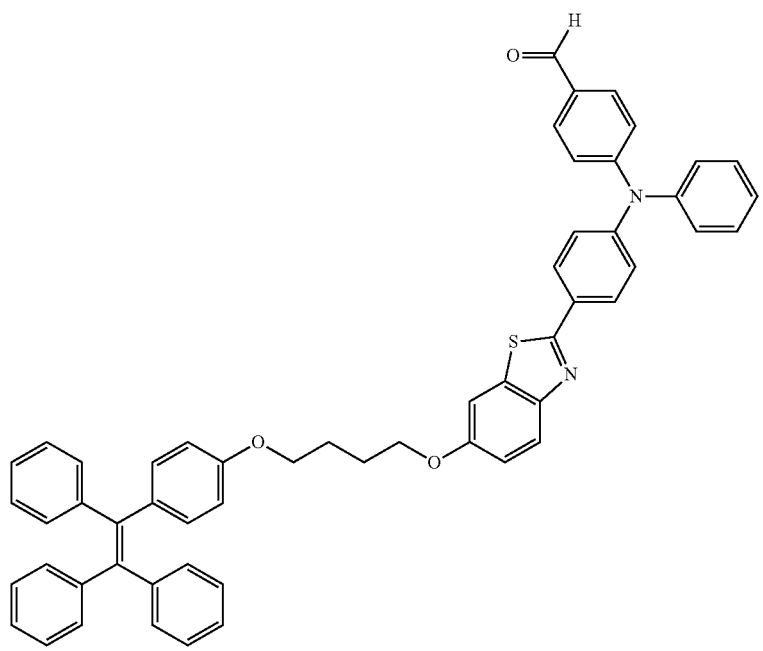
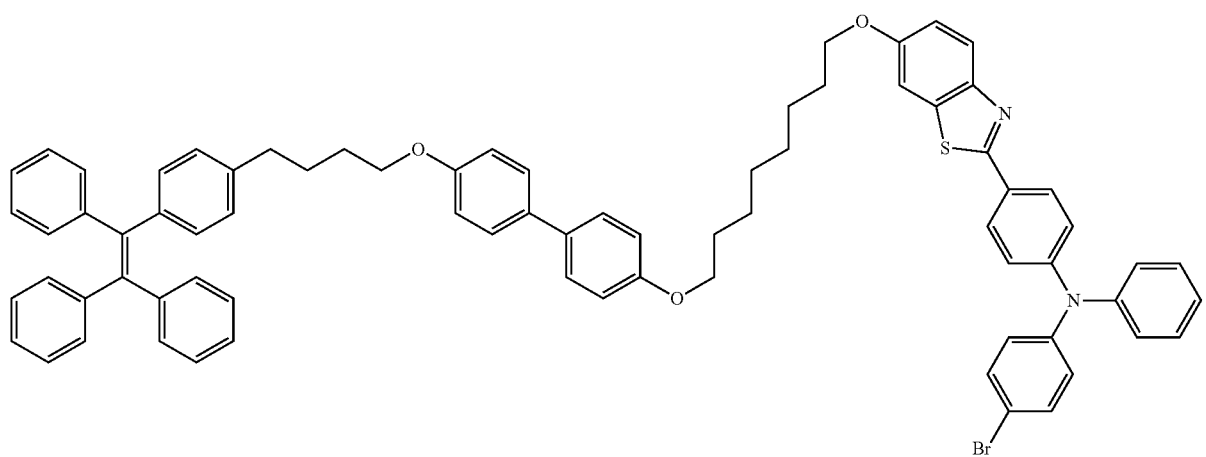

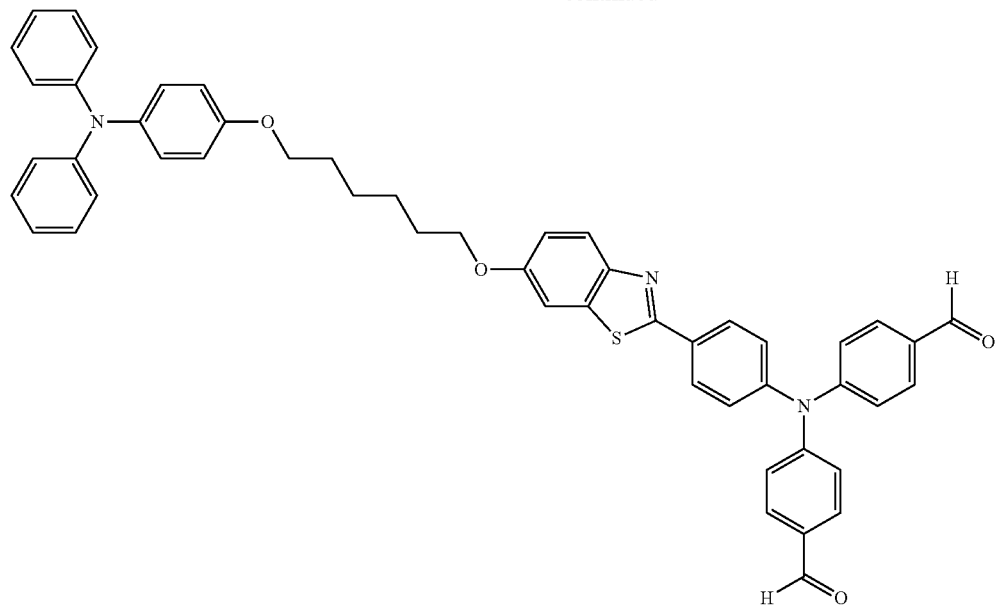
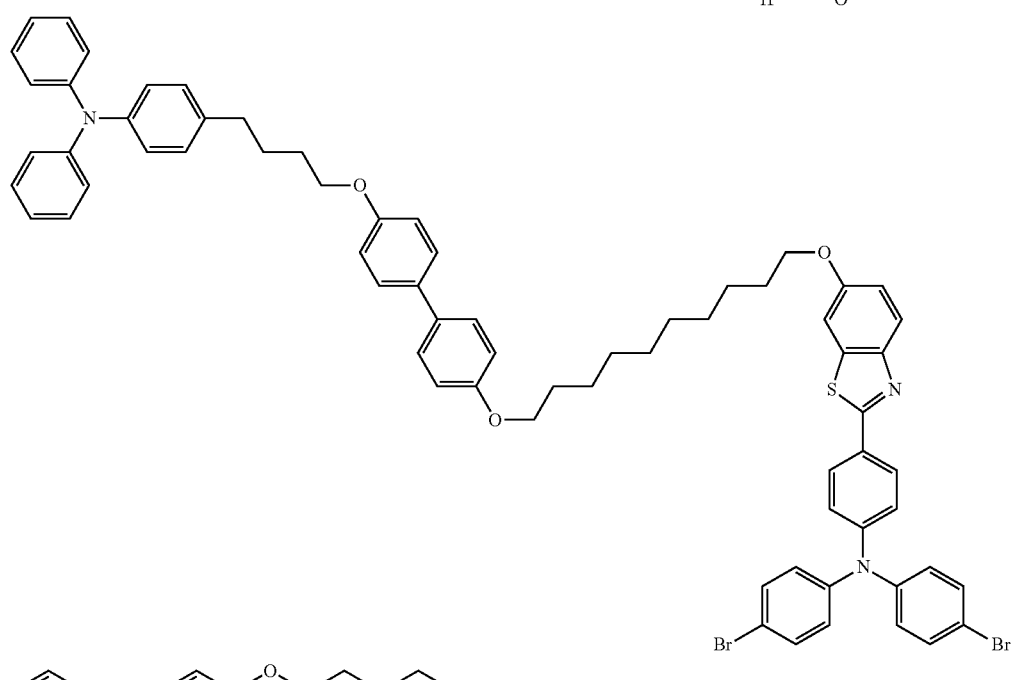
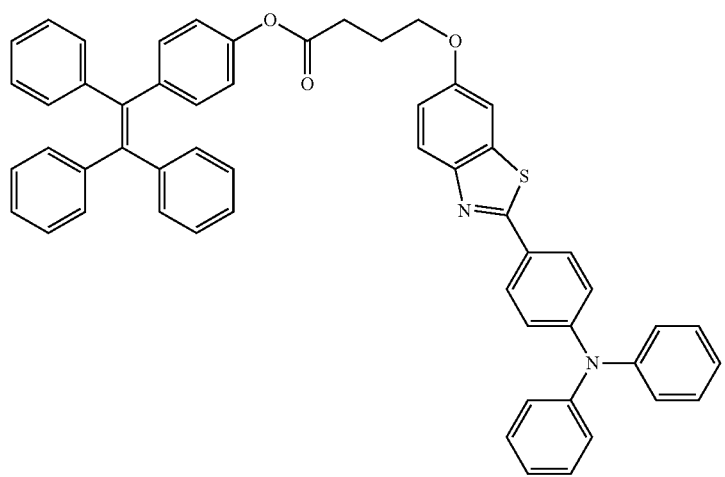

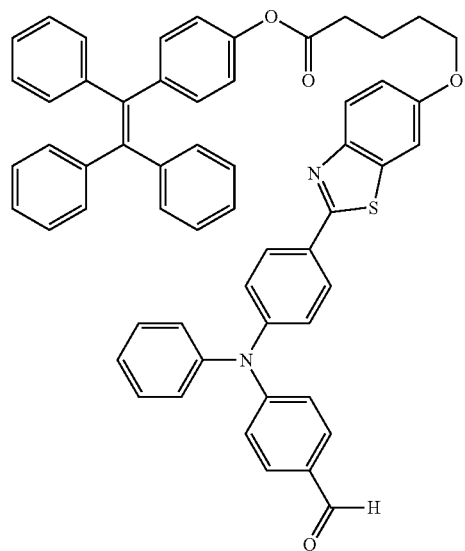
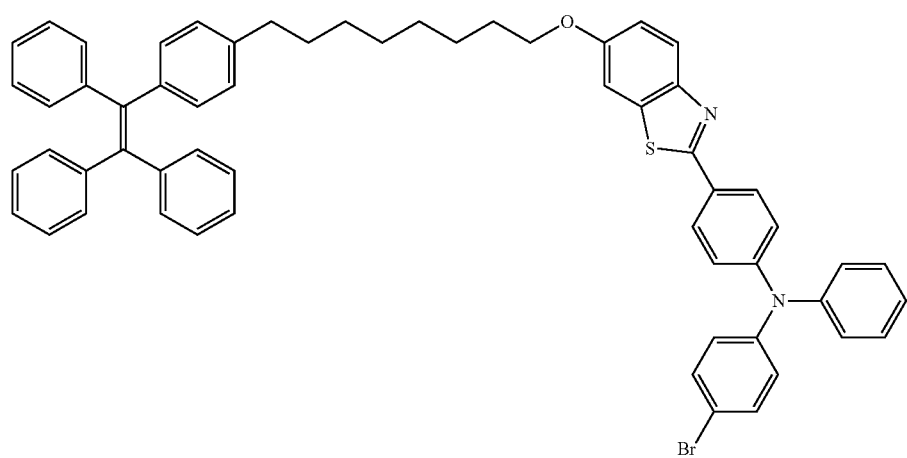
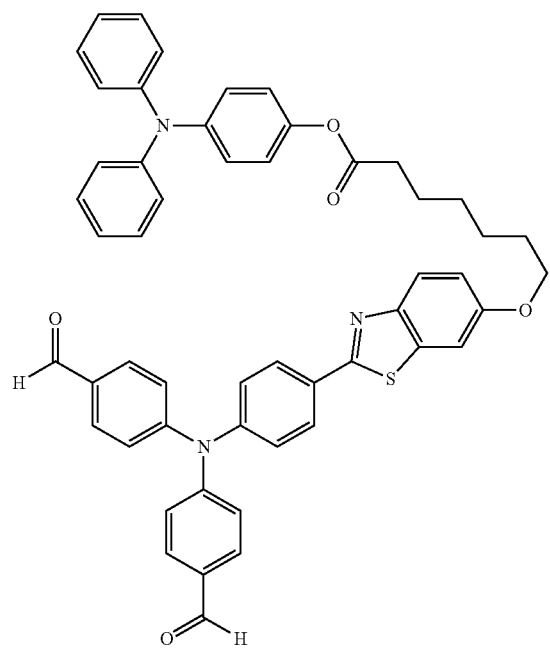

-continued
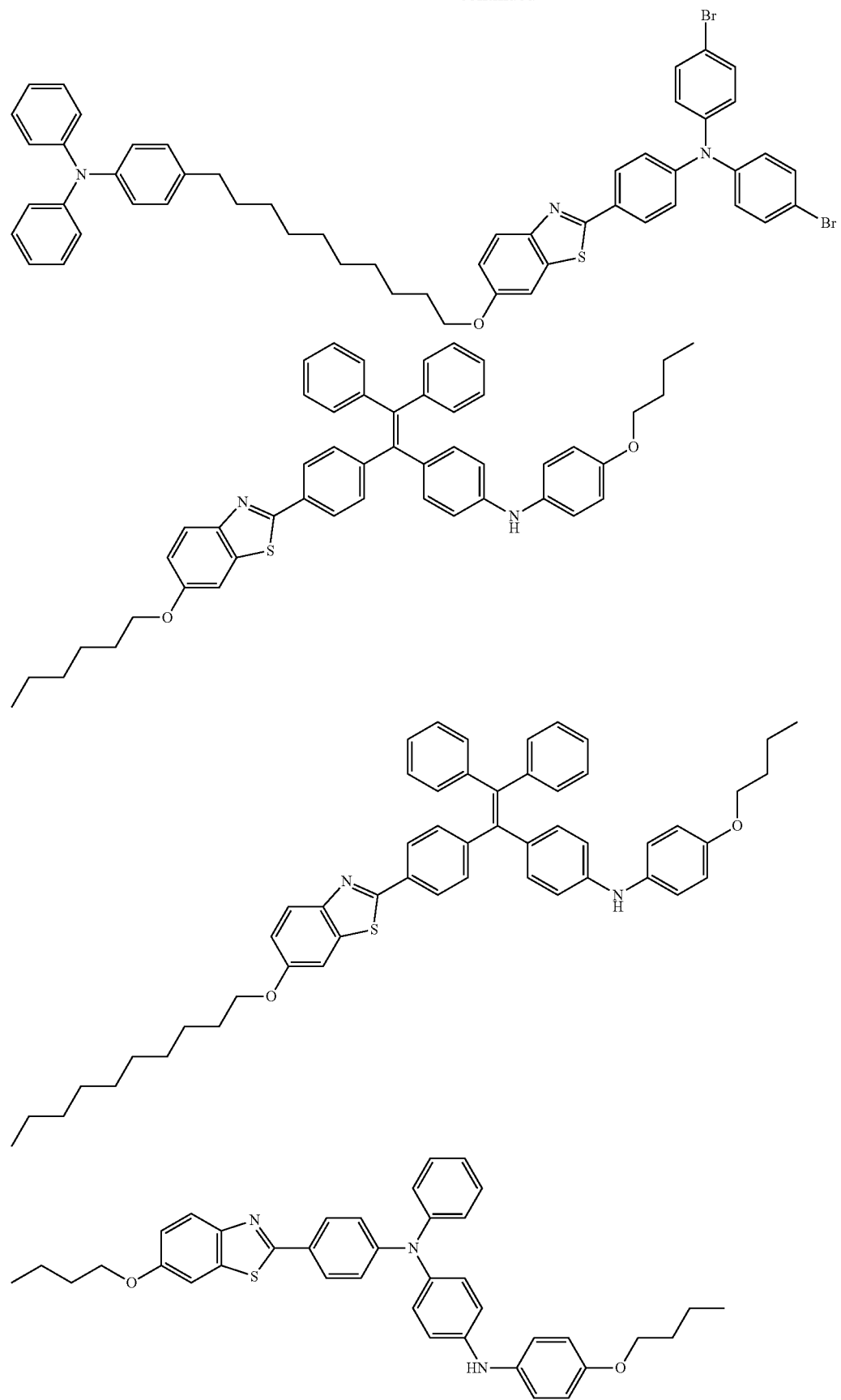

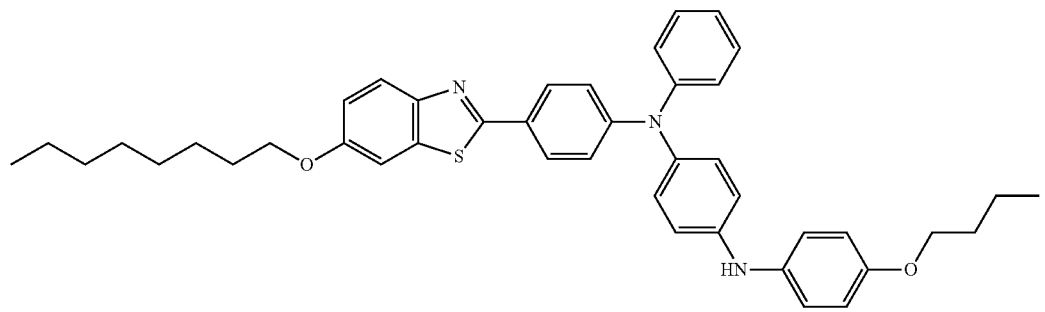
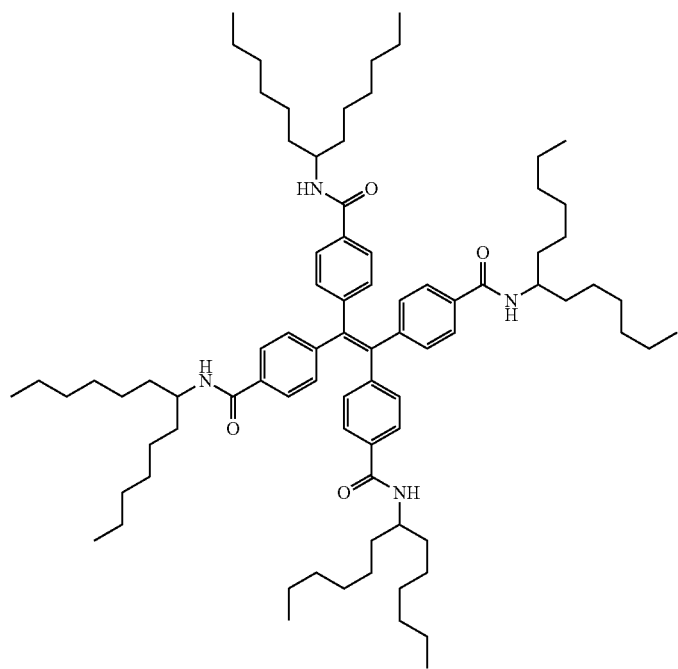

-continued
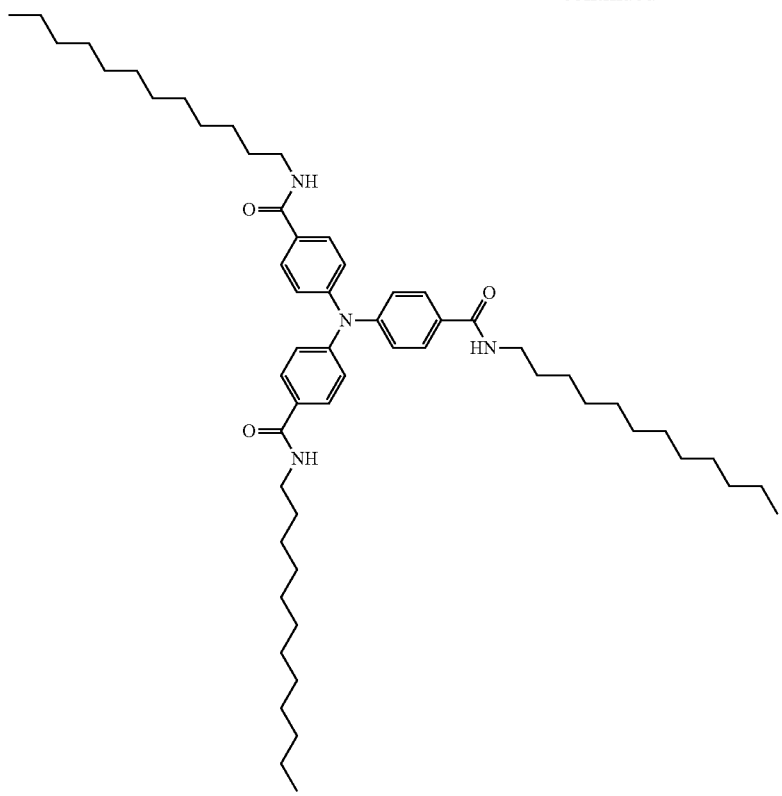
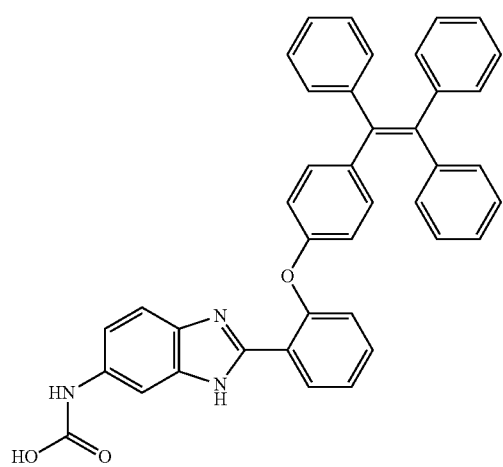

-continued
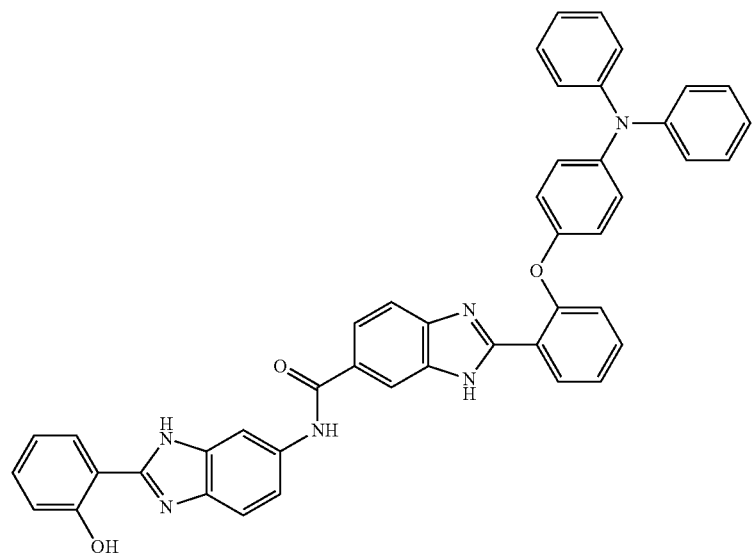
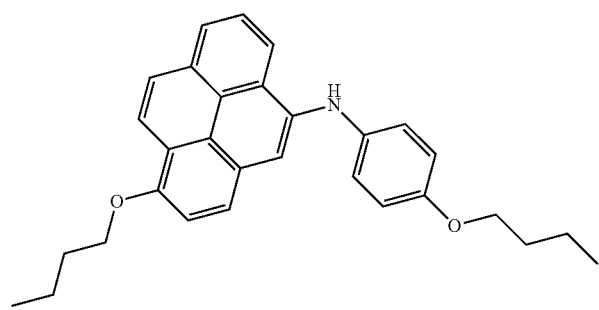
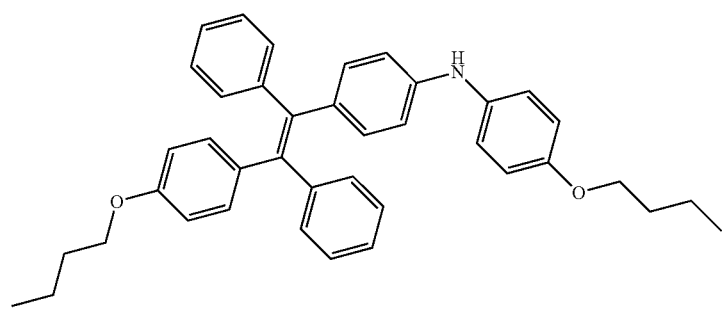

-continued
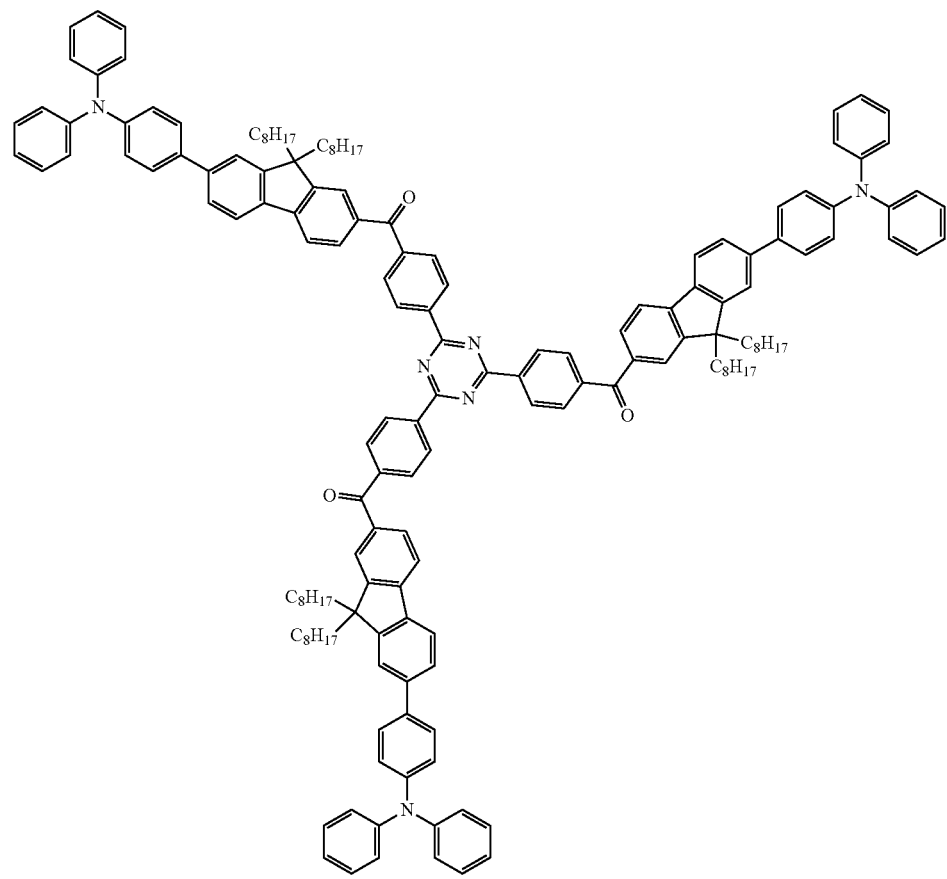
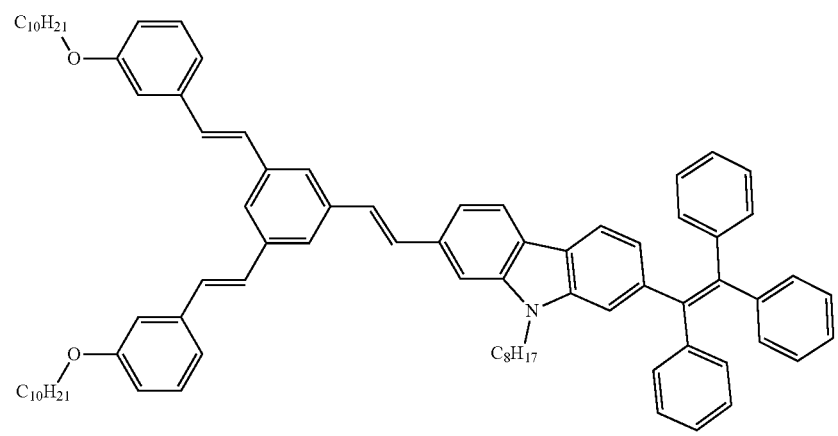

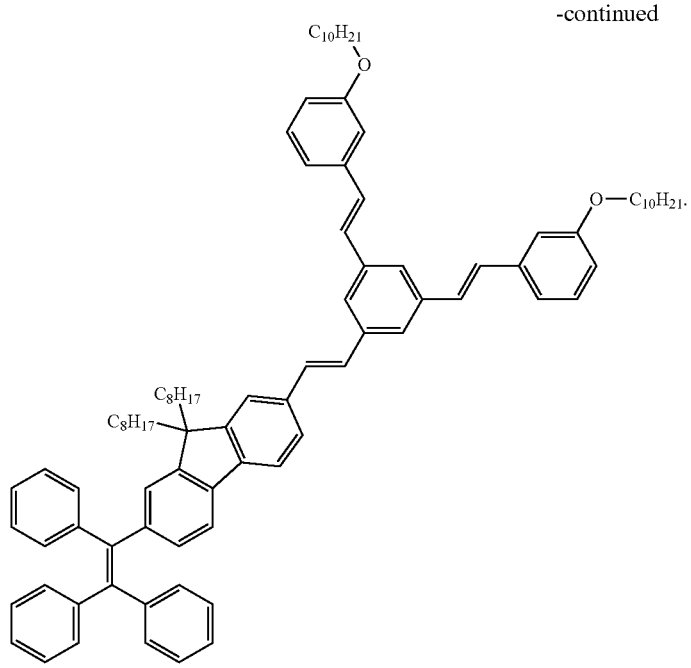
-continued

In another general aspect, an organic electronic element includes: the ferroelectric fluorescent self-assembly compound of the present invention.

The organic electronic element of the present invention may be an organic solar cell, an organic thin film transistor, an organic light-emitting element, an organic sensor, or a capacitor.

Preferably, the ferroelectric fluorescent self-assembly compound according to an exemplary embodiment of the present invention may be included in an organic layer of the organic electronic element.

In still another general aspect, an electronic device includes: the organic electronic element of the present invention.

Other features and aspects will be apparent from the following detailed description, the drawings, and the claims.

DETAILED DESCRIPTION OF EMBODIMENTS

Figure 1:
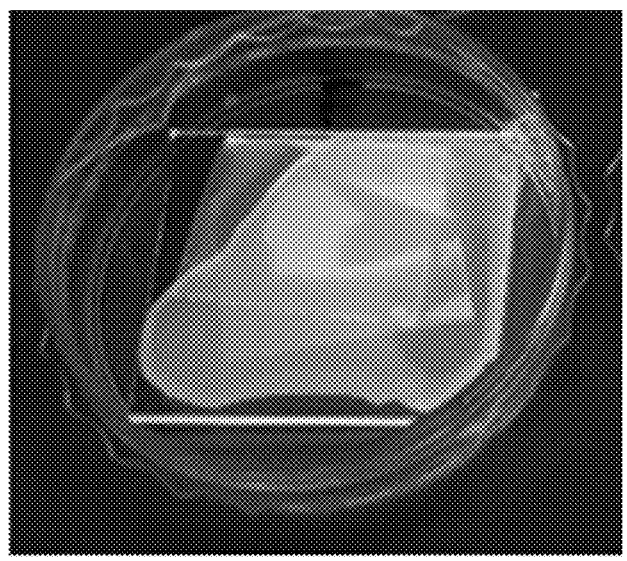
FIG. 1 is a photograph showing a light-emitting property of an organic electronic element manufactured in Example 12.
Figure 2:
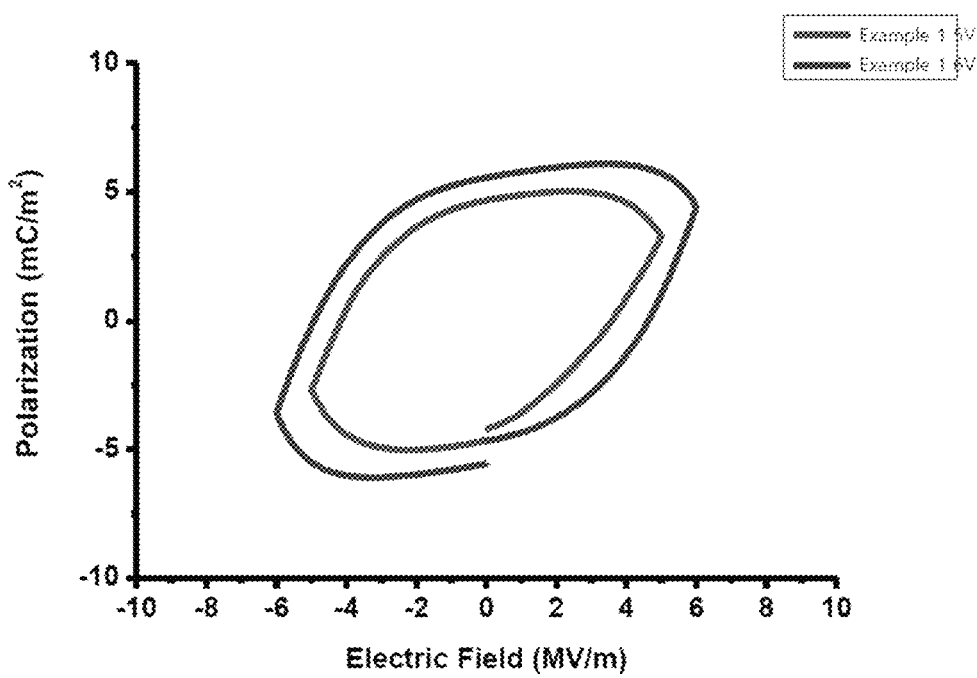
FIG. 2 is a drawing showing a P-E curve of Example 12.

Hereinafter, the present invention will be described in more detail. Technical terms and scientific terms used in the present specification have the general meaning understood by those skilled in the art to which the present invention pertains unless otherwise defined, and a description for the known function and configuration obscuring the present invention will be omitted in the following description.

The term "alkyl" used in the present specification refers to a saturated straight-chain or branched acyclic hydrocarbon having 1 to 30, preferably 1 to 20, more preferably 1 to 10, still more preferably 1 to 7, and still more preferably 1 to 4 carbon atoms (where the number of carbon atoms is not particularly limited). A representative saturated straight-chain alkyl includes methyl, -ethyl, -n-propyl, -n-butyl, -n-pentyl, -n-hexyl, -n-heptyl, -n-octyl, -n-nonyl, and -n-decyl, while saturated branched alkyl includes -isopropyl, -sec-butyl, -isobutyl, -tert-butyl, isopentyl, 2-methylhexyl, 3-methylbutyl, 2-methylpentyl, 3-methylpentyl, 4-methylpentyl, 2-methylhexyl, 3-methylhexyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl.

In the present specification, the description such as "$C_{1-5}$" means that the number of carbon atoms is 1 to 5. For example, $C_{1-5}$ alkyl means alkyl having 1 to 5 carbon atoms.

The terms "halogen" and "halo" used in the present specification refer to fluorine, chlorine, bromine, or iodine.

The term "alkoxy" used in the present specification refers to —O-(alkyl), in which alkyl means a saturated straight-chain or branched acyclic hydrocarbon having 1 to 30, preferably 2 to 30, more preferably 4 to 30, still more preferably 4 to 25, and still more preferably 10 to 25 carbon atoms, and as an example, may include —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(CH$_2$)$_5$CH3, and the like, but is not limited thereto. In addition, alkoxy of the present invention may be a saturated straight-chain or branched acyclic hydrocarbon having 1 to 30, preferably 1 to 20, more preferably 1 to 10, and still more preferably 1 to 6 carbon atoms.

The term "alkenyl" used in the present specification refers to an unsaturated alkyl group which has at least one double bond and 2 to 30, preferably 2 to 20, more preferably 2 to 10, and still more preferably 2 to 6 carbon atoms and is attached to the remaining portion of a molecule by a single bond, for example, ethenyl, propenyl, butenyl, pentenyl, hexenyl, and the like.

The term "aryl" used in the present specification refers to a carbocyclic aromatic group containing 5 to 10 ring atoms. A representative example includes phenyl, tolyl, xylyl, naphthyl, tetrahydronaphthyl, anthracenyl, fluorenyl, indenyl, azulenyl, and the like, but is not limited thereto. The carbocyclic aromatic group may be selectively substituted.

"Heteroaryl" used in the present specification is a 5- to 10-membered aromatic heterocycle containing at least one carbon atom including a mono- and bicyclic ring system and having at least one heteroatom selected from the group consisting of nitrogen, oxygen, and sulfur. Representative heteroaryl is triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrizinyl, triazinyl, cinnolinyl, phthalazinyl, quinazolinyl, pyrimidyl, oxetanyl, azepinyl, piperazinyl, morpholinyl, dioxanyl, thietanyl, and oxazolyl. A heteroaryl group may be monocyclic or bicyclic. The heteroaryl may be used interchangeably with a heteroaryl ring, a heteroaryl group, or heteroaromatic, and these terms may all include an optionally substituted ring.

The terms "alkylene" and "alkinylene" used in the present specification are a diradical of the alkane, that is, a divalent radical.

The term "alkylene" used in the present specification refers to a straight-chain or branched divalent hydrocarbon composed of only a single bond of carbon and hydrogen, in which the remaining part of a molecule is connected to a radical ring.

The term "trivalent alkyl radical" used in the present specification refers to a trivalent radical of the alkane. As an example, in Chemical Formula 1 of the present invention, $A_2$ and $A_{11}$ refer to a trivalent hydrocarbon composed of only a single bond of carbon and hydrogen, together.

In the present specification, "trivalent arylene" and "heteroarylene" also refer to an aromatic or heteroaromatic compound having a trivalent radical, and refer to ca trivalent aromatic or heteroaromatic hydrocarbon, as in $A_2$ and $A_{11}$ in Chemical Formula 1 of the present invention.

Hereinafter, the present disclosure will be described in detail.

The present invention provides a ferroelectric fluorescent self-assembly compound capable of self-assembly.

Specifically, the present invention provides a ferroelectric fluorescent self-assembly compound to which a specific skeleton is introduced and in which one or more specific functional groups capable of self-assembly are introduced to the specific skeleton, and since the ferroelectric fluorescent self-assembly compound of the present invention allows self-assembly and has excellent piezoelectricity and ferroelectricity, an organic electronic element adopting the compound has surprisingly improved optical properties.

The ferroelectric fluorescent self-assembly compound of the present invention is represented by the following Chemical Formula 1:

[Chemical Formula 1]

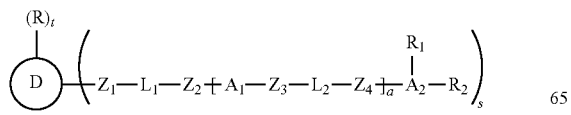

wherein

R is a halogen, CHO, or (C1-C30)alkoxy;

D is selected from the following structures as a main skeleton:

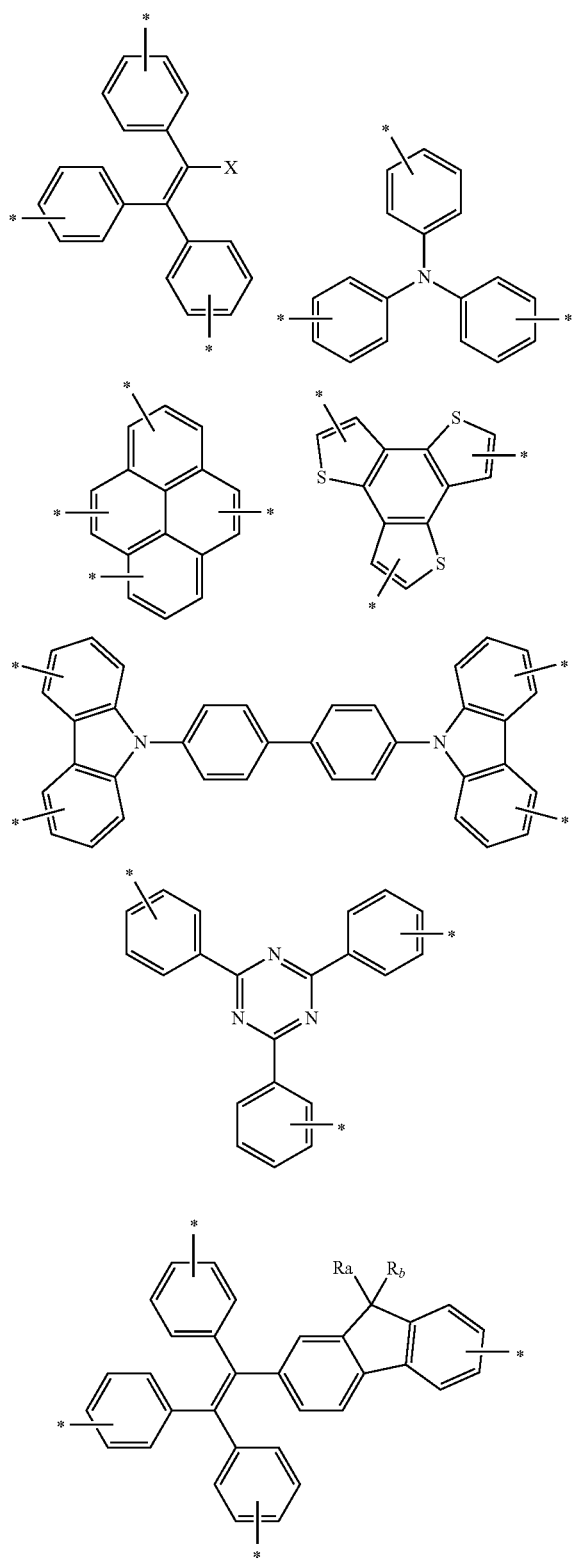

-continued

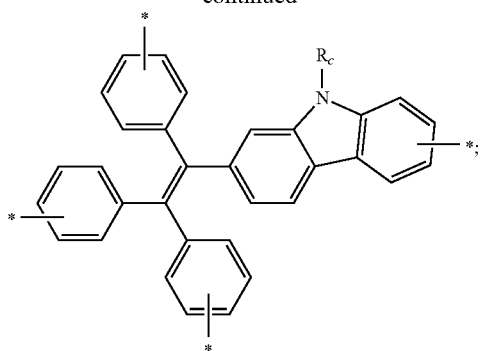

X is a halogen or

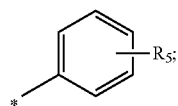

$R_a$, $R_b$, and $R_c$ are independently of one another (C1-C30) alkyl;

$Z_1$ to $Z_4$ are independently of one another a single bond, —O—, —CO—, —OCO—, —COO—, —NH—, —CONH—, —NHCO—, or C2-C30 alkenylene;

$L_1$ and $L_2$ are independently of each other a single bond, C1-C30 alkylene, C2-C30 alkenylene, or C6-C30 arylene;

$A_1$ is C1-C30 alkylene, C6-C30 arylene, C1-C20 alkyl C6-C30 arylene, or C3-C30 heteroarylene;

$A_2$ and $A_{11}$ are independently of each other a trivalent C1-C30 alkyl radical, a trivalent C6-C30 aryl radical, or a trivalent C6-C30 aryl radical or a trivalent C3-C30 heteroaryl radical substituted with C1-C30 alkyl;

a is an integer of 0 or 2;

$R_1$, $R_2$, and $R_5$ are independently of one another hydrogen, a halogen, C1-C30 alkoxy,

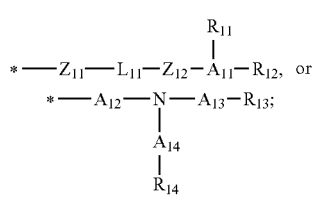

$Z_{11}$ and $Z_{12}$ are independently of each other a single bond, —O—, —OCO—, —COO—, —NH—, —CONH—, —NHCO—, or C2-C20 alkenylene;

$L_{11}$ is a single bond, C1-C30 alkylene, C2-C30 alkenylene, or C6-C30 arylene;

$A_{11}$ to $A_{14}$ are independently of one another C1-C30 alkylene, C6-C30 arylene, or C6-C30 arylene or C3-C30 heteroarylene substituted with C1-C30 alkyl;

$R_{11}$ to $R_{14}$ are independently of one another hydrogen, halogen, C1-C30 alkoxy, CHO, OH, or NHCOOH;

s is an integer of 1 to 4;

t is an integer of 0 to 3; and s+t≤an integer representing the number of substituent sites possessed by the main skeleton D is satisfied.

The ferroelectric fluorescent self-assembly compound of the present invention adopts a specific main skeleton, specifically,

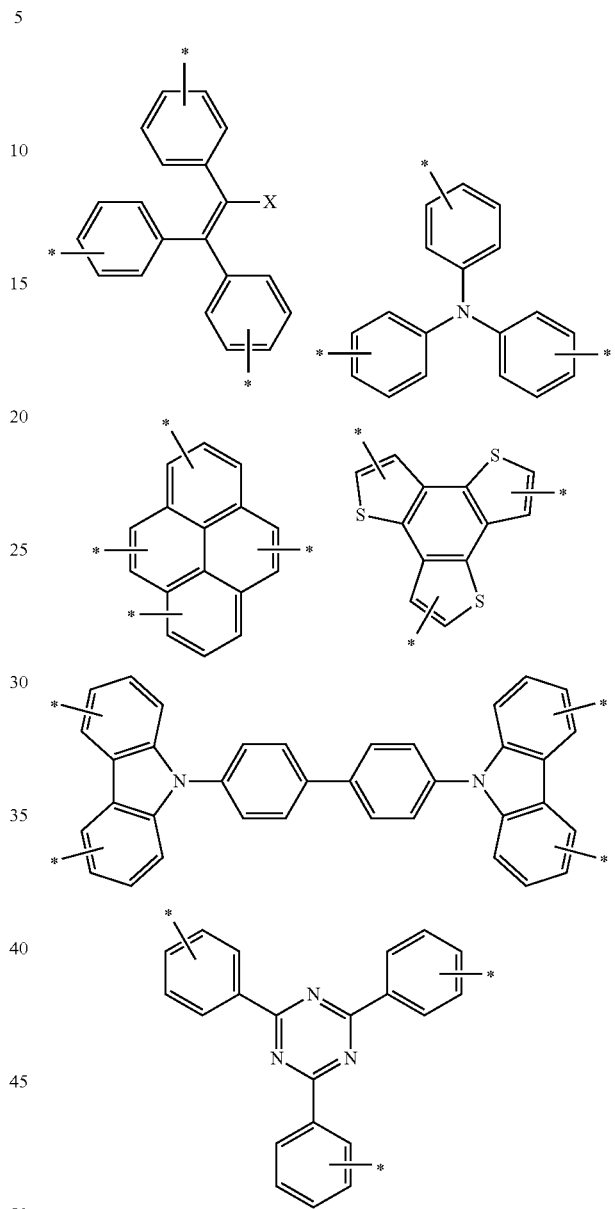

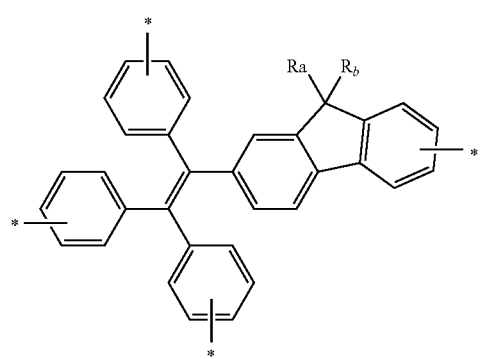

-continued

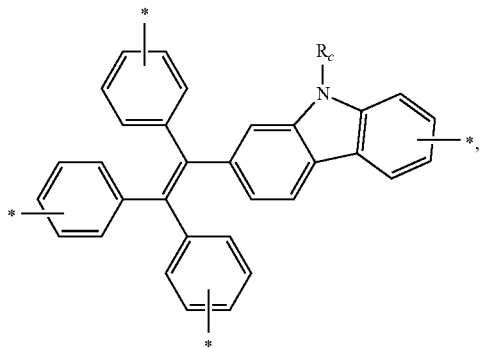

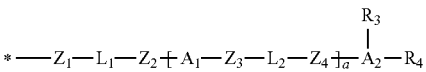

which is a specific substituent capable of self-assembly in the specific skeleton, thereby having surprisingly improved light-emitting property and piezoelectricity and having ferroelectricity.

Even more surprisingly, the ferroelectric fluorescent self-assembly compound of the present invention has an advantage of a light-emitting property being not deteriorated while allowing self-assembly.

Preferably, Chemical Formula 1 according to an exemplary embodiment of the present invention may be represented by the following Chemical Formulae 2 to 9:

[Chemical Formula 2]

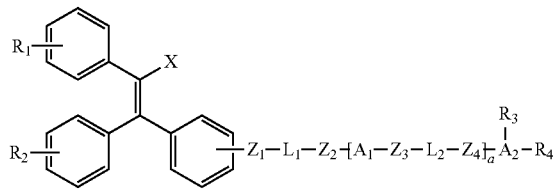

[Chemical Formula 3]

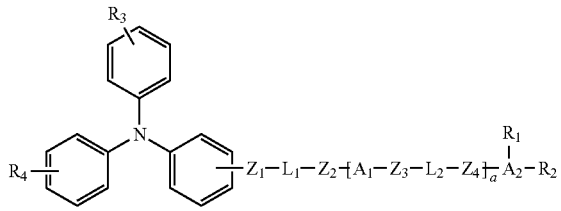

[Chemical Formula 4]

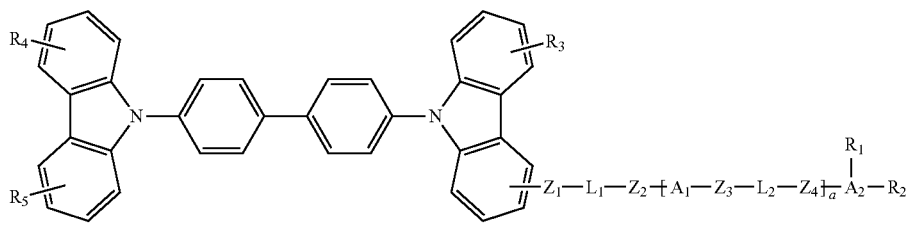

[Chemical Formula 5]

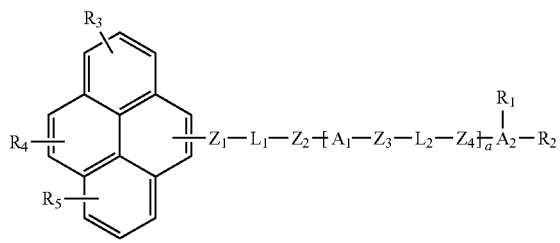

[Chemical Formula 6]

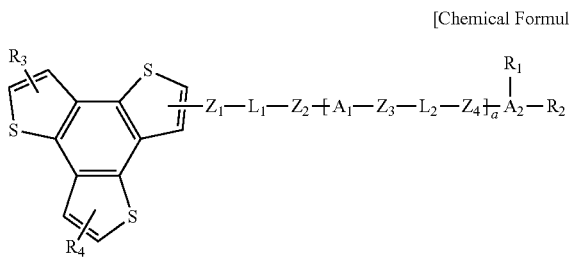

[Chemical Formula 7]

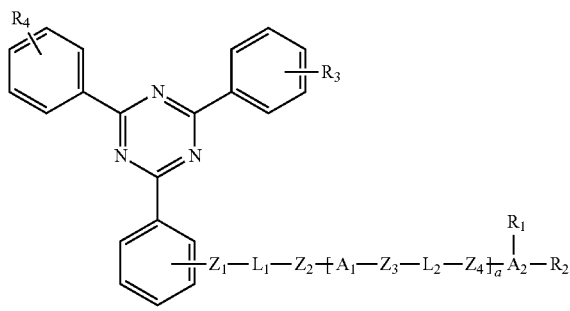

[Chemical Formula 8]

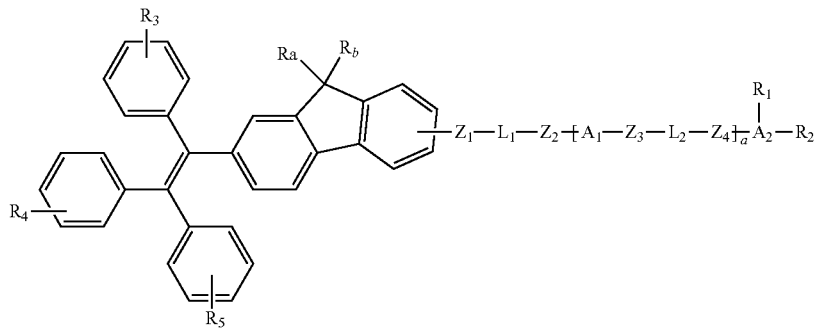

[Chemical Formula 9]

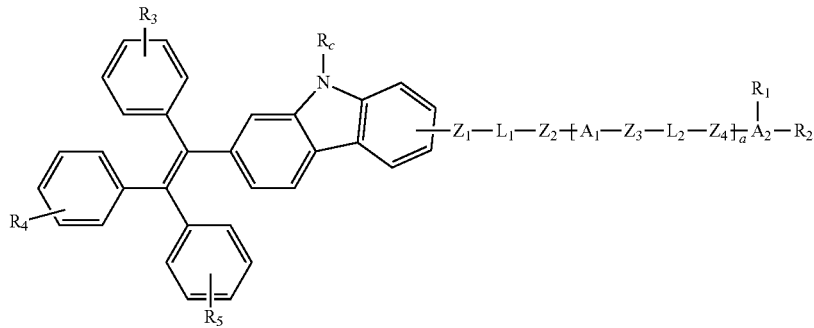

wherein
X is a halogen or

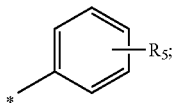

$Z_1$ to $Z_4$ are independently of one another a single bond, —O—, —CO—, —OCO—, —COO—, —NH—, —CONH—, —NHCO—, or C2-C30 alkenylene;

$L_1$ and $L_2$ are independently of each other a single bond, C1-C30 alkylene, C2-C30 alkenylene, or C6-C30 arylene;

$A_1$ is C1-C30 alkylene, C6-C30 arylene, C1-C20 alkyl C6-C30 arylene or C3-C30 heteroarylene;

$A_2$ and $A_{11}$ are independently of each other a trivalent C1-C30 alkyl radical, a trivalent C6-C30 aryl radical, or a trivalent C6-C30 aryl radical or a trivalent C3-C30 heteroaryl radical substituted with C1-C30 alkyl;

a is an integer of 0 or 2;

$R_a$, $R_b$, and $R_c$ are independently of one another (C1-C30) alkyl;

$R_1$ and $R_2$ may be independently of each other hydrogen, a halogen, C1-C30 alkoxy,

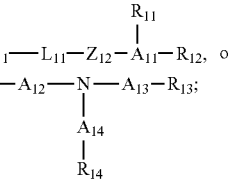

$R_3$ to $R_5$ are independently of one another hydrogen, halogen, C1-C30 alkoxy,

*—$Z_1$—$L_1$—$Z_2$+$A_1$—$Z_3$—$L_2$—$Z_4$$\frac{}{a}$$A_2$—$R_4$, or

*—$Z_{11}$—$L_{11}$—$Z_{12}$—$A_{11}$—$R_{12}$;

$Z_{11}$ and $Z_{12}$ are independently of each other a single bond, —O—, —OCO—, —COO—, —NH—, —CONH—, —NHCO—, or C2-C20 alkenylene;

$L_{11}$ is a single bond, C1-C30 alkylene, C2-C30 alkenylene, or C6-C30 arylene;

$A_{11}$ to $A_{14}$ are independently of one another C1-C30 alkylene, C6-C30 arylene, or C3-C30 heteroarylene; and $R_{11}$ to $R_{14}$ are independently of one another hydrogen, halogen, C1-C30 alkoxy, CHO, OH, or NHCOOH.

Preferably, in Chemical Formulae 2 to 9 according to an exemplary embodiment of the present invention, X may be a halogen or

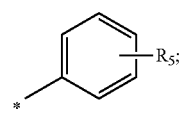

$Z_1$ to $Z_4$ may be independently of one another a single bond, —O—, —CO—, —OCO—, —NH—, —CONH—, or C2-C6 alkenylene; $L_1$ and $L_2$ may be independently of each other a single bond, C1-C10 alkylene, C2-C10 alkenylene, or C6-C12 arylene; $A_1$ may be C1-C20 alkylene, C6-C20 arylene, C1-C20 alkyl C6-C20 arylene, or C3-C20 heteroarylene; $A_2$ and $A_{11}$ may be independently of each other a trivalent C1-C20 alkyl radical, a trivalent C6-C20 aryl radical, or a trivalent C6-C20 aryl radical or a trivalent C3-C20 heteroaryl radical substituted with C1-C20 alkyl; a may be an integer of 0 or 1; $R_a$, $R_b$, and $R_c$ may be independently of one another (C1-C20)alkyl; $R_1$, $R_2$, and $R_5$ may be independently of one another hydrogen, a halogen, C1-C30 alkoxy,

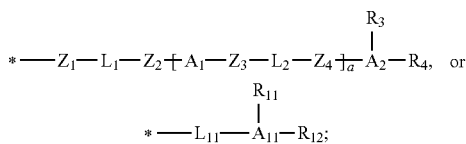

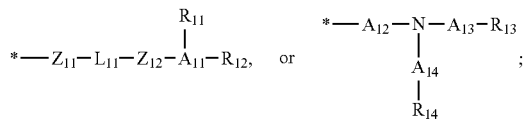

$R_3$ and $R_4$ may be independently of each other hydrogen, a halogen, C1-C30 alkoxy,

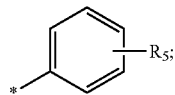

$Z_{11}$ and $Z_{12}$ may be independently of each other a single bond, —O—, —OCO—, —NH—, —CONH—, or C2-C6 alkenylene; $L_{11}$ may be a single bond, C1-C10 alkylene, C2-C10 alkenylene, or C6-C12 arylene; $A_{11}$ to $A_{14}$ may be independently of one another C1-C20 alkylene, C6-C20 arylene, or C3-C20 heteroarylene; and $R_{11}$ to $R_{14}$ may be independently of one another hydrogen, a halogen, C4-C25 alkoxy, CHO, or NHCOOH.

In terms of having more improved physical properties, preferably, in Chemical Formulae 2 to 7 according to an exemplary embodiment of the present invention, X may be a halogen or

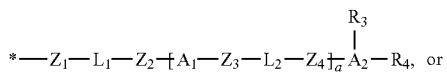

$Z_1$ and $Z_3$ may be independently of each other a single bond, —O—, —CO—, —OCO—, —NH—, or —CONH—; $Z_2$ and $Z_4$ may be independently of each other a single bond, —O—, or C2-C6 alkenylene; $L_1$ and $L_2$ may be independently of each other a single bond, C1-C10 alkylene, C2-C10 alkenylene, or C6-C12 arylene; $A_1$ may be C1-C5 alkylene, C6-C12 arylene, C1-C20 alkyl C6-C12 arylene or C3-C12 heteroarylene; $A_2$ may be a trivalent C1-C5 alkyl radical, a trivalent C6-C12 aryl radical, or a trivalent C6-C12 aryl radical or a trivalent C3-C12 heteroaryl radical substituted with C1-C12 alkyl; a may be an integer of 0 or 1; $R_1$, $R_2$, and $R_5$ may be independently of one another hydrogen, a halogen, C1-C20 alkoxy,

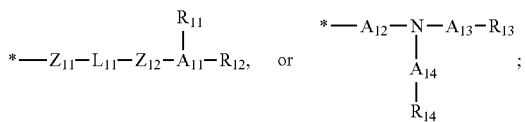

$R_3$ and $R_4$ may be independently of each other hydrogen, halogen, C4-C25 alkoxy, $Z_{11}$ may be a single bond, —O—, —OCO—, —NH—, or —CONH—; $Z_{12}$ may be a single bond, —O—, or C2-C6 alkenylene; $L_{11}$ may be a single bond, C1-C10 alkylene, C2-C10 alkenylene, or C6-C12 arylene; $A_{11}$ may be a trivalent C1-C10 alkyl radical, a trivalent C6-C12 aryl radical, or a trivalent C6-C12 aryl radical or a trivalent C3-C12 heteroaryl radical substituted with C1-C10 alkyl; $A_{12}$ to $A_{14}$ may be independently of each other C1-C10 alkylene, C6-C12 arylene, or C3-C12 heteroarylene; $R_a$, $R_b$, and $R_c$ may be independently of one another (C1-C20)alkyl; and $R_{11}$ to $R_{14}$ may be independently of one another hydrogen, a halogen, C4-C25 alkoxy, CHO, or NHCOOH.

Preferably, Chemical Formula 2 according to an exemplary embodiment of the present invention may be represented by the following Chemical Formula 11 or Chemical Formula 12:

[Chemical Formula 11]

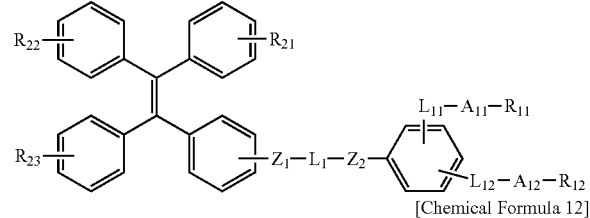

[Chemical Formula 12]

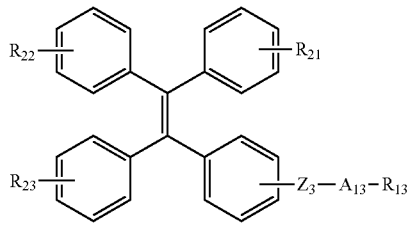

wherein
$Z_1$ to $Z_3$ are independently of one another a single bond, —O—, —OCO—, —COO—, —NH—, —CONH—, —NHCO—, C2-C30 alkenylene, or C6-C30 arylene;
$L_1$, $L_{11}$, and $L_{12}$ are independently of one another a single bond, C1-C30 alkylene, C2-C30 alkenylene, or C6-C30 arylene;
$A_{11}$ to $A_{13}$ are independently of one another C1-C30 alkylene, C6-C30 arylene, or C3-C30 heteroarylene;
$R_{11}$ to $R_{13}$ are independently of one another hydrogen, a halogen, C1-C30 alkoxy, or NHCOOH; and
$R_{21}$ to $R_{23}$ are independently of one another hydrogen, a halogen, C1-C30 alkoxy,

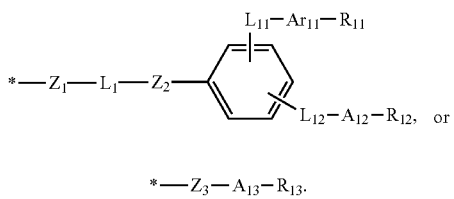

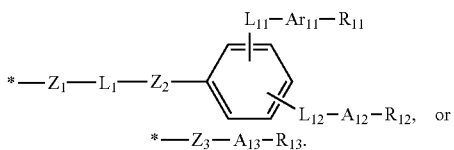

The ferroelectric fluorescent self-assembly compound represented by Chemical Formula 11 or Chemical Formula 12 according to an exemplary embodiment of the present invention has more improved light-emitting efficiency by introducing tetraphenylethene as a main skeleton and introducing one or more of

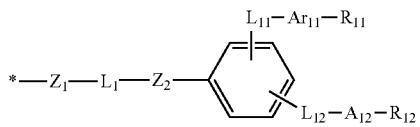

which is a substituent capable of self-assembly to the tetraphenylethene skeleton.

In addition, the tetraphenylethene compound of Chemical Formula 11 or Chemical Formula 12 has a high solubility in an organic solvent by introducing a specific substituent, in particular, a long-chain alkoxy to the end of the substituent, thereby allowing an organic electronic element to be manufactured by a solution process, and thus, the process is simplified and high-priced deposition equipment is not needed, which is thus very economical.

Preferably, in Chemical Formulae 11 and 12 according to an exemplary embodiment of the present invention, $Z_1$ may be a single bond; $Z_2$ may be C2-C20 alkenylene; $Z_3$ may be independently of each other a single bond, —O—, —NH—, —CONH—, or C6-C20 arylene; $L_1$ may be a single bond or C6-C20 arylene; $L_{11}$ and $L_{12}$ may be C2-C20 alkenylene; $A_{11}$ to $A_{13}$ may be independently of one another C6-C20 arylene; $A_{13}$ may be C1-C20 alkylene, C6-C20 arylene, or C3-C30 heteroarylene; $R_{11}$ to $R_{13}$ may be independently of one another hydrogen, C4-C30 alkoxy, or NHCOOH; and $R_{21}$ to $R_{23}$ may be independently of each other hydrogen, C1-C20 alkoxy, More preferably, the ferroelectric fluorescent self-assembly compound according to an exemplary embodiment of the present invention may be represented by the following Chemical Formula 2-1:

[Chemical Formula 2-1]

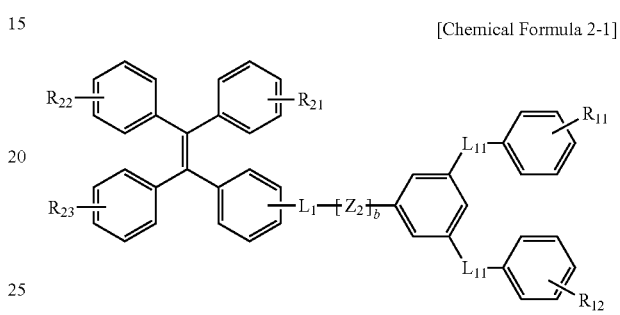

wherein
$L_1$ is C6-C30 arylene;
$Z_2$ is C2-C20 alkenylene;
$L_{11}$ is C2-C10 alkenylene;
b is an integer of 0 or 1;
$R_{11}$ and $R_{12}$ are independently of each other C1-C30 alkoxy; and
$R_{21}$ to $R_{23}$ are independently of one another hydrogen, a halogen, C1-C30 alkoxy, or

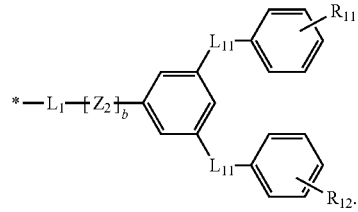

Preferably, Chemical Formula 2 according to an exemplary embodiment of the present invention may be represented by the following Chemical Formula 13 or Chemical Formula 14:

[Chemical Formula 13]

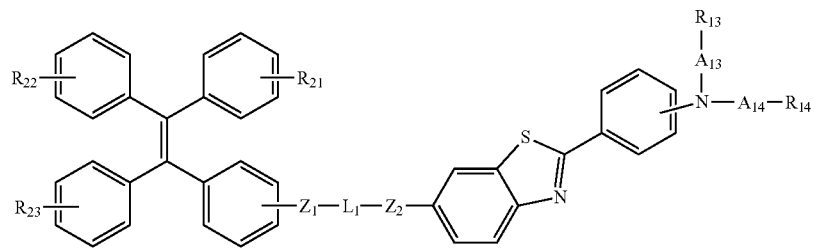

-continued

[Chemical Formula 14]

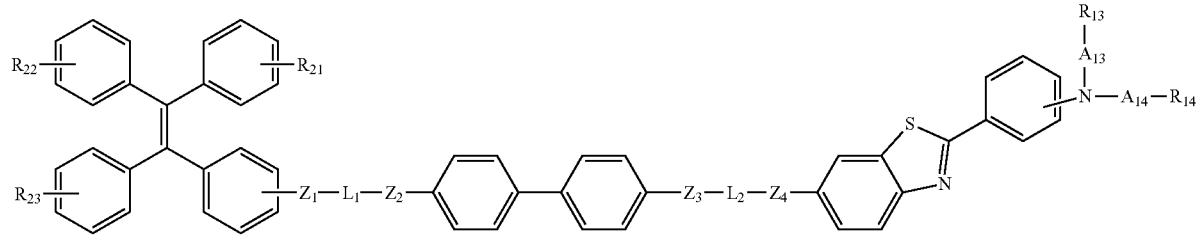

wherein
$Z_1$ to $Z_4$ are independently of one another a single bond, —O—, —OCO—, —COO—, —NH—, —CONH—, —NHCO—, or C2-C30 alkenylene;
$L_1$ and $L_2$ are a single bond, C1-C30 alkylene, C2-C30 alkenylene, or C6-C30 arylene;
$A_{13}$ and $A_{14}$ are independently of each other C6-C30 arylene;
$R_{13}$ and $R_{14}$ are independently of each other hydrogen, a halogen, C1-C30 alkoxy, CHO, or NHCOOH; and
$R_{21}$ to $R_{23}$ are independently of one another hydrogen, a halogen, C1-C30 alkoxy, or

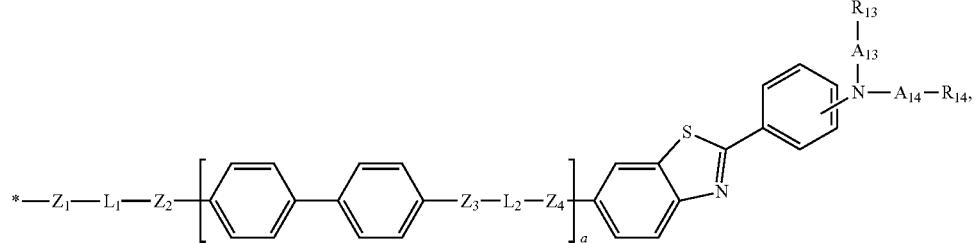

in which a is an integer of 0 or 1.
More preferably, in Chemical Formula 13 or Chemical Formula 14 according to an exemplary embodiment of the present invention, $Z_1$ to $Z_4$ may be independently of one another a single bond, —O—, or —OCO—; $L_1$ and $L_2$ may be independently of each other a single bond or C2-C20 alkenylene; $A_{13}$ and $A_{14}$ may be independently of each other C6-C12 arylene; $R_{13}$ and $R_{14}$ may be independently of each other hydrogen, a halogen, CHO, or NHCOOH; $R_{21}$ to $R_{23}$ may be independently of each other hydrogen, C1-C30 alkoxy, or

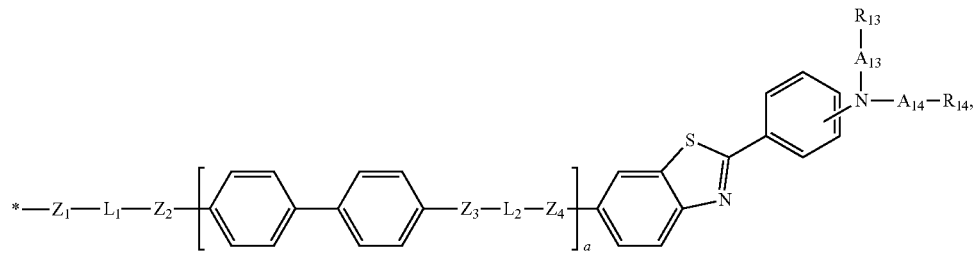

in which a may be an integer of 0 or 1, and still more preferably, $Z_1$ to $Z_4$ may be independently of one another a single bond, —O—, or —OCO—; $L_1$ and $L_2$ may be independently of each other a single bond or C2-C6 alkenylene; $A_{13}$ and $A_{14}$ may be independently of each other C6-C12 arylene; $R_{13}$ and $R_{14}$ may be independently of each other hydrogen, a halogen, CHO, or NHCOOH; and $R_{21}$ to $R_{23}$ may be independently of one another hydrogen or

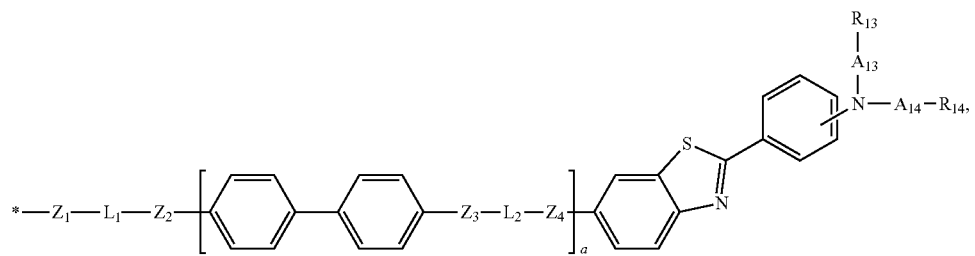
in which a may be an integer of 0 or 1.
Specifically, the ferroelectric fluorescent self-assembly compound according to an exemplary embodiment of the present invention may be selected from the following compounds, but is not limited thereto:
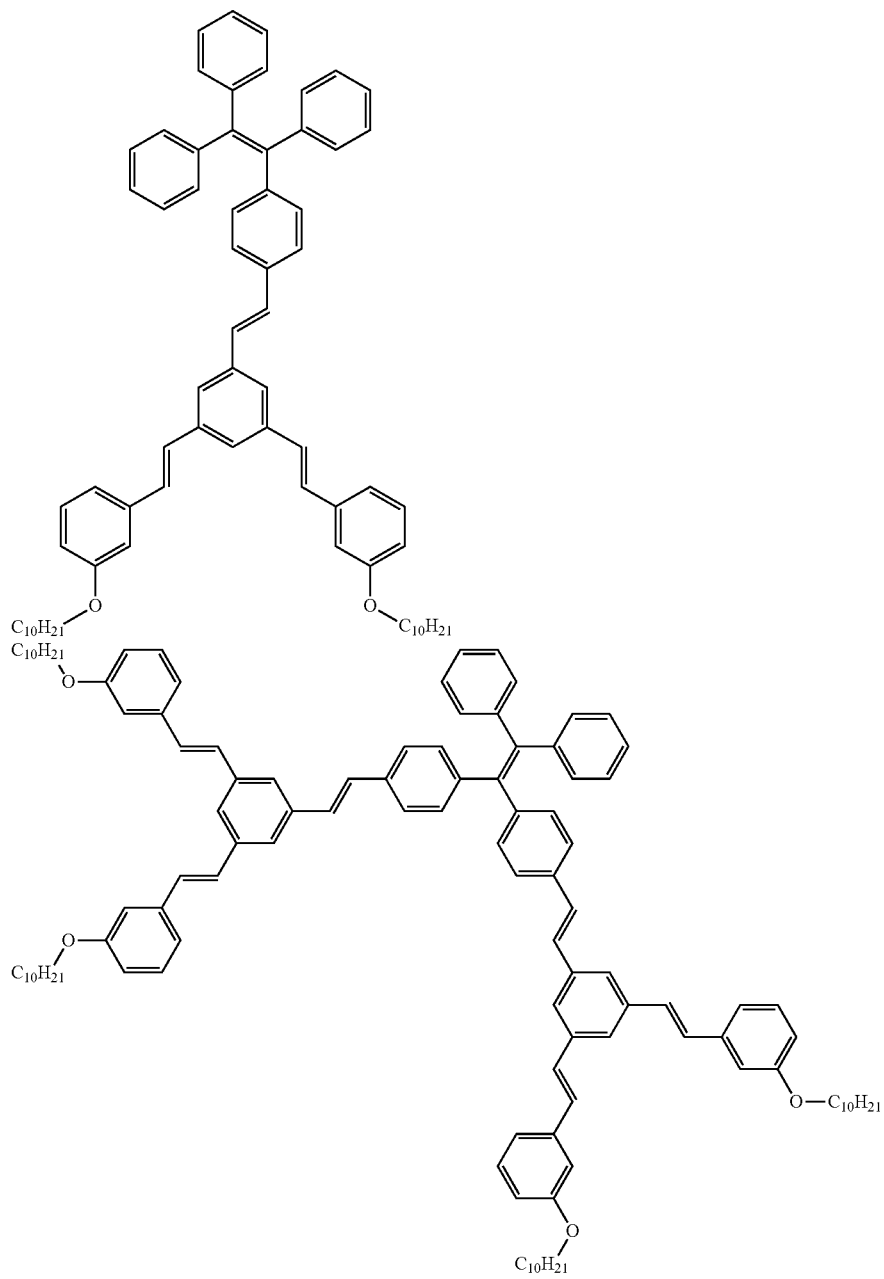

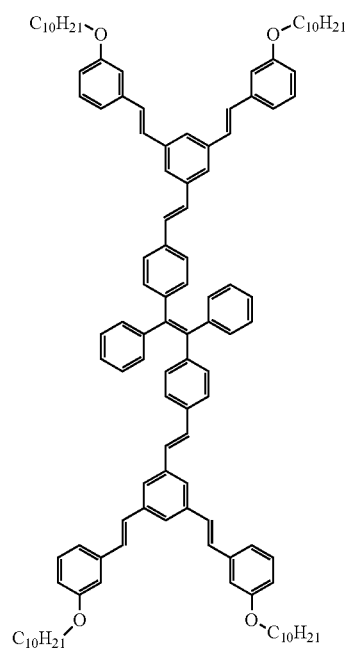
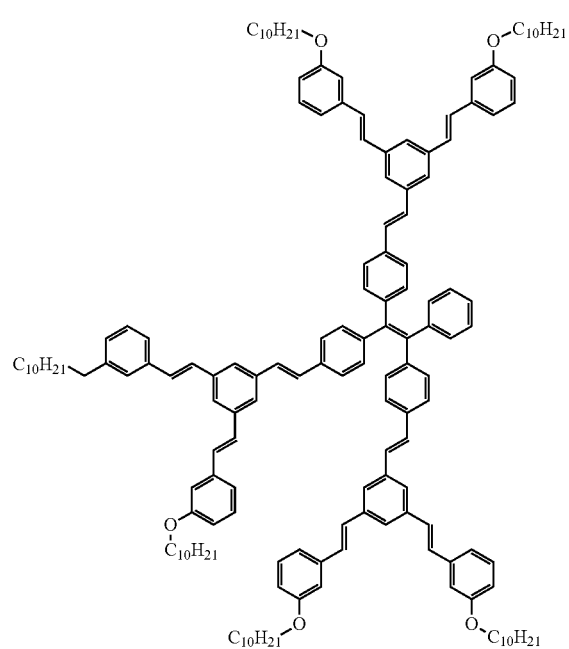
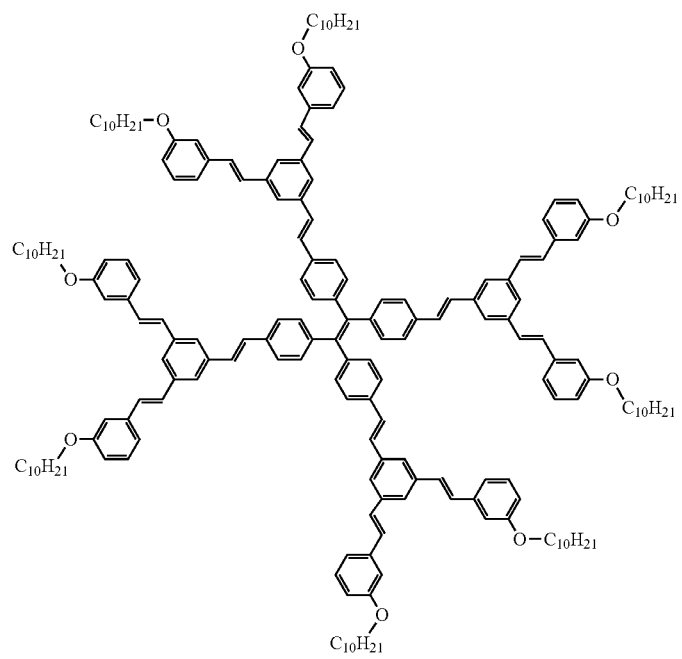

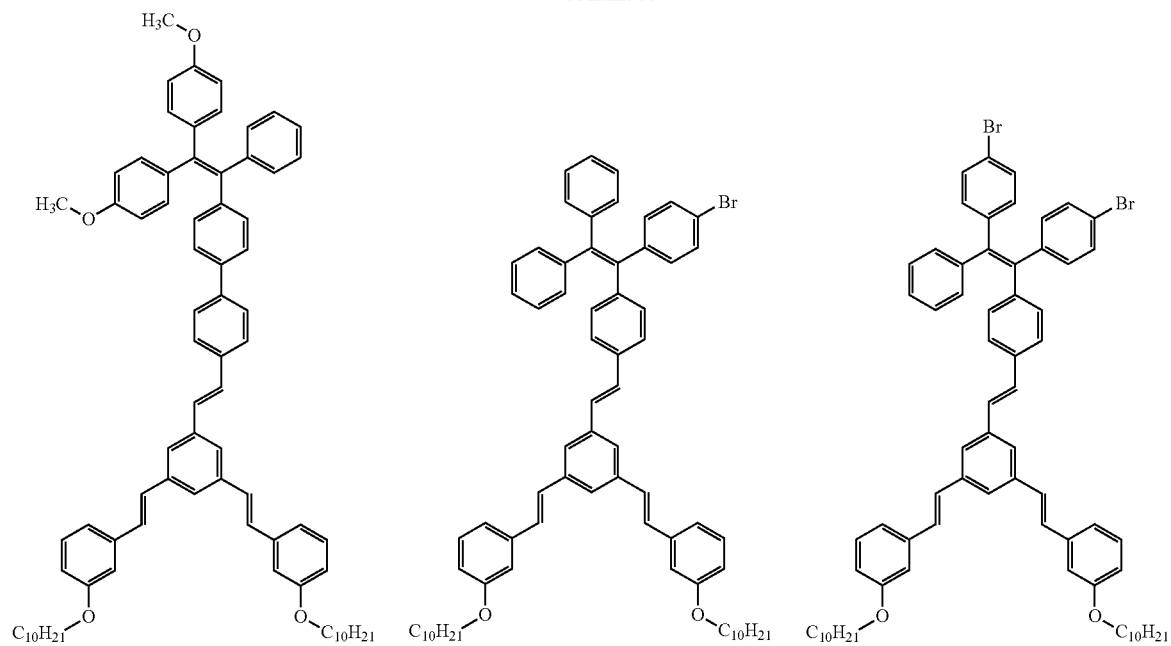
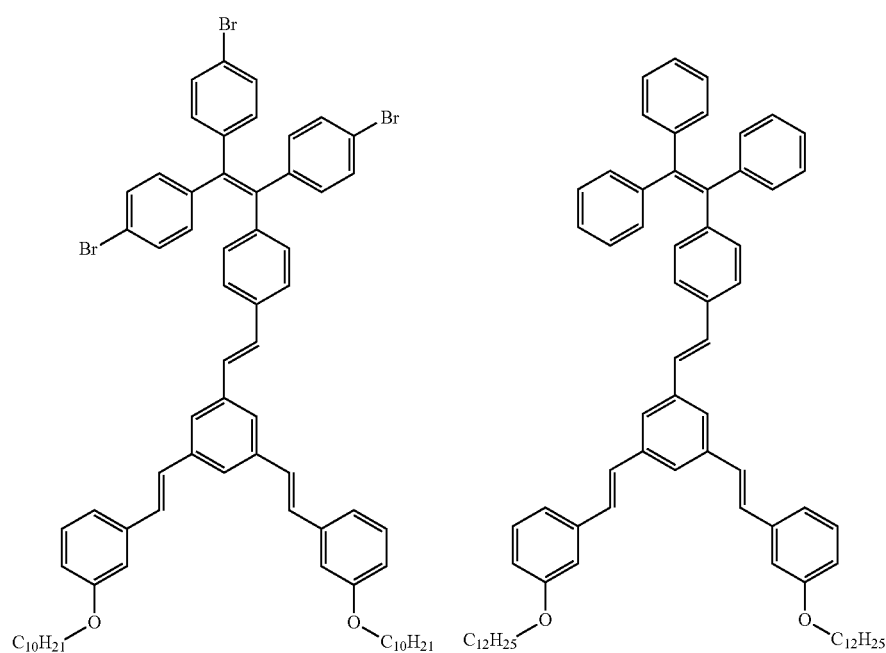

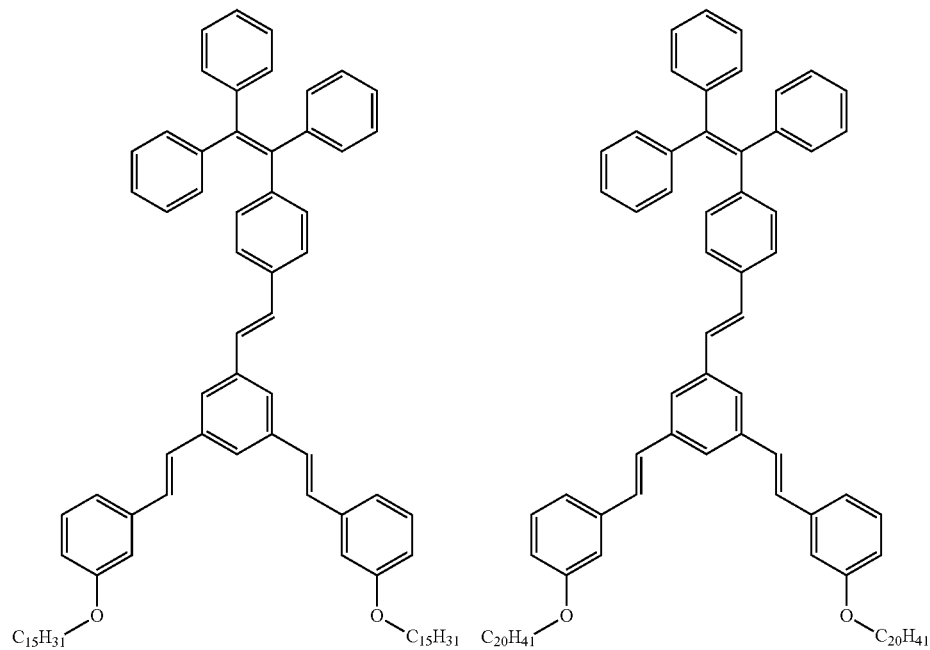
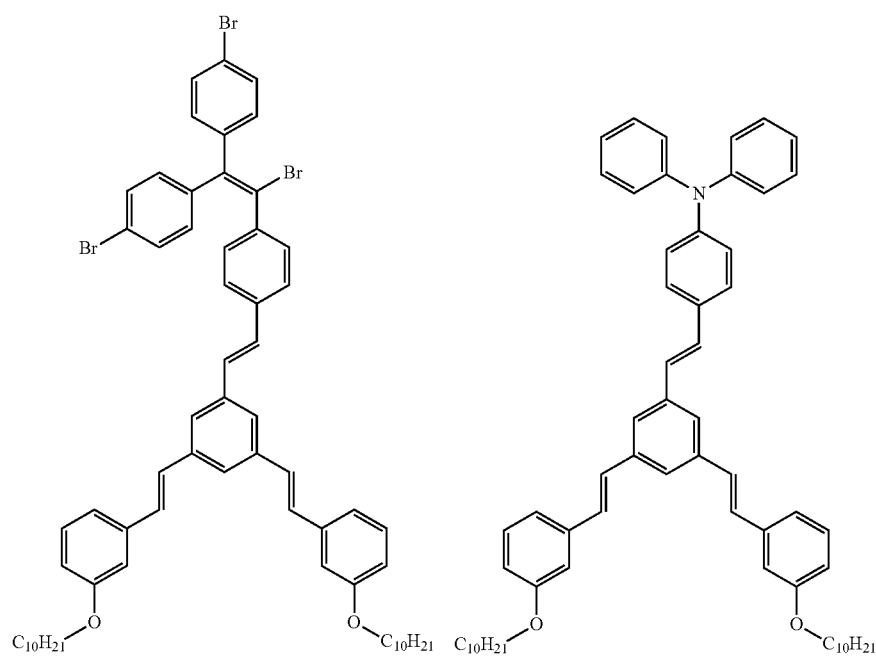

-continued
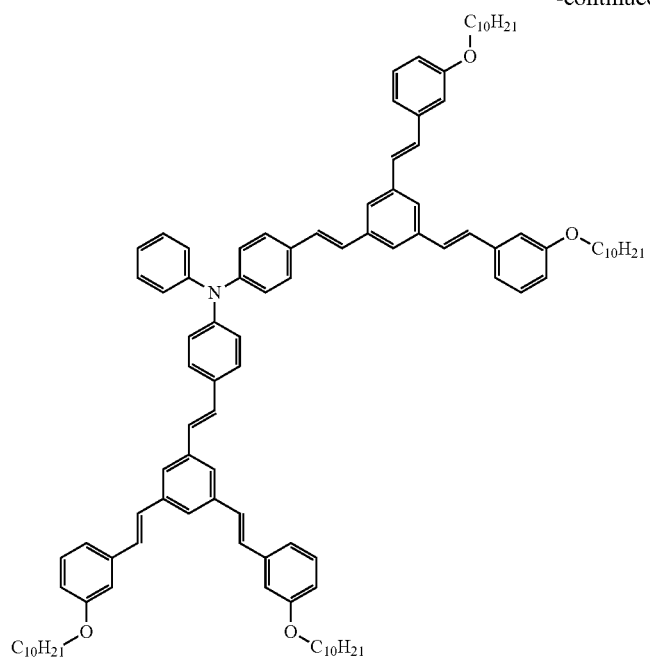
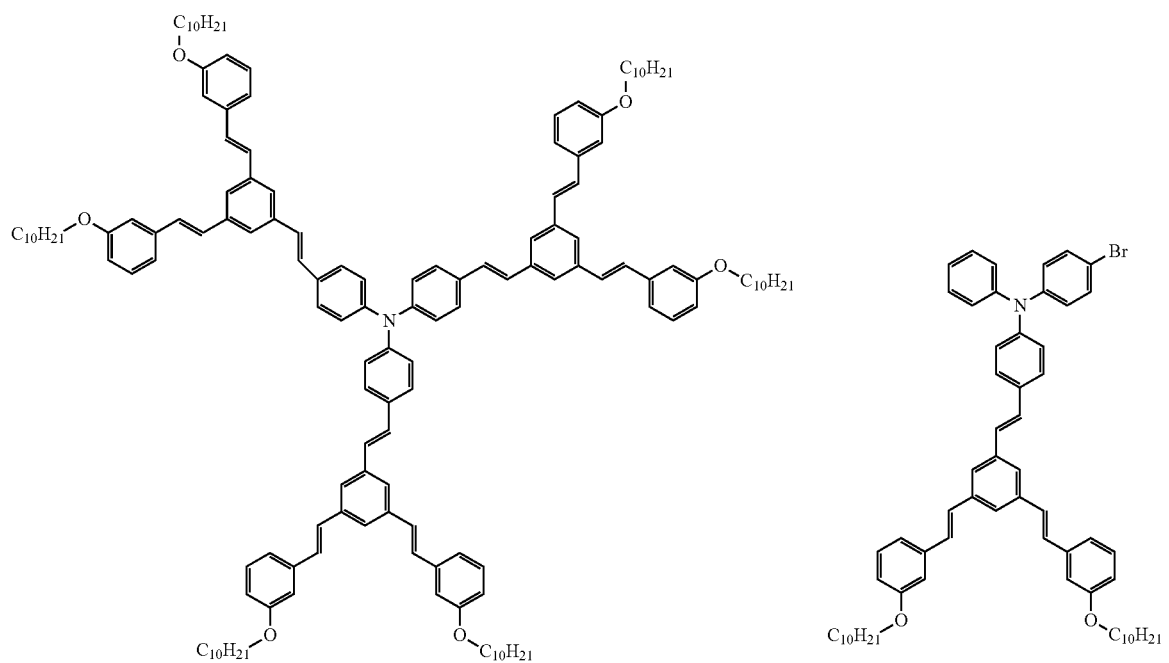

-continued
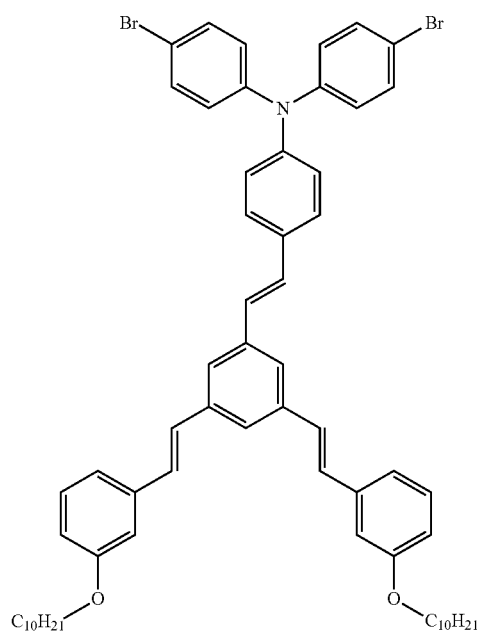
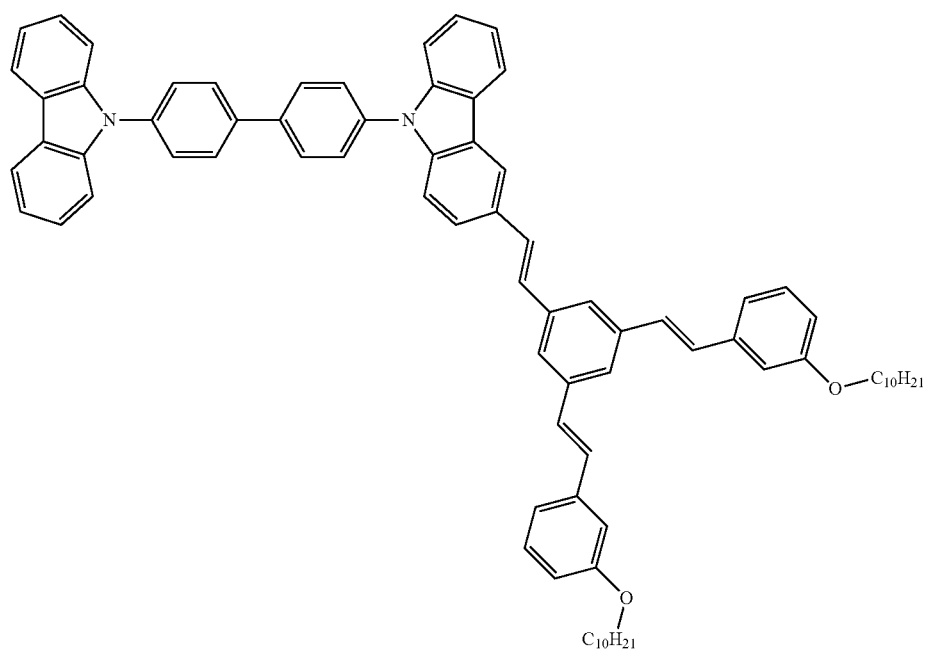

-continued
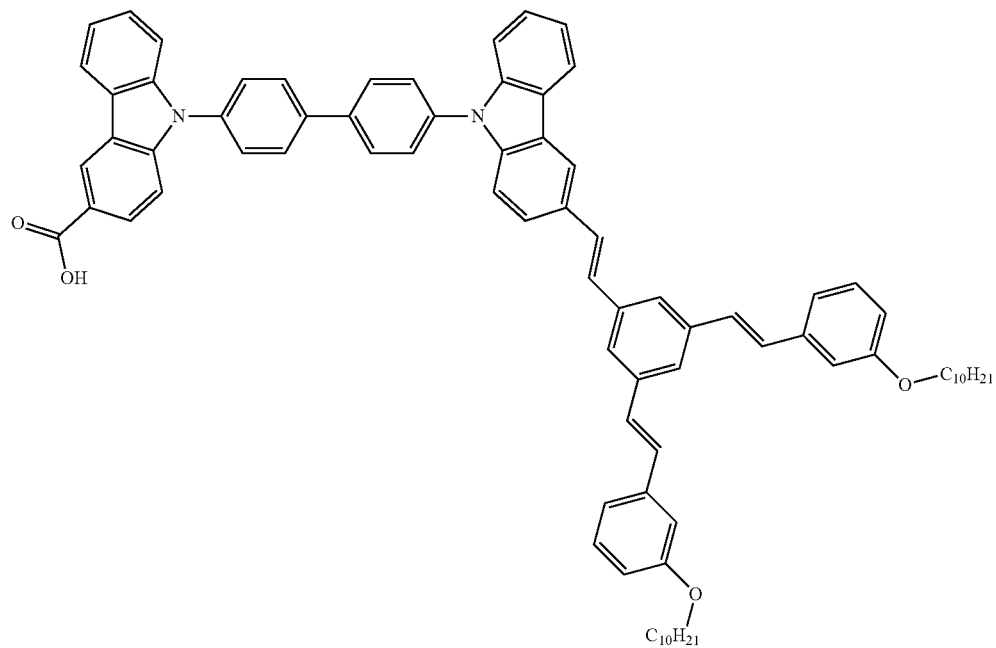
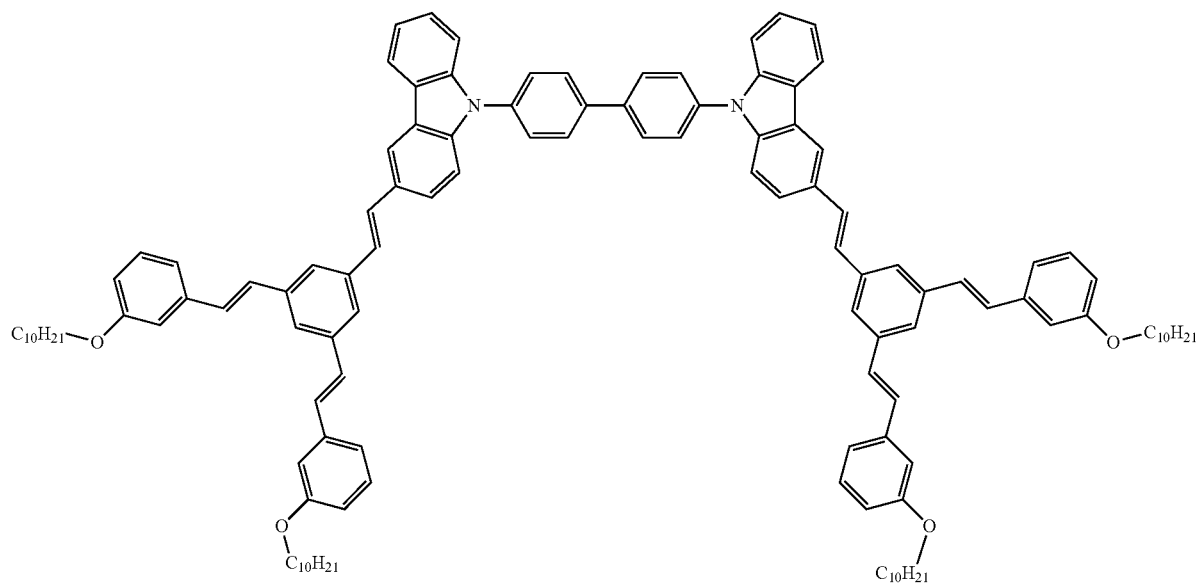

-continued
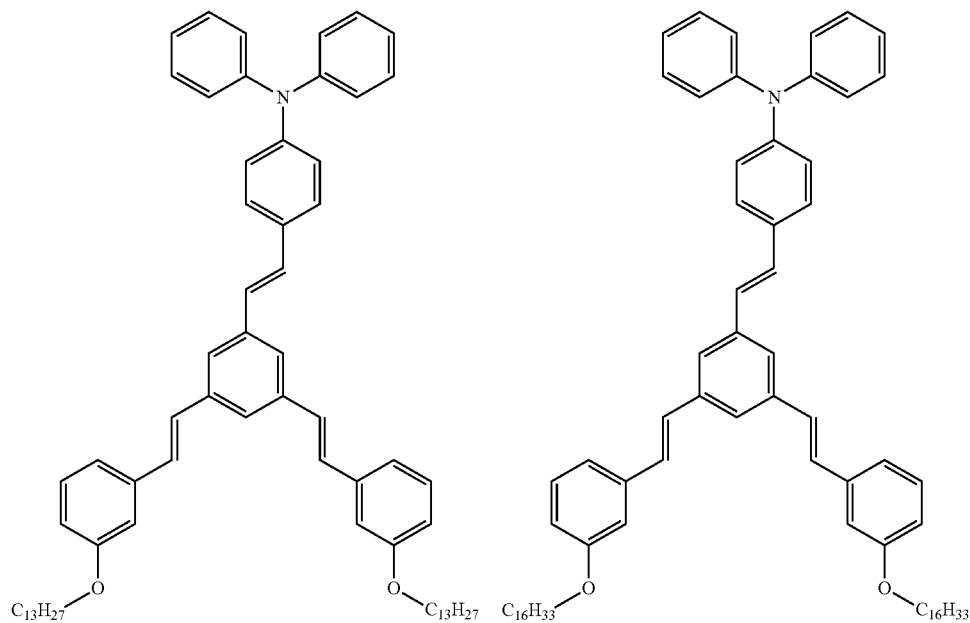
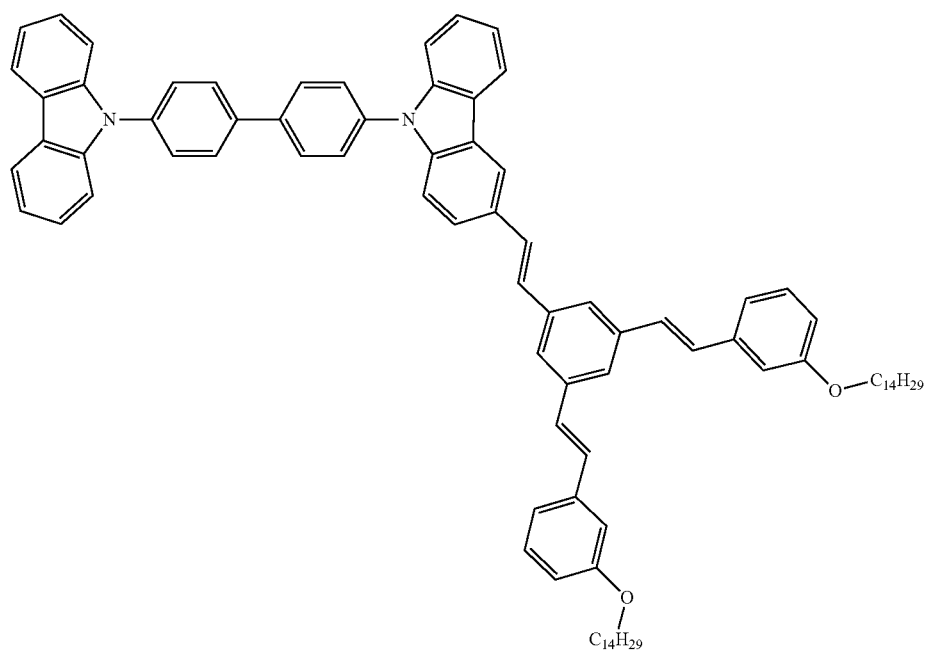

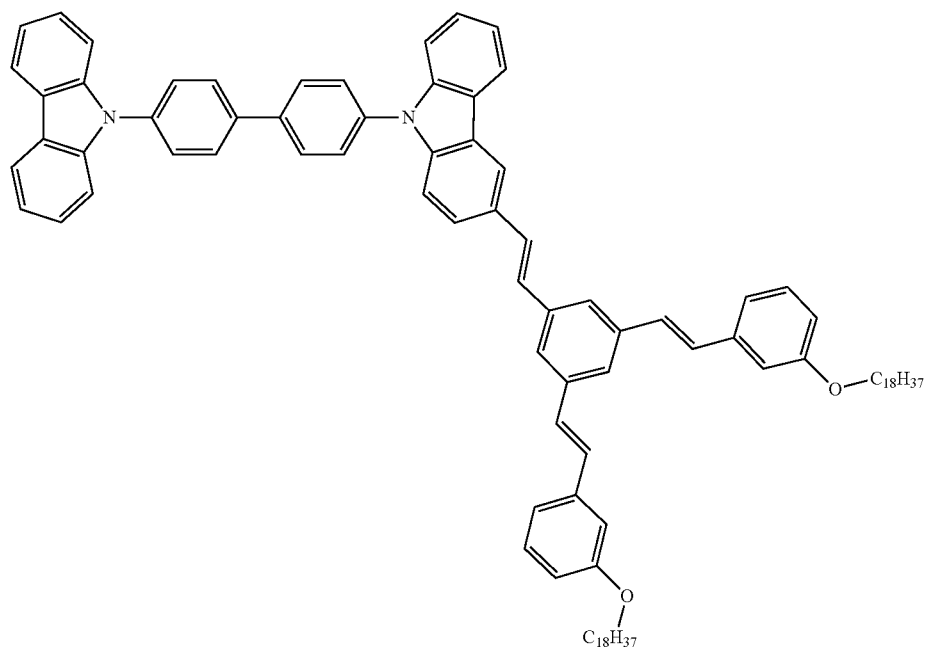
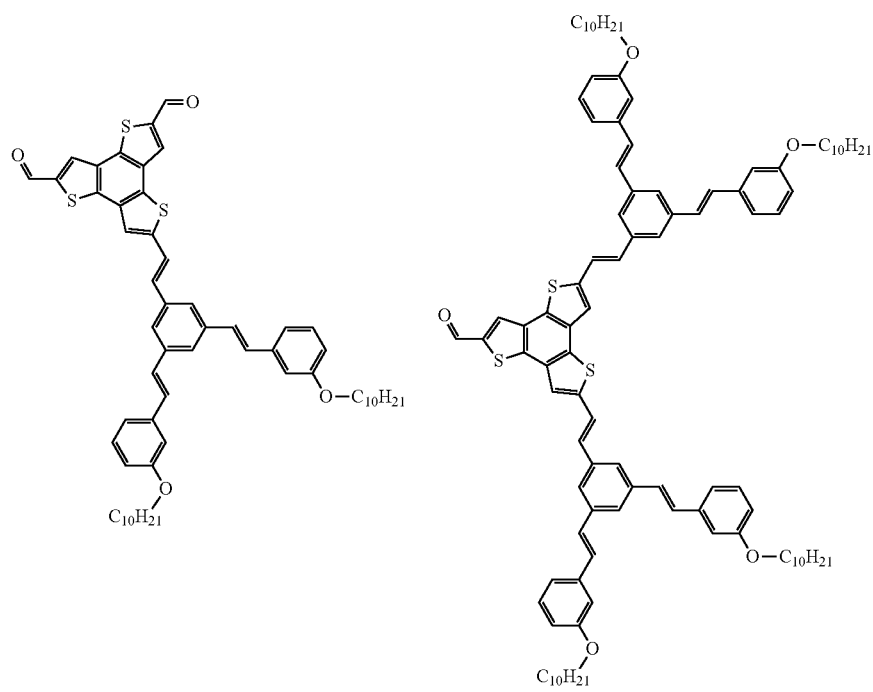

-continued
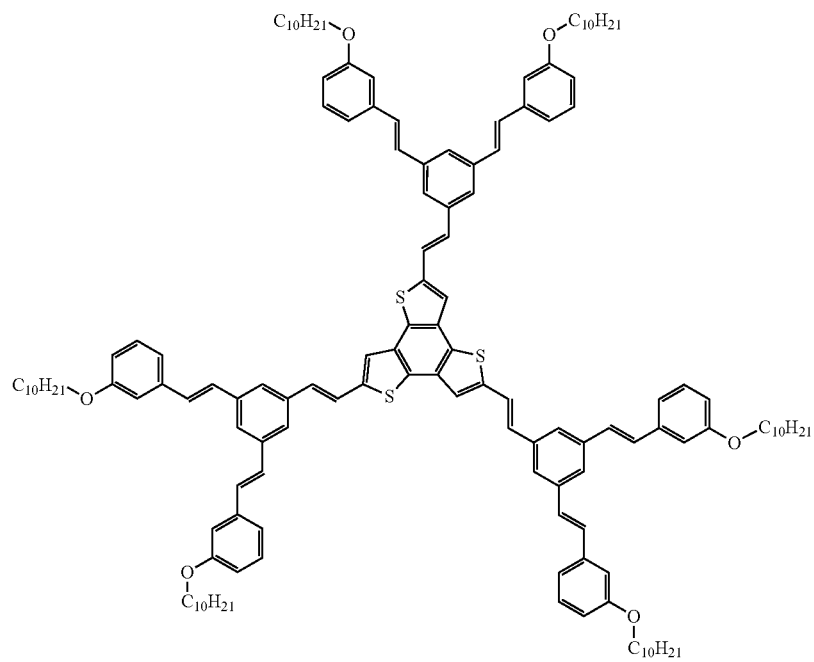
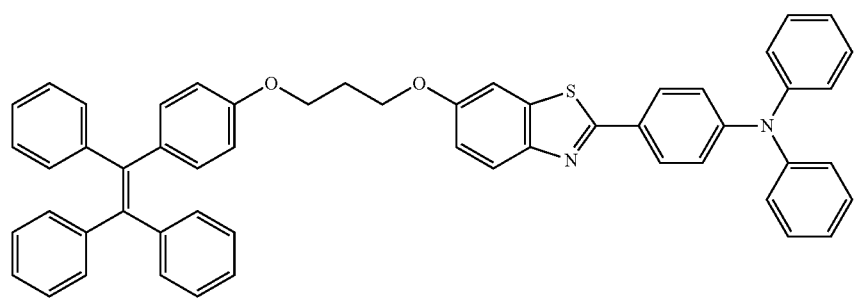 [SMILES: c1ccc(C(=C(c2ccccc2)c2ccc(OCCCOc3ccc4nc(-c5ccc(N(c6ccccc6)c6ccccc6)cc5)sc4c3)cc2)c2ccccc2)cc1]
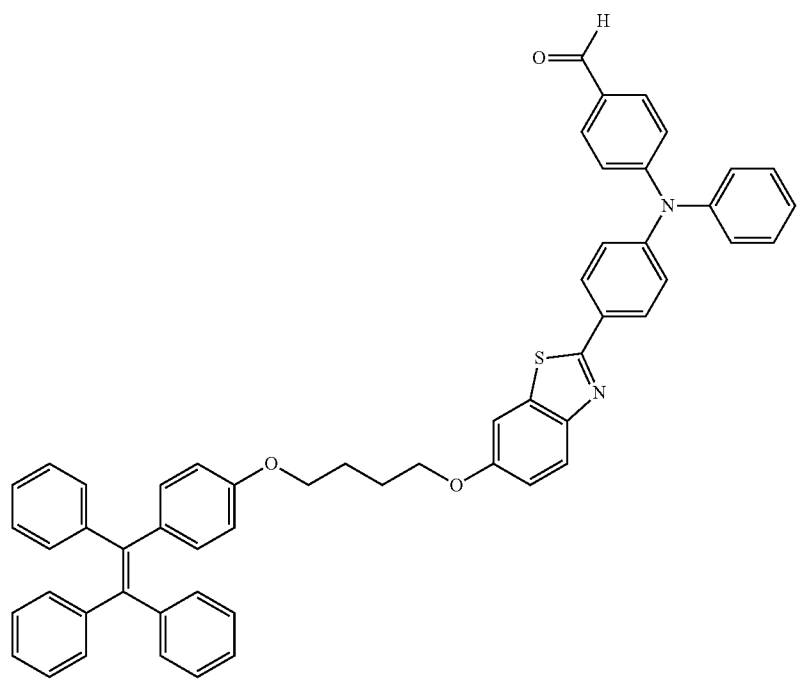 [SMILES: O=Cc1ccc(N(c2ccccc2)c2ccc(-c3nc4ccc(OCCCCOc5ccc(C(=C(c6ccccc6)c6ccccc6)c6ccccc6)cc5)cc4s3)cc2)cc1]

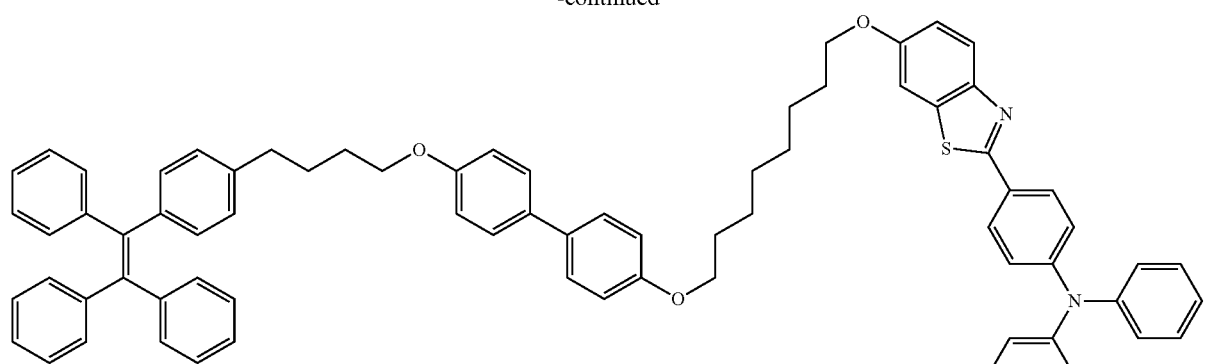
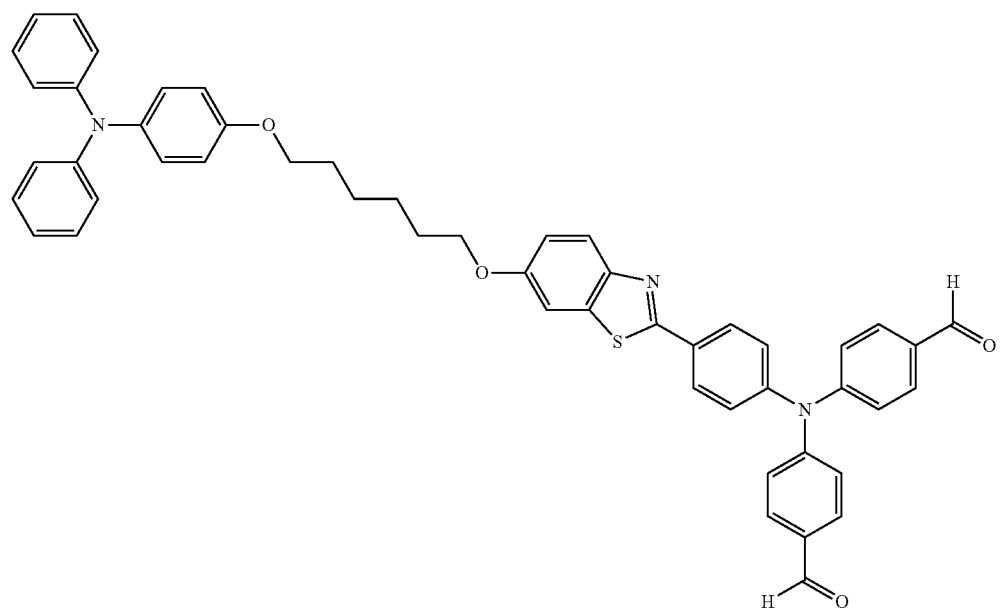
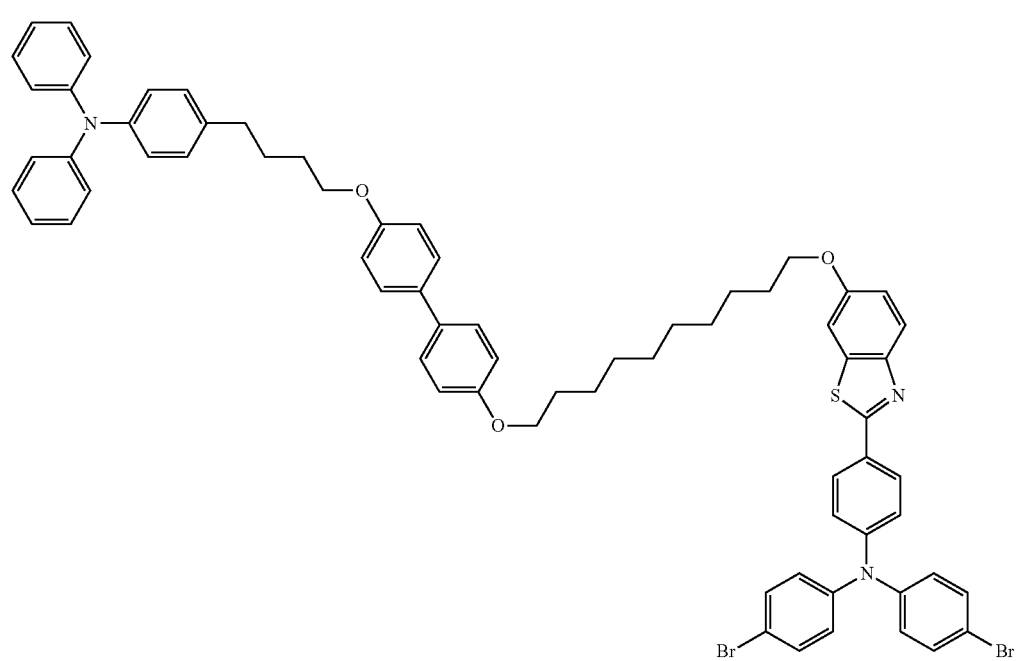

87
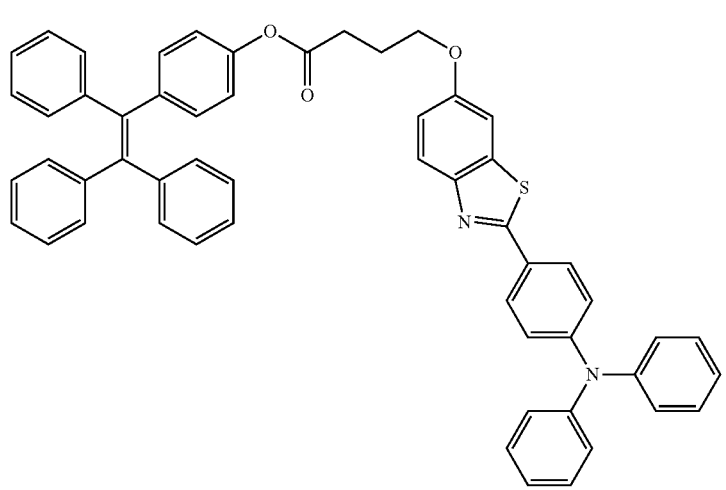
88
-continued
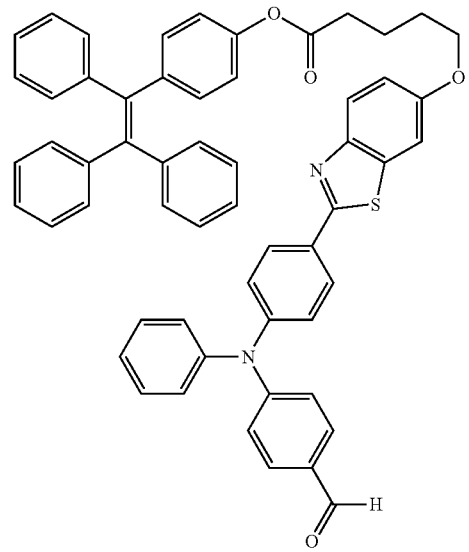
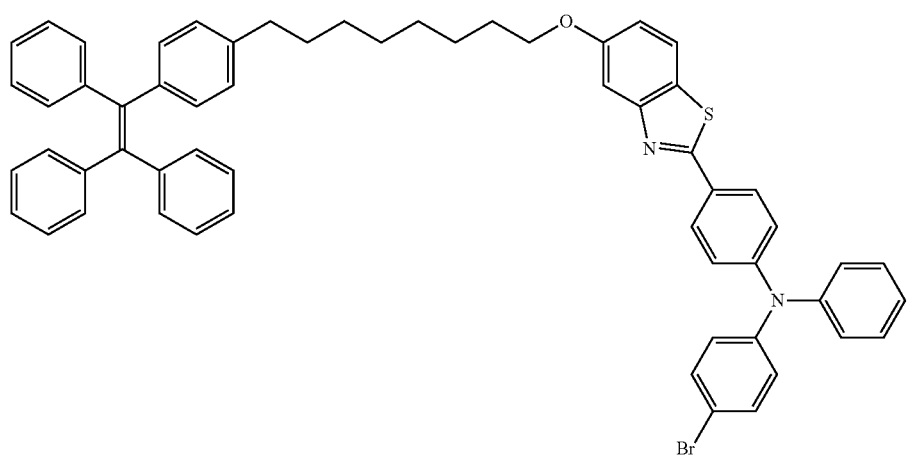
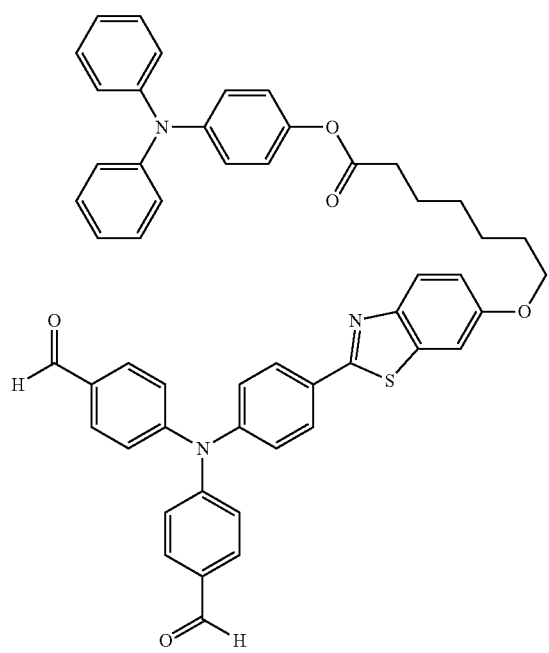

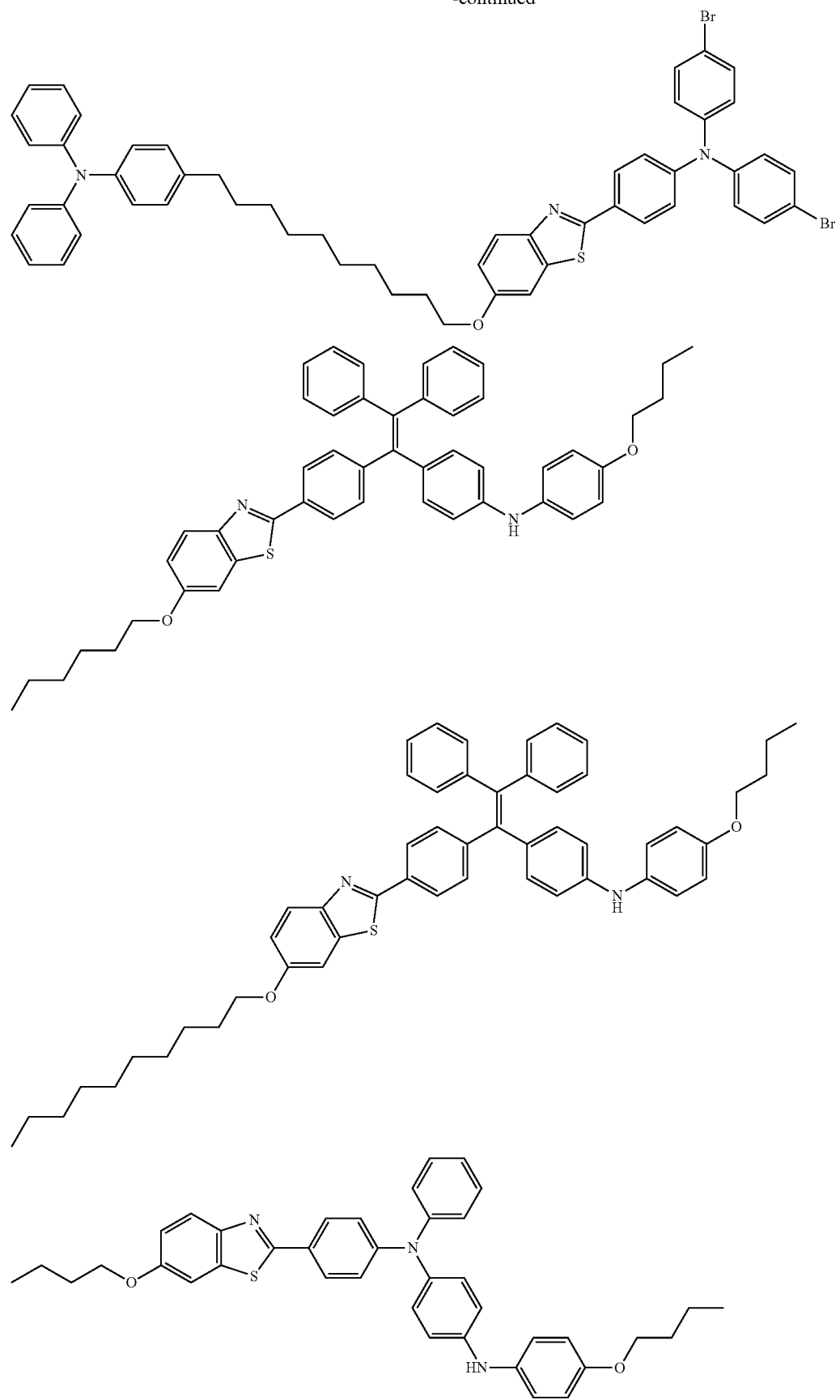

-continued
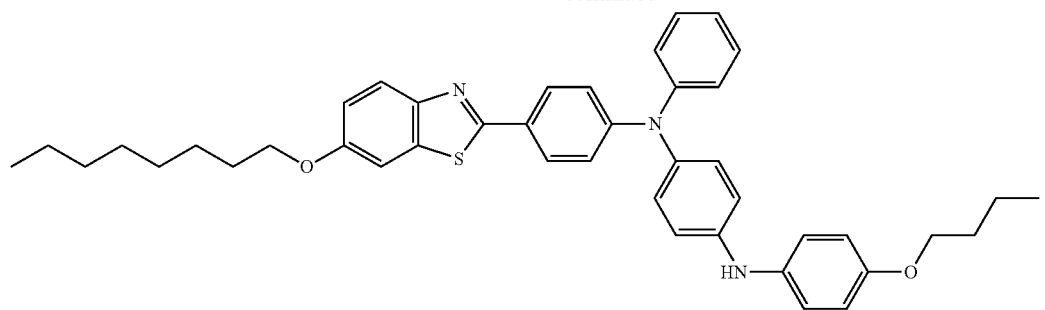
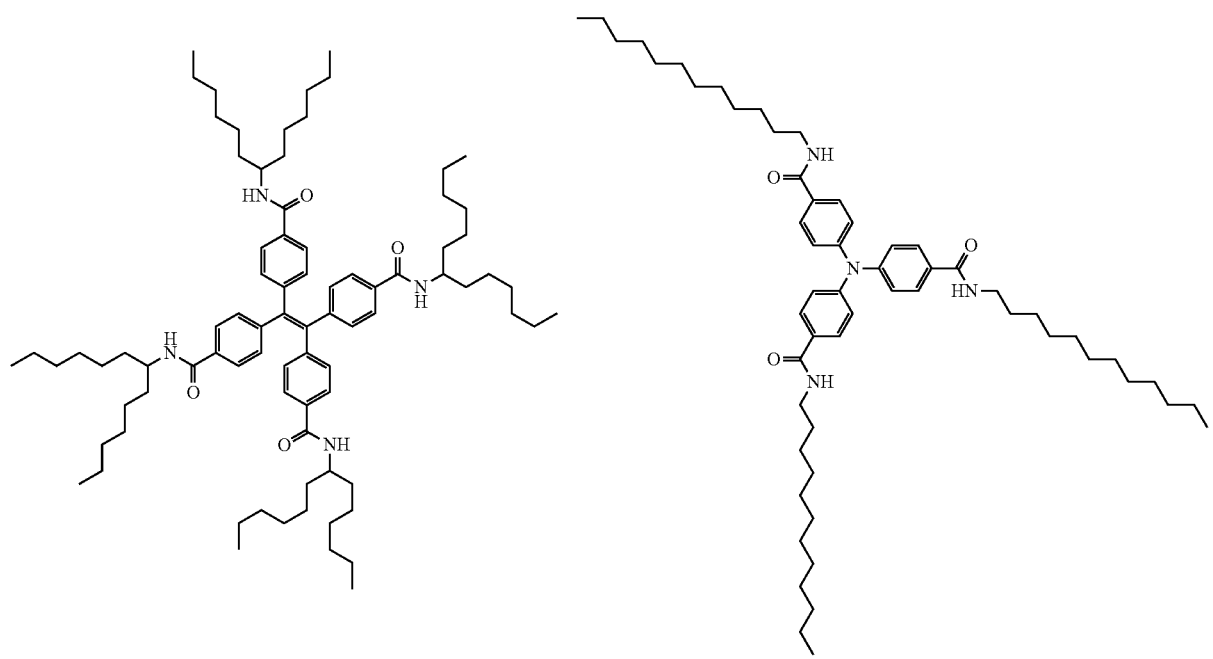
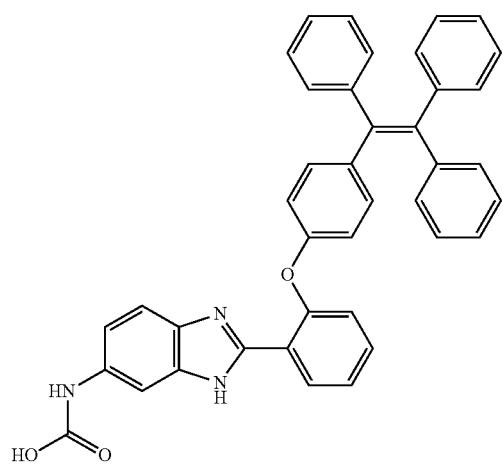

-continued
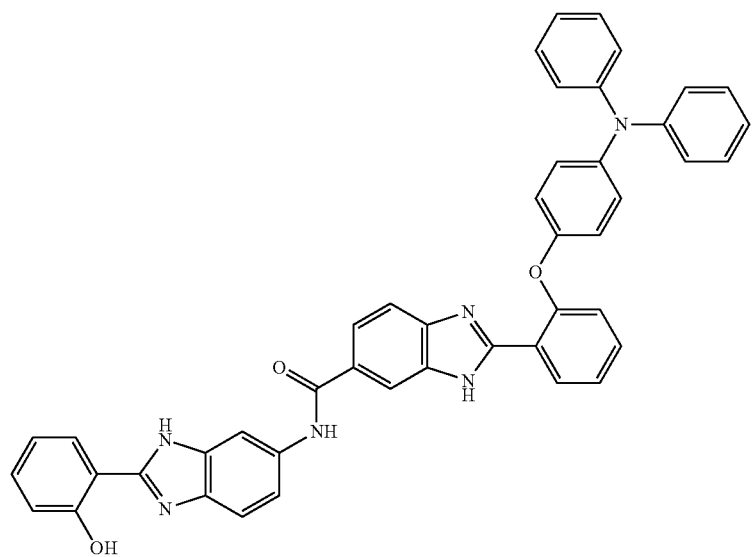
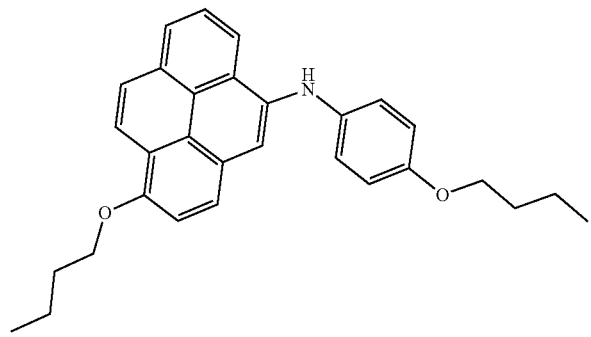
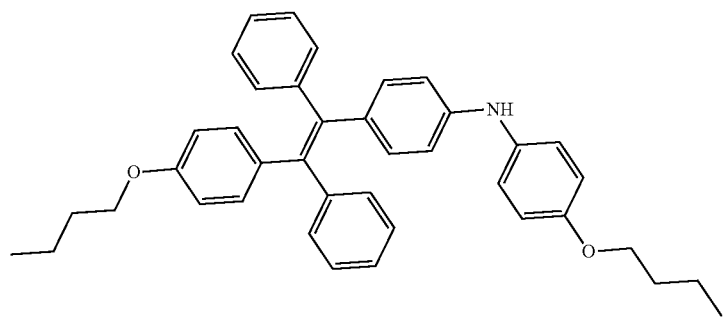

-continued
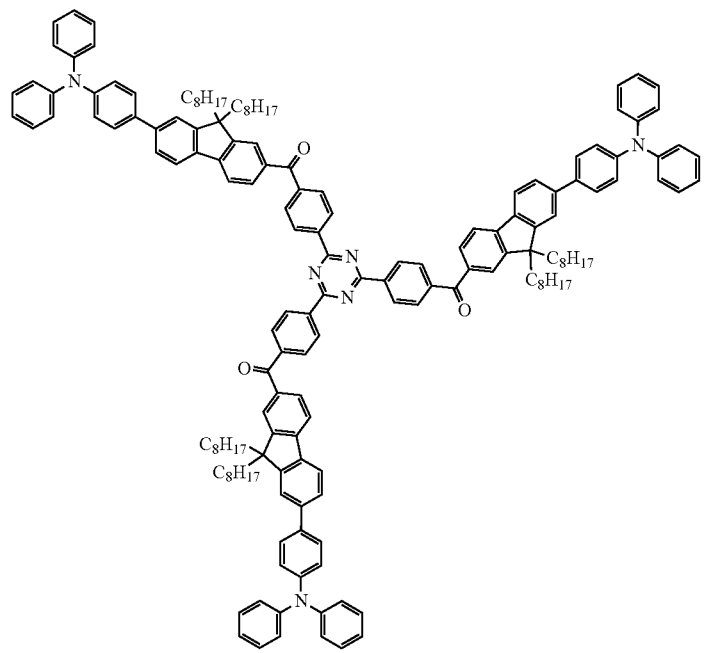
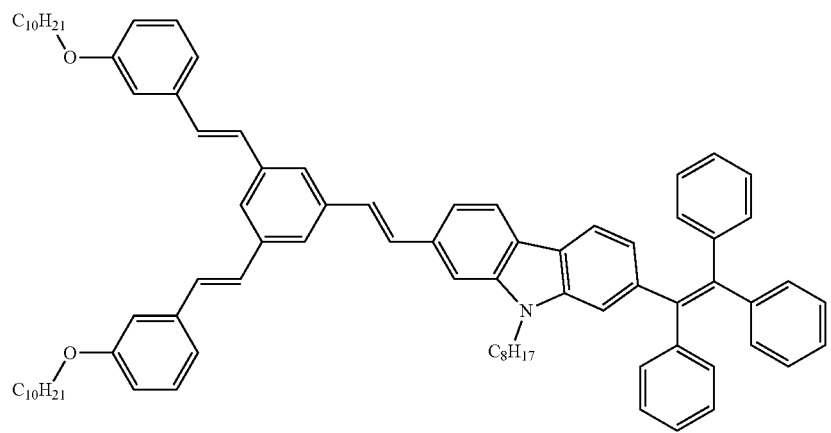

-continued

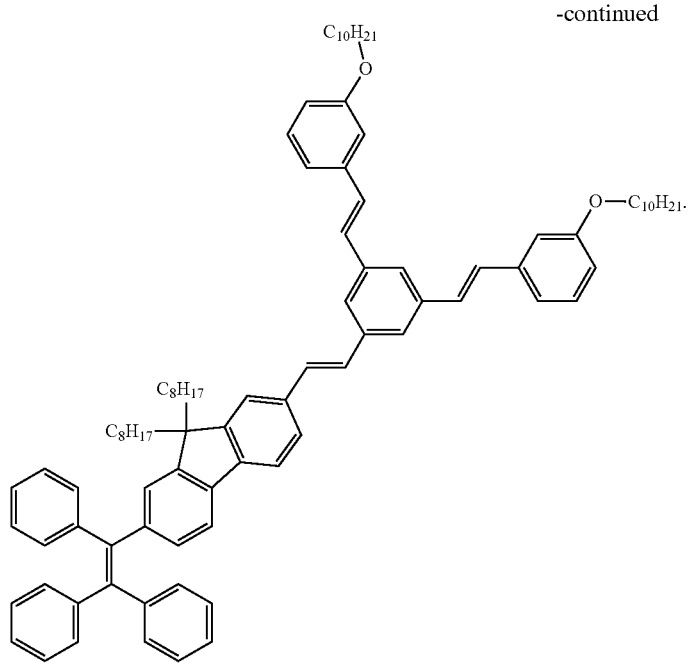

The ferroelectric fluorescent self-assembly compound according to an exemplary embodiment of the present invention may be synthesized by all methods which may be recognized by a person skilled in the art, and for example, a triphenylethene skeleton may be prepared by a method of the following Reaction Formula 1:

[Reaction Formula 1]

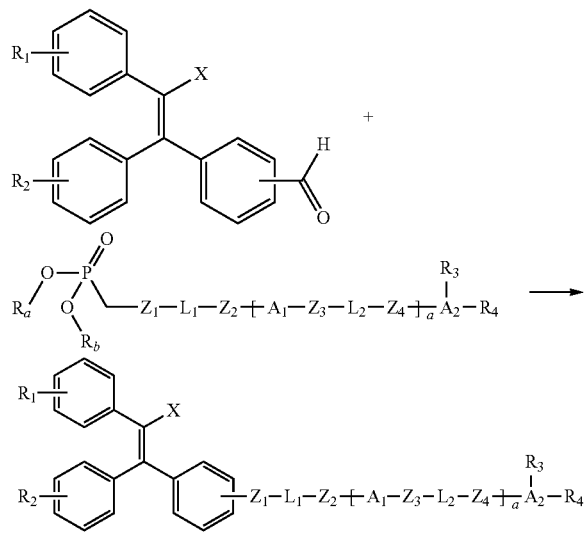

wherein $R_a$ and $R_b$ is alkyl, X, $Z_1$ to $Z_4$, $L_1$ and $L_2$, $A_1$ and $A_2$, a, and $R_1$ to $R_4$ are as defined in Chemical Formula 1.

The ferroelectric fluorescent self-assembly compound according to an exemplary embodiment of the present invention may be prepared by changing reaction conditions according to a common preparation method.

It is preferred that the preparation method of the ferroelectric fluorescent self-assembly compound according to an exemplary embodiment of the present invention is carried out in an organic solvent, but the reaction may be also carried out in a melted state without using a solvent, of course. The organic solvent is not limited as long as it may completely dissolve reactants, but a specific example thereof may be toluene, methanol, ethanol, benzene, n-heptane, tetrahydrofuran (THF), chloroform, or a mixed solvent thereof.

In addition, the present invention provides an organic electronic element including the ferroelectric fluorescent self-assembly compound of the present invention represented by Chemical Formula 1.

The organic electronic element according to an exemplary embodiment of the present invention may be an organic solar cell, an organic thin film transistor, a capacitor, an organic light-emitting element, or an organic sensor.

Preferably, the ferroelectric fluorescent self-assembly compound of the present invention may be included in an organic layer of the organic electronic element of the present invention.

Preferably, the organic electronic element of the present invention may be an organic light-emitting element, and more preferably, in the organic electronic element, the ferroelectric fluorescent self-assembly compound of the present invention may be included in the emitting layer.

Specifically, the organic light-emitting element according to an exemplary embodiment of the present invention includes a first electrode; a second electrode; and one or more organic layers interposed between the first electrode and the second electrode, wherein the organic layer may include the ferroelectric fluorescent self-assembly compound of the present invention.

More preferably, the ferroelectric fluorescent self-assembly compound of the present invention may be included the emitting layer of the organic light-emitting element.

The organic light-emitting element according to an exemplary embodiment of the present invention may be manufactured by a method possible within the range which a person skilled in the art may recognize, of course.

The ferroelectric fluorescent self-assembly compound represented by Chemical Formula 1 according to an exemplary embodiment of the present invention may be applied to various organic light-emitting elements, and the organic light-emitting elements may be used in a device selected from a flat panel display device, a flexible display device, a monochromatic or white flat lighting device, a monochromatic or white flexible lighting device, and the like, but are not limited thereto.

Hereinafter, one embodiment of the organic light-emitting element will be described in detail.

The organic light-emitting element (OLED) according to an exemplary embodiment of the present invention may include a first electrode (EL1), a hole transport region (HTR), an emitting layer (EML), an electron transport region (ETR), and a second electrode (EL2).

The first electrode (EL1) has conductivity. The first electrode (EL1) may be a pixel electrode or a positive electrode. The first electrode (EL1) may be a transmissive electrode, a semi-transmissive electrode, or a reflective electrode. When the first electrode (EL1) is a transmissive electrode, the first electrode (EL1) may include a transparent metal oxide, as an example, indium tin oxide (ITO), indium zinc oxide (IZO), zinc oxide (ZnO), indium tin zinc oxide (ITZO), and the like.

When the first electrode (EL1) is a semi-transmissive electrode or a reflective electrode, the first electrode (EL1) may include Ag, Mg, Cu, Al, Pt, Pd, Au, Ni, Nd, Ir, Cr, Li, Ca, LiF/Ca, LiF/Al, Mo, Ti, or a compound or mixture thereof (for example, a mixture of Ag and Mg).

In addition, the first electrode (EL1) may have a multilayer structure including a reflective film or a semi-transmissive film formed of the material and a transparent conductive film formed of indium tin oxide (no), indium zinc oxide (IZO), zinc oxide (ZnO), indium tin zinc oxide (ITZO), and the like. As an example, the first electrode (EL1) may have a three-layer structure of ITO/Ag/ITO, but is not limited thereto.

The first electrode (EL1) may have a thickness of, as an example, 1000 Å to 10000 Å or 1000 Å to 3000 Å.

The hole transport region (HTR) is provided on the first electrode (EL1). The hole transport region (HTR) may include at least one of a hole injection layer (HIL), a hole transport layer (HTL), a hole buffer layer, and an electron blocking layer (EBL).

The hole transport region (HTR) may have a monolayer structure composed of a single material, a monolayer structure composed of a plurality of different materials from each other, or a multilayer structure having a plurality of layers composed of a plurality of different materials from each other. As an example, the hole transport region (HTR) may have a monolayer structure of a hole injection layer (HIL) or a hole transport layer (HTL), or may have a monolayer structure composed of a hole injection material and a hole transport material. In addition, the hole transport region (HTR) may have a monolayer structure composed of a plurality of different materials from each other, or may have a structure of hole injection layer (HIL)/hole transport layer (HTL), hole transport layer (HIL)/hole transport layer (HTL)/hole buffer layer, hole injection layer (HIL)/hole buffer layer, hole transport layer (HTL)/hole buffer layer, or hole injection layer (HIL)/hole transport layer (HTL)/electron blocking layer (EBL), stacked from the first electrode (EL1) in the order, but is not limited thereto.

The hole transport region (HTR) may be formed using various methods such as a vacuum deposition method, a spin coating method, a casting method, a Langmuir-Blodgett method, an inkjet printing method, a laser printing method, and a laser induced thermal imaging (LITI) method.

An example of the hole injection layer (HIL) may include phthalocyanine compounds such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N, -(2-naphthyl)-N-phenylamino}-triphenylamine (2-TNATA), poly(3,4-ethylenedioxythiophene)/Poly(4-styrenesulfonate) (PEDOT/PSS), polyaniline/dodecylbenzenesulfonic acid (PANI/DBSA), polyaniline/camphor sulfonic acid (PANI/CSA), (polyaniline)/poly(4-styrenesulfonate) (PANI/PSS), N,N'-di(naphthalene-1-yl)-N,N'-diphenyl-benzidine (NPD), polyetherketone including triphenylamine (TPAPEK), 4-isopropyl-4'-methyldiphenyliodonium tetrakis(pentafluorophenyl)borate], dipyrazino[2,3-f:2',3'-h]quinoxaline-2,3,6,7,10,11-hexacarbonitrile (HAT-CN), and the like.

An example of the hole transport layer (HTL) may include carbazone-based derivatives such as N-phenylcarbazole and polyvinylcarbazole, fluorene-based derivatives, triphenylamine-based derivatives such as N,N'-bis(3-methylphenyl)-N,N'-diphenyl-[1,1-biphenyl]-4,4'-diamine (TPD) and 4,4',4"-tris(N-carbazolyl)triphenylamine (TCTA), N,N'-di(naphthalene-1-yl)-N,N'-diphenyl-benzidine (NPD), 4,4'-Cyclohexylidene bis[N,N-bis(4-methylphenyl)benzenamine] (TAPC), 4,4'-Bis[N,N'-(3-tolyl)amino]-3,3'-dimethylbiphenyl (HMTPD), and the like.

The electron blocking layer (EBL) may include common materials known in the art. An example of the electron blocking layer (EBL) may include carbazone-based derivatives such as N-phenylcarbazole and polyvinylcarbazole, fluorene-based derivatives, triphenylamine-based derivatives such as N,N'-bis(3-methylphenyl)-N,N'-diphenyl[1,1-biphenyl]-4,4'-diamine (TPD) and 4,4',4"-tris(N-carbazolyl)triphenylamine (TCTA), N,N'-di(naphthalene-1-yl)-N,N'-diphenyl-benzidine (NPD), 4,4'-Cyclohexylidene bis[N,N-bis(4-methylphenyl)benzenamine] (TAPC), 4,4'-Bis[N,N'-(3-tolyl)amino]-3,3'-dimethylbiphenyl (HMTPD), mCP, or the like.

The hole transport region (HTR) may have a thickness of 100 Å to 10000 Å or 100 Å to 5000 Å. The hole injection layer (HIL) may have a thickness of, as an example, 30 Å to 1000 Å and the hole transport layer (HTL) may have a thickness of, as an example, 30 Å to 1000 Å. In addition, the electron blocking layer (EBL) may have a thickness of, as an example, 10 Å to 1000 Å. When the thicknesses of the hole transport region (HTR), the hole injection layer (HIL), the hole transport layer (HTL), and the electron blocking layer (EBL) satisfy the ranges described above, a satisfactory hole transport property may be obtained without a substantial drive voltage rise.

The hole transport region (HTR) may further include a charge producing material for improving conductivity, in addition to the material mentioned above. The charge producing material may be uniformly or non-uniformly dispersed in the hole transport region (HTR). The charge producing material may be, as an example, a p-dopant. The p-dopant may be one of a quinone derivative, a metal oxide, and a cyano-containing compound, but is not limited thereto. An example of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxides and molybdenum oxides, and the like, but is not limited thereto.

As described above, the hole transport region (HTR) may further include at least one of the hole buffer layer and the electron blocking layer (EBL). The hole buffer layer may compensate for a resonance distance depending on a light wavelength emitted from the emitting layer (EML) to increase light emission efficiency. As the material included in the hole buffer layer, materials which may be included in the hole transport region (HTR) may be used. The electron blocking layer (EBL) is a layer serving to prevent injection of electrons from the electron transport region (ETR) into the hole transport region (HTR).

The emitting layer (EML) is provided on the hole transport region (HTR). The emitting layer (EML) may have a thickness of, as an example, 100 Å to 1000 Å or 100 Å to 3000 Å. The emitting layer (EML) may have a monolayer structure composed of a single material, a monolayer structure composed of a plurality of different materials from each other, or a multilayer structure having a plurality of layers composed of a plurality of different materials from each other.

Hereinafter, an example in which the ferroelectric fluorescent self-assembly compound of Chemical Formula 1 according to an exemplary embodiment of the present invention described above is included in the emitting layer (EML) will be described. However, the present invention is not limited thereto, and the ferroelectric fluorescent self-assembly compound of Chemical Formula 1 according to an exemplary embodiment of the present invention may be included at least one layer of one or more organic layers provided between the first electrode (EL1) and the second electrode (EL2). As an example, the ferroelectric fluorescent self-assembly compound of Chemical Formula 1 according to an exemplary embodiment of the present invention may be included in the hole transport region (HTR). As an example, the ferroelectric fluorescent self-assembly compound of Chemical Formula 1 may be included in the hole transport layer (HTL) or the electron blocking layer (EBL).

The emitting layer (EML) may include the ferroelectric fluorescent self-assembly compound represented by Chemical Formula 1 of the present invention. Specifically, the emitting layer (EML) may include the ferroelectric fluorescent self-assembly compound of Chemical Formula 1 and may further include one or more binders selected from the group consisting of polyvinylidene fluoride (PVDF), a copolymer of vinylidene fluoride and trifluoroethylene (PVDF-TrFE), a copolymer of vinylidene fluoride and hexafluoroethylene (PVDF-HFP), a copolymer of vinylidene cyanide and vinyl acetate (P(VDCN-VAc)), nylon-11, polyurea-9, polyvinylchloride (PVC), polyacrylonitrile (PAN), polyphthalazinone ether nitrile (PPEN), polyethylene oxide (PEO), and polyether sulfone (PES), and specifically, may further include fluorine-based polymers such as polyvinylidene fluoride (PVDF), a copolymer of vinylidene fluoride and trifluoroethylene (PVDF-TrFE), and a copolymer of vinylidene fluoride and hexafluoroethylene. The binder may perform a function as a medium in which the ferroelectric fluorescent self-assembly compound is dispersed and a binder, and in some cases, may perform a function to reinforce ferroelectricity and piezoelectricity of the organic layer implemented by a heteroaryl compound. In addition, the emitting layer (EML) may further include a host and a dopant, in addition to the fluorescent self-assembly compound of the present invention. The host is not particularly limited as long as it is commonly used, but as an example, tris(8-hydroxyquinolino)aluminum (Alq$_3$), 4,4'-bis(N-carbazolyl)-1,1'-biphenyl (CBP), poly(n-vinylcabazole) (PVK), 9,10-di(naphthalene-2-yl)anthracene (ADN), 4,4', 4"-Tris(carbazol-9-yl)-triphenylamine (TCTA), 1,3,5-tris (N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-Methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-Bis (triphenylsilyl)benzene (UGH2), Hexaphenylcyclotrisiloxane (DPSiO$_3$), octaphenylcyclotetra siloxane (DPSiO$_4$), 2,8-Bis(diphenylphosphoryl)dibenzofuran (PPF), and the like may be used.

The emitting layer (EML) may emit a blue light having a wavelength region of less than 480 nm, and may emit a blue light having a wavelength region of specifically 430 nm to 480 nm, more specifically 440 nm to 480 nm.

A dopant material according to an exemplary embodiment of the present invention is not limited, and various dopants may be selected depending on a desired emitting color and used. As a specific example, when the emitting layer emits a red light, a phosphorescent material such as bis(1-phenylisoquinoline)acetylacetonateiridium (PIQIr(acac)), bis (1-phenylquinoline)acetylacetonate iridium (PQIr(acac)), tris(1-phenylquinoline)iridium (PQIr), and octaethylporphyrin platinum (PtOEP) or a fluorescent material such as tris(8-hydroxyquinolino)aluminum (Alq$_3$) may be used as a light-emitting dopant, but the present invention is not limited thereto. When the emitting layer emits a green light, a phosphorescent material such as fac tris(2-phenylpyridine) iridium (Ir(ppy)$_3$) or a fluorescent material such as tris(8-hydroxyquinolino)aluminum (Alq$_3$), anthracene-based compounds, and pyrene-based compounds may be used as a light-emitting dopant, but the present invention is not limited thereto. When the emitting layer emits a blue light, a phosphorescent material such as (4,6-F2ppy)$_2$Irpic or a fluorescent material such as spiro-DPVBi, spiro-6P, distilbenzene (DSB), distrylarylene (DSA), PFO-based polymers, PPV-based polymers, anthracene-based compounds, and pyrene-based compounds may be used as a light-emitting dopant, but the present invention is not limited thereto.

The electron transport region (ETR) is provided on the emitting layer (EML). The electron transport region (ETR) may include at least one of the hole blocking layer (HBL), the electron transport layer (ETL), and the electron injection layer (EIL), but is not limited thereto.

The electron transport region (ETR) may have a monolayer structure composed of a single material, a monolayer structure composed of a plurality of different materials from each other, or a multilayer structure having a plurality of layers composed of a plurality of different materials from each other. As an example, the electron transport region (ETR) may have a monolayer structure of the electron injection layer (EIL) or the electron transport layer (ETL), or a monolayer structure composed of the electron injection material and the electron transport material. In addition, the electron transport region (ETR) may have a monolayer structure composed of a plurality of different materials from each other, or electron transport layer (ETL)/electron injection layer (EIL) or hole blocking layer (HBL)/electron transport layer (ETL)/electron injection layer (EIL) structure, stacked from the emitting layer (EML) in the order, but is not limited thereto.

The electron transport region (ETR) may have a thickness of, as an example, 1000 Å to 1500 Å.

The electron transport region (ETR) may be formed using various methods such as a vacuum deposition method, a spin coating method, a casting method, a Langmuir-Blodgett method, an inkjet printing method, a laser printing method, and a laser induced thermal imaging (LITI) method.

When the electron transport region (ETR) includes the electron transport layer (ETL), the electron transport region (ETR) may include tris(8-hydroxyquinolinato)aluminum ($Alq_3$), 1,3,5-tri[(3-pyridyl)-phen-3-yl]benzene, 2,4,6-tris (3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-Tri(1-phenyl-1H-benzo[d]imidazol-2-yl)phenyl (TPBi), 2,9-Dimethyl-4,7-diphenyl-1,10-phenanthroline (BCP), 4,7-Diphenyl-1,10-phenanthroline (Bphen), 3-(4-Biphenylyl)-4-phenyl-5-tert-butylphenyl-1,2,4-triazole (TAZ), 4-(Naphthalen-1-yl)-3,5-diphenyl-4H-1,2,4-triazole (NTAZ), 2-(4-Biphenylyl)-5-(4-tert-butylphenyl)-1,3,4-oxadiazole (tBu-PBD), bis(2-methyl-8-quinolinolato-N1,O8)-(1,1'-Biphenyl-4-olato) aluminum (Balq), berylliumbis(benzoquinolin-10-olate) ($Bebq_2$), 9,10-di(naphthalene-2-yl)anthracene (ADN), and a mixture thereof, but is not limited thereto.

The electron transport layer (ETL) may have a thickness of, as an example, 100 Å to 1000 Å or 150 Å to 500 Å. When the thicknesses of the electron transport layers (ETL) satisfy the range described above, a satisfactory electron transport property may be obtained without a substantial drive voltage rise.

When the electron transport region (ETR) includes the electron injection layer (EIL), lanthanum group metals such as LiF, LiQ (Lithium quinolate), $Li_2O$, BaO, NaCl, CsF, or Yb, halogenated metals such as RbCl or RbI, or the like may be used in the electron transport region (ETR), but the present invention is not limited thereto. The electron injection layer (EIL) may be composed of a mixed material of an electron transport material and an insulating organic metal salt. The organic metal salt may be a material having an energy band gap of about 4 eV or more. As an example, the organic metal salt may include metal acetates, metal benzoates, metal acetoacetates, metal acetylacetonates, or metal stearates.

The electron injection layers (EIL) may have a thickness of, as an example, 1 Å to 100 Å or 3 Å to 90 Å. When the thicknesses of the electron injection layers (ETL) satisfy the range described above, a satisfactory electron injection property may be obtained without a substantial drive voltage rise.

The electron transport region (ETR) may include the hole blocking layer (HBL), as described above. The hole blocking layer (HBL) may include, for example, 2,9-dimethyl-4,7-diphenyl-1,10-phenanthroline (BCP), 4,7-diphenyl-1,10-phenanthroline (Bphen), bis[2-(diphenylphosphino)phenyl] ether oxide (DPEPO), or the like, but is not limited thereto.

The second electrode (EL2) is provided on the electron transport region (ETR). The second electrode (EL2) may be a common electrode or a negative electrode. The second electrode (EL2) may be a transmissive electrode, a semi-transmissive electrode, or a reflective electrode. When the second electrode (EL2) is a transmissive electrode, the second electrode (EL2) may be composed of a transparent metal oxide, as an example, indium tin oxide (ITO), indium zinc oxide (IZO), zinc oxide (ZnO), indium tin zinc oxide (ITZO), and the like.

When the second electrode (EL2) is a semi-transmissive electrode or a reflective electrode, the second electrode (EL2) may include Ag, Mg, Cu, Al, Pt, Pd, Au, Ni, Nd, Ir, Cr, Li, Ca, LiF/Ca, LiF/Al, Mo, Ti, or a compound or mixture including the elements (for example, a mixture of Ag and Mg). Otherwise, the second electrode may have a multilayer structure including a reflective film or a semi-transmissive film formed of the material and a transparent conductive film formed of indium tin oxide (no), indium zinc oxide (IZO), zinc oxide (ZnO), indium tin zinc oxide (ITZO), and the like. The second electrode (EL2) may be connected to an auxiliary electrode. When the second electrode (EL2) is connected to the auxiliary electrode, resistance of the second electrode (EL2) may be decreased.

In the organic light-emitting element according to an exemplary embodiment of the present invention, as voltage is applied to each of the first electrode (EL1) and the second electrode (EL2), holes injected from the first electrode (EL1) are moved to the emitting layer (EML) through the hole transport region (HTR) and electrons injected from the second electrode (EL2) are moved to the emitting layer (EML) through the electron transport region (ETR). The electrons and the holes are recombined in the emitting layer (EML) to produce excitons, and the excitons falls from an excited state to a ground state to emit light.

In addition, the organic light-emitting element including the ferroelectric fluorescent self-assembly compound according to an exemplary embodiment of the present invention may be a front emission type, back emission type, or both surface emission type.

When the organic light-emitting element is the front emission type, the first electrode may be a reflective electrode and the second electrode may be a transmissive electrode or a semi-transmissive electrode. When the organic light-emitting element is a rear emission type, the first electrode may be a transmissive electrode or a semi-transmissive electrode and the second electrode may be a reflective electrode.

In addition, the present invention provides an electronic device adopting the organic electronic element of the present invention.

Hereinafter, the present invention will be described in detail through the following Examples. However, the following Examples are only illustrative of the present invention, and do not limit the scope of the present invention in any way.

Prior to that, terms and words used in the present specification and claims are not to be construed as a general or dictionary meaning but are to be construed as meaning and concepts meeting the technical ideas of the present invention based on a principle that the inventors can appropriately define the concepts of terms in order to describe their own inventions in best mode. Therefore, the configurations illustrated in the Examples and drawings described herein are merely the most preferred exemplary embodiment of the present invention but do not represent all of the technical spirit of the present invention. Thus, it should be understood that there are various equivalents and modified examples to replace them at the time of filing the present application.

[Example 1] Preparation of Compound 1

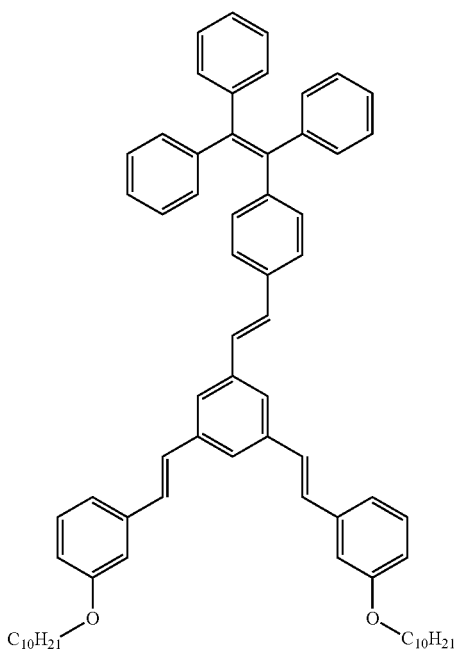

To a solution in which 5.41 g (15.0 mmol, 2.2 equiv.) of 4-(1,2,2-triphenylvinyl)benzaldehyde and 5.07 g (6.8 mmol, 1 equiv.) of diethyl(3,5-bis(3-decyloxystyryl)phenyl)methylphosphonate were added to anhydrous tetrahydrofuran (100 ml) under an argon atmosphere, 2.52 g (22.5 mmol, 3.3 equiv.) of potassium tert-butoxide was added while maintaining 0° C. The solution was stirred at 0° C. for 1 hour and then further stirred at room temperature for another 1 hour. The reaction mixture was quenched with saline, extraction was performed with dichloromethane, and the extract was washed with saline and dried with magnesium sulfate. After filtration, the solvent was evaporated under reduced pressure. Separation and purification were performed by silica gel column chromatography (dichloromethane/cyclohexane 1:1) to obtain Compound 1 as a solid.

$^1$H NMR, δ(ppm)=7.43 (s, 3H), 7.42 (d, 10H), 7.26 (t, 6H), 7.15 (t, 2H), 7.11 (t, 3H), 6.99 (s, 6H), 6.98 (d, 2H), 6.93 (s, 2H), 6.62 (d, 2H), 3.94 (t, 4H), 1.71 (p, 4H), 1.33 (m, 4H), 1.29 (p, 24H), 0.96 (t, 6H).

Compounds 2 to 28 were prepared with different starting materials and solvents from those of the above method, and the prepared compounds are shown in Table 1.

TABLE 1
| Compound No. | Compound structure | $^1$H NMR, δ (ppm) |
|---|---|---|
| 2 | 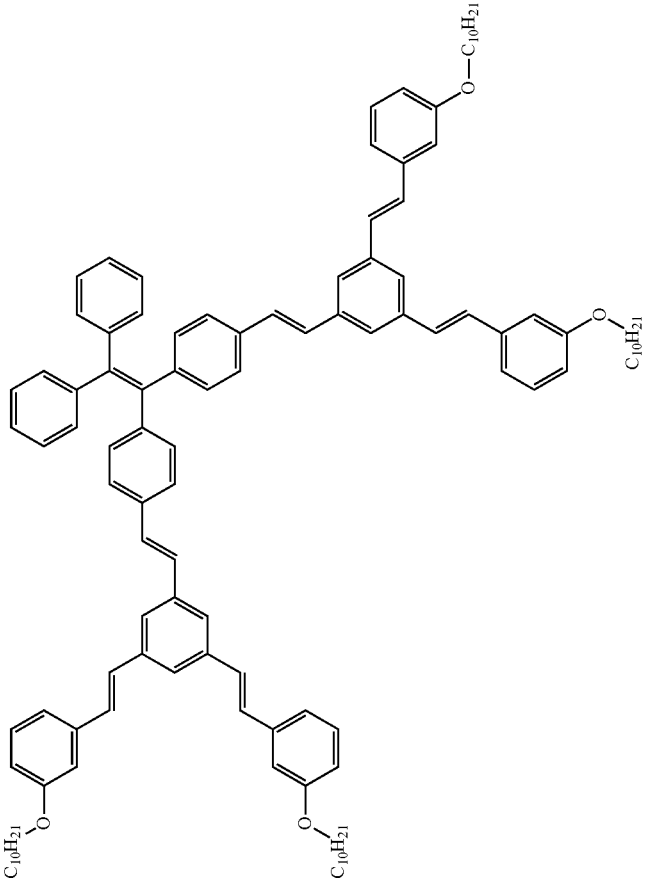 | 7.43 (s, 6H), 7.42 (d, 12H), 7.26 (t, 4H), 7.15 (t, 4H), 7.11 (t, 2H), 6.99 (s, 12H), 6.98 (d, 4H), 6.93 (s, 4H), 6.62 (d, 4H), 3.94 (t, 8H), 1.71 (p, 8H), 1.33 (m, 8H), 1.29 (p, 48H), 0.96 (t, 12H). |

TABLE 1-continued
| Compound No. | Compound structure | $^1$H NMR, δ (ppm) |
|---|---|---|
| 3 | 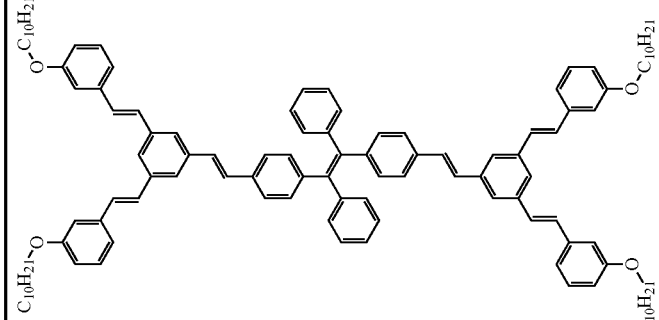 | 7.43 (s, 6H), 7.42 (d, 12H), 7.26 (t, 4H), 7.15 (t, 4H), 7.11 (t, 2H), 6.99 (s, 12H), 6.98 (d, 4H), 6.93 (s, 4H), 6.62 (d, 4H), 3.94 (t, 8H), 1.71 (p, 8H), 1.33 (m, 8H), 1.29 (p, 48H), 0.96 (t, 12H). |

TABLE 1-continued
| Compound No. | Compound structure | $^1$H NMR, δ (ppm) |
|---|---|---|
| 4 | 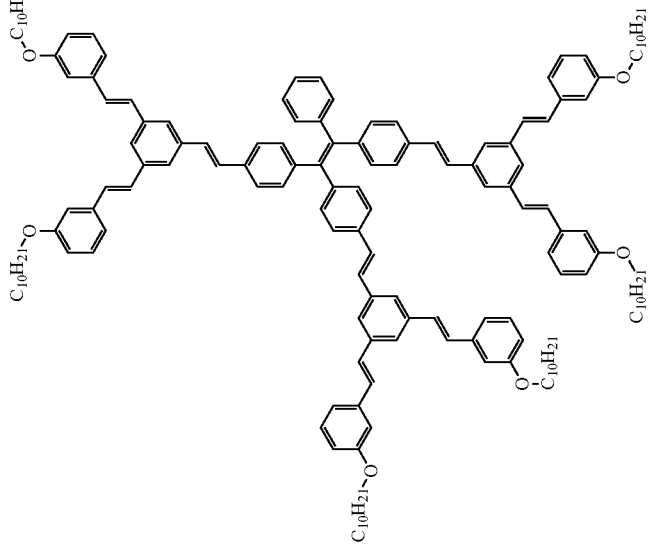 | 7.43 (s, 9H), 7.42 (d, 14H), 7.26 (t, 2H), 7.15 (t, 6H), 7.11 (t, 1H), 6.99 (s, 18H), 6.98 (d, 6H), 6.93 (s, 6H), 6.62 (d, 6H), 3.94 (t, 12H), 1.71 (p, 12H), 1.33 (m, 12H), 1.29 (p, 72H), 0.96 (t, 18H). |

TABLE 1-continued
| Compound No. | Compound structure | $^1$H NMR, δ (ppm) |
|---|---|---|
| 5 | 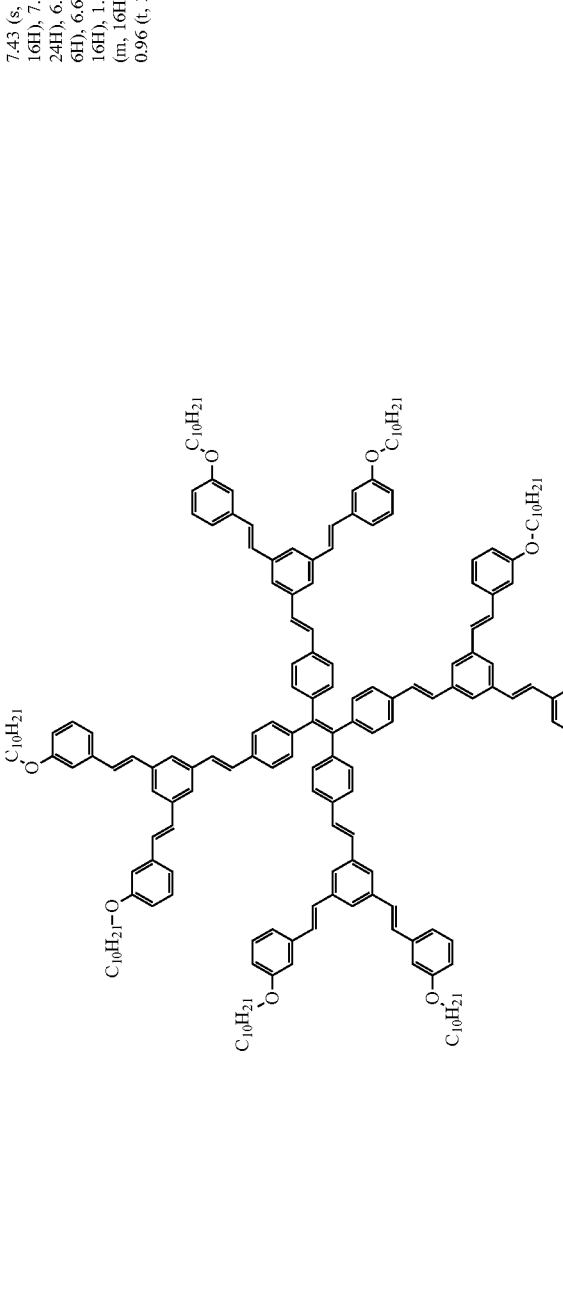 | 7.43 (s, 12H), 7.42 (d, 16H), 7.15 (t, 8H), 6.99 (s, 24H), 6.98 (d, 8H), 6.93 (s, 6H), 6.62 (d, 8H), 3.94 (t, 16H), 1.71 (p, 16H), 1.33 (m, 16H), 1.29 (p, 96H), 0.96 (t, 24H) |

TABLE 1-continued

| Compound No. | Compound structure | ¹H NMR, δ (ppm) |
|---|---|---|
| 6 | (structure) | 7.48 (d, 8H), 7.43 (s, 3H), 7.42 (d, 2H), 7.26 (t, 2H), 7.15 (t, 2H), 7.11 (t, 1H), 6.99 (s, 6H), 6.98 (d, 2H), 6.93 (s, 2H), 6.77 (d, 4H), 6.62 (d, 2H), 3.94 (t, 4H), 1.71 (p, 4H), 1.33 (m, 4H), 1.29 (p, 24H), 0.96 (t, 6H) |

TABLE 1-continued

| Compound No. | Compound structure | $^1$H NMR, δ (ppm) |
|---|---|---|
| 7 | 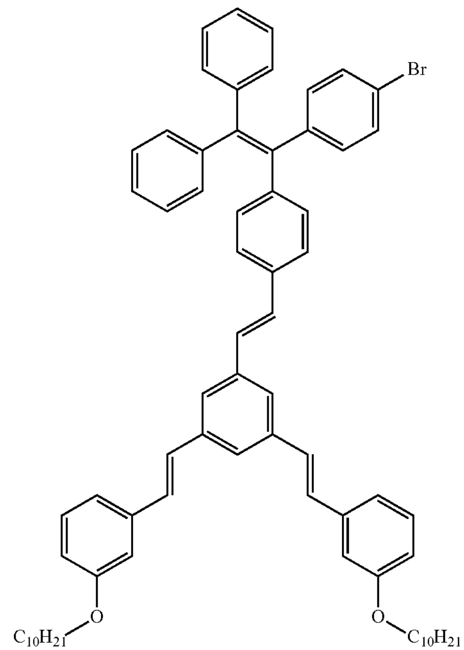 | 7.43-7.42 (m, 13H), 7.31-7.26 (m, 6H), 7.15-7.11 (m, 4H), 6.99-6.93 (m, 10H), 6.62 (d, 2H), 3.94 (t, 4H), 1.71 (p, 4H), 1.33-1.29 (m, 28H), 0.96 (t, 6H) |

TABLE 1-continued
| Compound No. | Compound structure | $^1$H NMR, δ (ppm) |
|---|---|---|
| 8 | 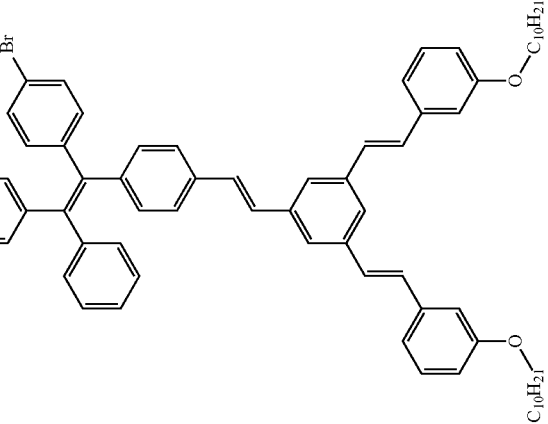 | 7.43-7.42 (m, 13H), 7.31-7.26 (m, 6H), 7.15-7.11 (m, 3H), 6.99-6.93 (m, 10H), 6.62 (d, 2H), 3.94 (t, 4H), 1.71 (p, 4H), 1.33-1.29 (m, 28H), 0.96 (t, 6H) |

TABLE 1-continued

| Compound No. | Compound structure | $^1$H NMR, δ (ppm) |
|---|---|---|
| 9 | (structure) | 7.43-7.42 (m, 13H), 7.31 (d, 6H), 7.15 (t, 2H), 6.99-6.93 (m, 10H), 6.62 (d, 2H), 3.94 (t, 4H), 1.71 (p, 4H), 1.33-1.29 (m, 28H), 0.96 (t, 6H) |

TABLE 1-continued

| Compound No. | Compound structure | $^1$H NMR, δ (ppm) |
|---|---|---|
| 10 | (structure) | 7.43 (s, 3H), 7.42 (d, 10H), 7.26 (t, 6H), 7.15 (t, 2H), 7.11 (t, 3H), 6.99 (s, 6H), 6.98 (d, 2H), 6.93 (s, 2H), 6.62 (d, 2H), 3.94 (t, 4H), 1.71 (p, 4H), 1.33 (m, 4H), 1.29 (p, 32H), 0.96 (t, 6H) |

TABLE 1-continued

| Compound No. | Compound structure | ¹H NMR, δ (ppm) |
|---|---|---|
| 11 | (structure: tetraphenylethylene linked via phenyl–vinyl to a central benzene bearing two styryl arms, each terminating in a 3-(C₁₅H₃₁O)phenyl group) | 7.43 (s, 3H), 7.42 (d, 10H), 7.26 (t, 6H), 7.15 (t, 2H), 7.11 (t, 3H), 6.99 (s, 6H), 6.98 (d, 2H), 6.93 (s, 2H), 6.62 (d, 2H), 3.94 (t, 4H), 1.71 (p, 4H), 1.33 (m, 4H), 1.29 (p, 44H), 0.96 (t, 6H) |

TABLE 1-continued

| Compound No. | Compound structure | ¹H NMR, δ (ppm) |
|---|---|---|
| 12 | (structure) | 7.43 (s, 3H), 7.42 (d, 10H), 7.26 (t, 6H), 7.15 (t, 2H), 7.11 (t, 3H), 6.99 (s, 6H), 6.98 (d, 2H), 6.93 (s, 2H), 6.62 (d, 2H), 3.94 (t, 4H), 1.71 (p, 4H), 1.33 (m, 4H), 1.29 (p, 64H), 0.96 (t, 6H) |

TABLE 1-continued
| Compound No. | Compound structure | 1H NMR, δ (ppm) |
|---|---|---|
| 13 | 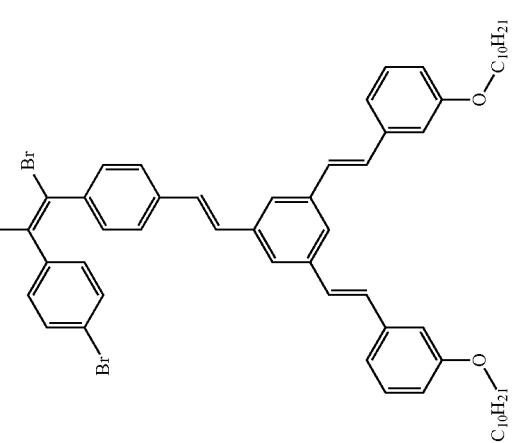 | 7.43-7.42 (m, 11H), 7.31 (d, 4H), 7.15 (t, 2H), 6.99-6.93 (m, 10H), 6.62 (d, 2H), 3.94 (t, 4H), 1.71 (p, 4H), 1.33-1.29 (m, 28H), 0.96 (t, 6H) |

TABLE 1-continued

| Compound No. | Compound structure | ¹H NMR, δ (ppm) |
|---|---|---|
| 14 | (structure) | 7.43 (s, 3H), 7.17 (d, 2H), 7.15 (t, 2H), 6.99-6.93 (m, 8H), 6.62 (d, 2H), 3.94 (t, 4H), 1.71 (p, 4H), 1.33-1.29 (m, 28H), 0.96 (t, 6H) |

TABLE 1-continued
| Compound No. | Compound structure | $^1$H NMR, δ (ppm) |
|---|---|---|
| 15 | 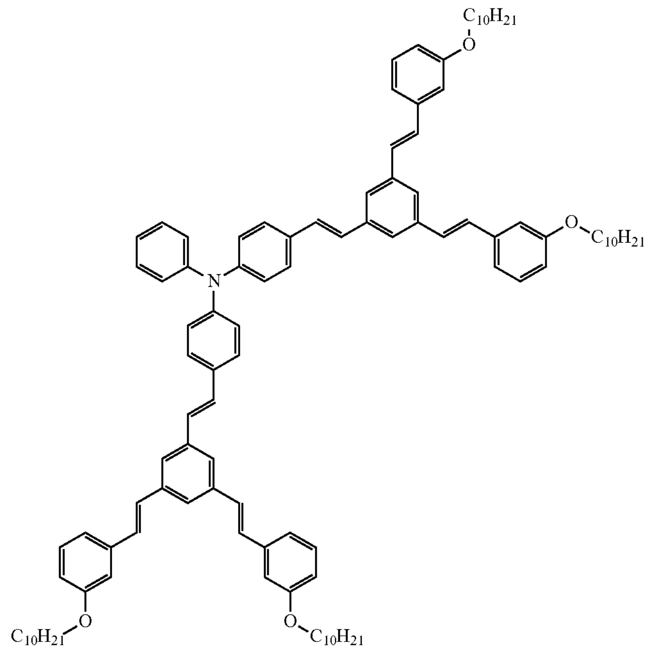 | 7.43 (s, 6H), 7.17 (d, 4H), 7.15 (t, 4H), 7.01-6.93 (m, 22H), 6.62 (m, 5H), 6.46 (d, 6H), 3.94 (t, 8H), 1.71 (p, 8H), 1.33-1.29 (m, 56H), 0.96 (t, 12H) |

TABLE 1-continued
| Compound No. | Compound structure | $^1$H NMR, δ (ppm) |
|---|---|---|
| 16 | 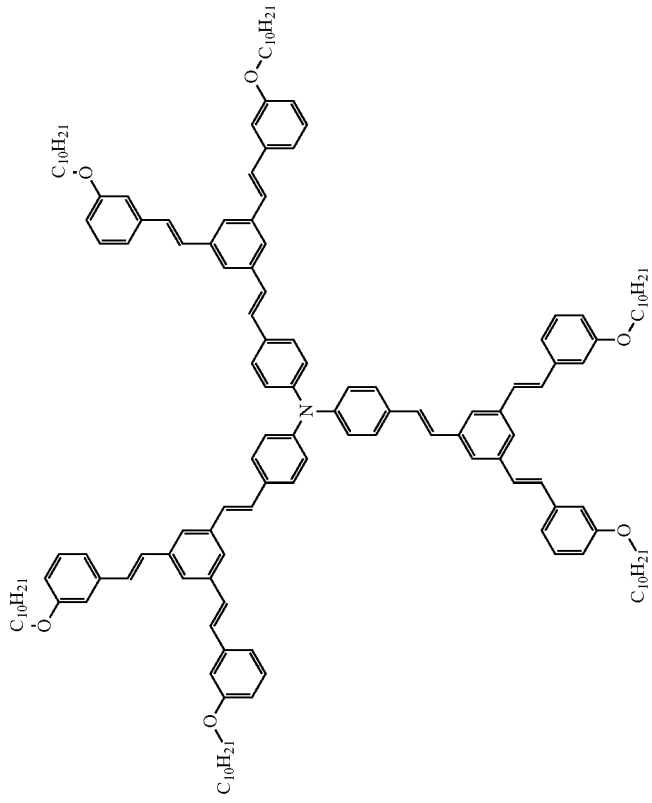 | 7.43 (s, 9H), 7.17 (d, 6H), 7.15 (t, 6H), 6.99-6.93 (m, 30H), 6.62 (d, 6H), 6.46 (d, 6H), 3.94 (t, 12H), 1.71 (p, 12H), 1.33-1.29 (m, 84H), 0.96 (t, 18H) |

TABLE 1-continued

| Compound No. | Compound structure | ¹H NMR, δ (ppm) |
|---|---|---|
| 17 | (structure) | 7.43 (s, 3H), 7.18 (d, 2H), 7.17 (d, 6H), 7.15 (t, 2H), 6.99-6.93 (m, 8H), 6.62 (m, 3H), 6.46 (d, 4H), 3.94 (t, 4H), 1.71 (p, 4H), 1.33-1.29 (m, 28H), 0.96 (t, 6H) |

TABLE 1-continued

| Compound No. | Compound structure | 1H NMR, δ (ppm) |
|---|---|---|
| 18 | (structure shown) | 7.43 (s, 3H), 7.18 (d, 4H), 7.17 (d, 2H), 7.15 (t, 2H), 6.99-6.93 (m, 10H), 6.62 (d, 2H), 6.46 (d, 2H), 6.35 (d, 4H), 3.94 (t, 4H), 1.71 (p, 4H), 1.33-1.29 (m, 28H), 0.96 (t, H) |

TABLE 1-continued
| Compound No. | Compound structure | $^1$H NMR, δ (ppm) |
|---|---|---|
| 19 | 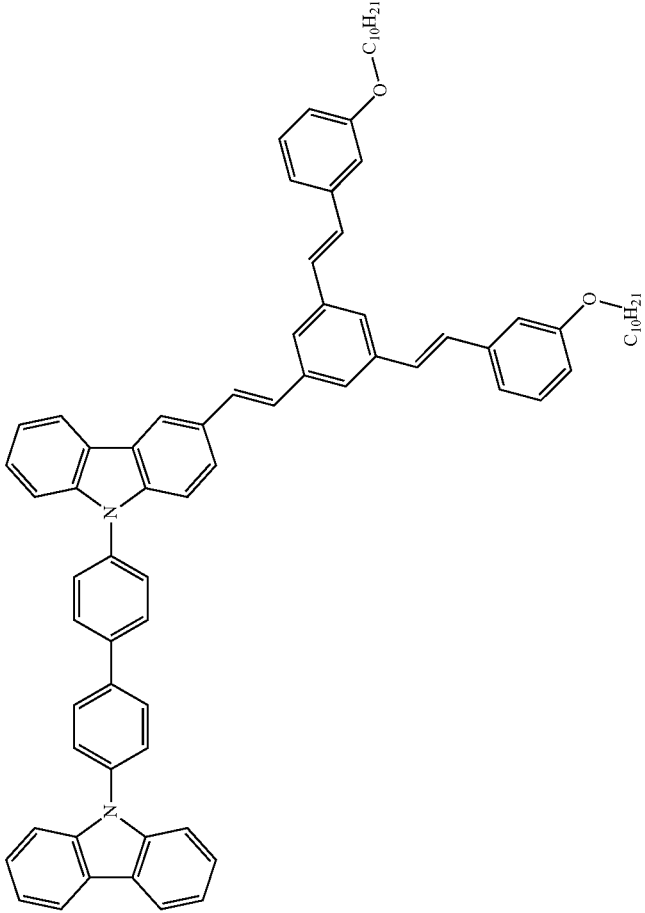 | 7.71, (s, 1H), 7.55 (d, 3H), 7.50-7.40 (m, 11H), 7.30 (d, 4H), 7.24 (d, 1H), 7.15 (t, 2H), 7.08 (t, 3H), 6.99-6.93 (m, 8H), 6.62 (d, 2H), 3.94 (t, 4H), 1.71 (p, 4H), 1.33-1.29 (m, 28H), 0.96 (t, 6H) |

| Compound No. | Compound structure | $^1$H NMR, δ (ppm) |
|---|---|---|
| 20 | (structure) | 11.0 (s, 1H), 8.42 (s, 1H), 7.95 (d, 1H), 7.71 (s, 1H), 7.61-7.30 (m, 17H), 7.24 (d, 1H), 7.15 (t, 2H), 7.08 (t, 2H), 6.99-6.93 (m, 10H), 6.62 (d, 2H), 3.94 (t, 4H), 1.71 (p, 4H), 1.33-1.29 (m, 28H), 0.96 (t, 6H) |

TABLE 1-continued
| Compound No. | Compound structure | $^1$H NMR, δ (ppm) |
|---|---|---|
| 21 | 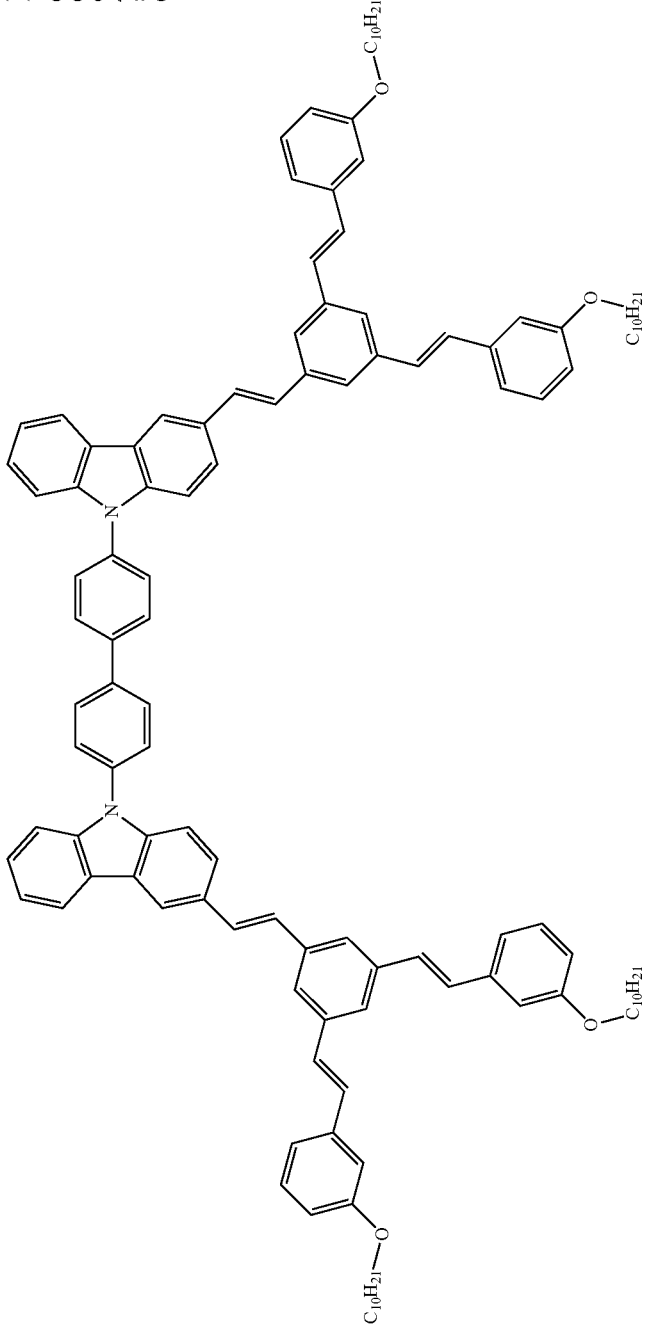 | 7.71, (s, 2H), 7.55 (d, 2H), 7.50-7.40 (m, 14H), 7.30 (d, 4H), 7.24 (d, 2H), 7.15 (t, 4H), 7.08 (t, 2H), 6.99-6.93 (m, 20H), 6.62 (d, 4H), 3.94 (t, 8H), 1.71 (p, 8H), 1.33-1.29 (m, 56H), 0.96 (t, 12H) |

TABLE 1-continued
| Compound No. | Compound structure | $^1$H NMR, δ (ppm) |
|---|---|---|
| 22 | 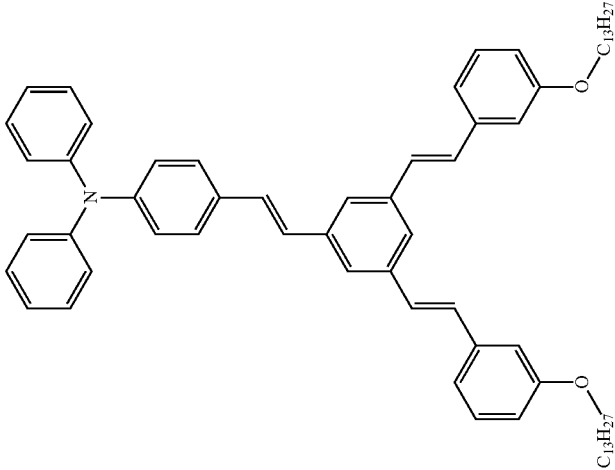 | 7.43 (s, 3H), 7.17 (d, 2H), 7.15 (t, 2H), 6.99-6.93 (m, 8H), 6.62 (d, 2H), 3.94 (t, 4H), 1.71 (p, 4H), 1.33-1.29 (m, 36H), 0.96 (t, 6H) |

TABLE 1-continued

| Compound No. | Compound structure | $^1$H NMR, δ (ppm) |
|---|---|---|
| 23 | (triphenylamine-stilbene-bis(3-hexadecyloxystyryl)benzene structure) | 7.43 (s, 3H), 7.17 (d, 2H), 7.15 (t, 2H), 6.99-6.93 (m, 8H), 6.62 (d, 2H), 3.94 (t, 4H), 1.71 (p, 4H), 1.33-1.29 (m, 48H), 0.96 (t, 6H) |

TABLE 1-continued
| Compound No. | Compound structure | $^1$H NMR, δ (ppm) |
|---|---|---|
| 24 | 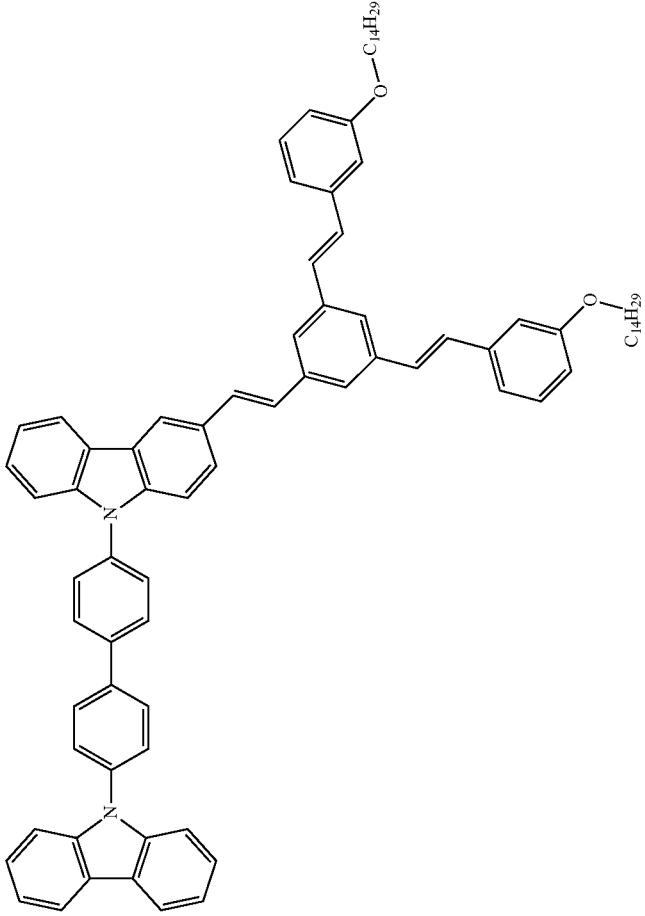 | 7.71, (s, 1H), 7.55 (d, 3H), 7.50-7.40 (m, 11H), 7.30 (d, 4H), 7.24 (d, 1H), 7.15 (t, 2H), 7.08 (t, 3H), 6.99-6.93 (m, 8H), 6.62 (d, 2H), 3.94 (t, 4H), 1.71 (p, 4H), 1.33-1.29 (m, 40H), 0.96 (t, 6H) |

TABLE 1-continued
| Compound No. | Compound structure | ¹H NMR, δ (ppm) |
|---|---|---|
| 25 | 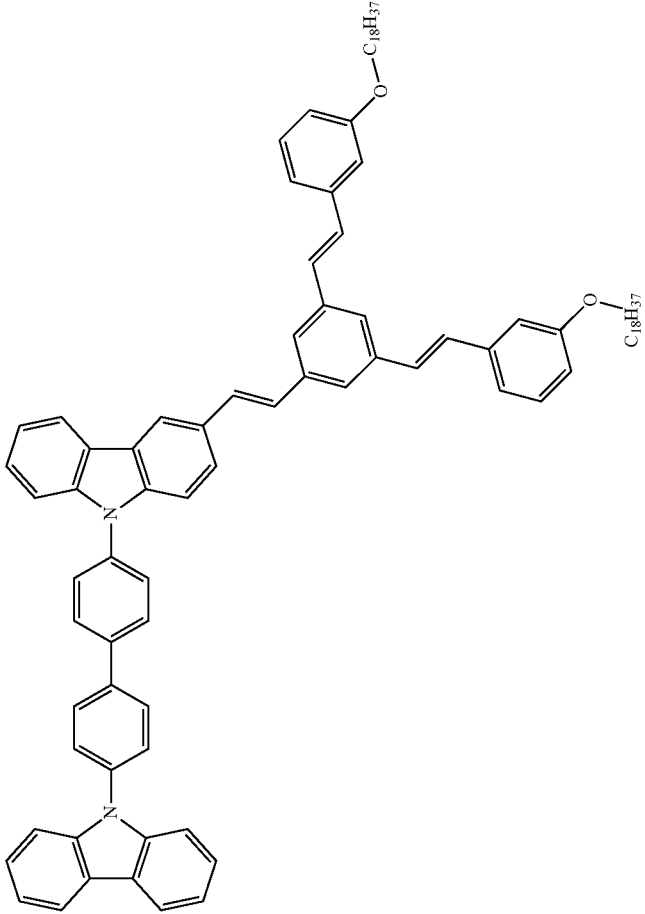 | 7.71, (s, 1H), 7.55 (d, 3H), 7.50-7.40 (m, 11H), 7.30 (d, 4H), 7.24 (d, 1H), 7.15 (t, 2H), 7.08 (t, 3H), 6.99-6.93 (m, 8H), 6.62 (d, 2H), 3.94 (t, 4H), 1.71 (p, 4H), 1.33-1.29 (m, 56H), 0.96 (t, 6H) |

TABLE 1-continued
| Compound No. | Compound structure | $^1$H NMR, δ (ppm) |
|---|---|---|
| 26 | 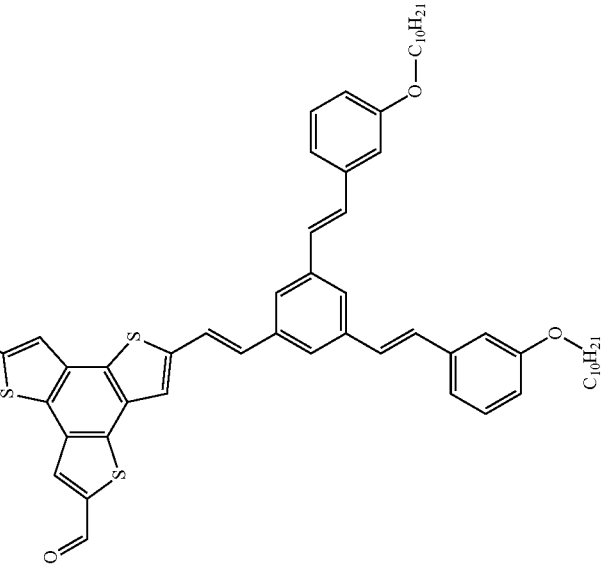 | 9.61 (s, 2H), 7.94 (s, 2H), 7.46 (s, 1H), 7.31-7.30 (m, 3H), 7.15 (t, 2H), 6.99-6.93 (m, 10H), 6.62 (d, 2H), 3.94 (t, 4H), 1.71 (p, 4H), 1.33 (m, 4H), 1.29 (m, 24H), 0.96 (t, 6H) |

TABLE 1-continued

| Compound No. | Compound structure | ¹H NMR, δ (ppm) |
|---|---|---|
| 27 | (structure) | 9.61 (s, 1H), 7.94 (s, 2H), 7.46 (s, 1H), 7.31-7.30 (m, 6H), 7.15 (t, 4H), 6.99-6.93 (m, 20H), 6.62 (d, 4H), 3.94 (t, 8H), 1.71 (p, 8H), 1.33 (m, 8H), 1.29 (m, 48H), 0.96 (t, 12H) |

TABLE 1-continued
| Compound No. | Compound structure | $^1$H NMR, δ (ppm) |
|---|---|---|
| 28 | 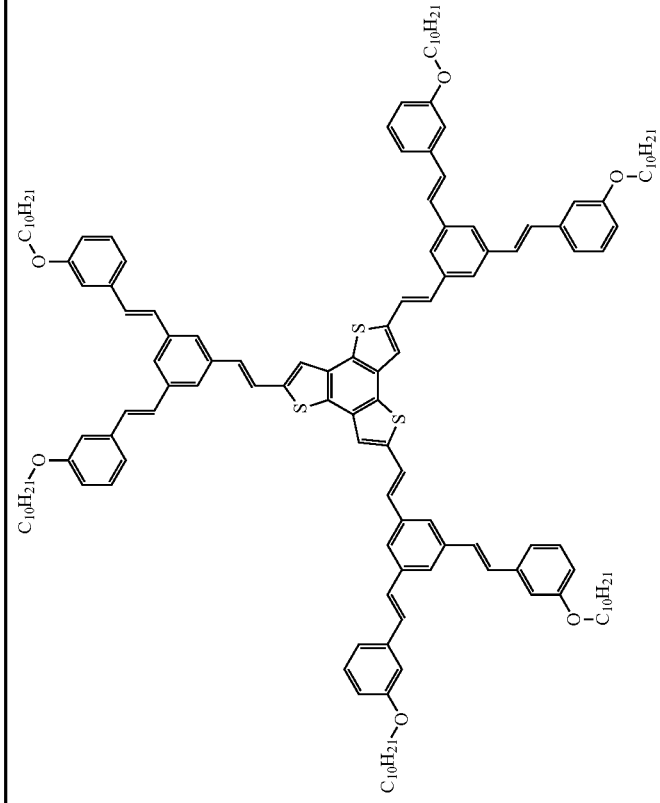 | 7.46 (s, 3H), 7.31-7.30 (m, 9H), 7.15 (t, 6H), 6.99-6.93 (m, 30H), 6.62 (d, 6H), 3.94 (t, 12H), 1.71 (p, 12H), 1.33 (m, 12H), 1.29 (m, 72H), 0.96 (t, 18H) |

[Example 2] Preparation of Compound 29

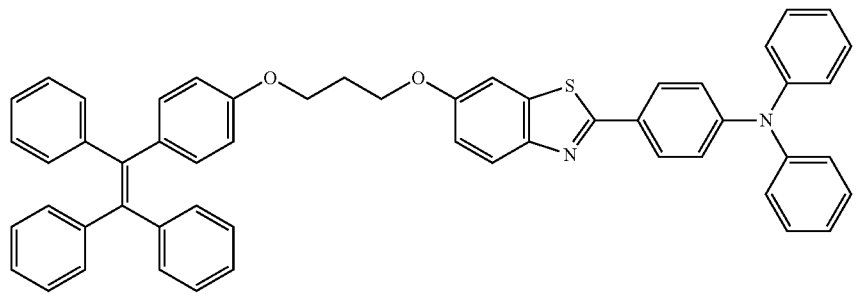

2-Amino-5-methoxythiophenol (9.85 g, 63.5 mmol) and 4-(diphenylamino)benzaldehyde (17.60 g, 64.4 mmol) were dissolved in DMSO (80 ml). The mixture was heated to 170° C. for 20 minutes. The reaction mixture was cooled to room temperature and then poured into 500 ml of water. Subsequently, ethyl acetate (100 ml) was added thereto and the entire mixture was completely stirred. A light yellow precipitate was separated by vacuum filtration, washed with ethyl acetate (3×10 ml), and dried under vacuum to obtain a solid product.

The previously synthesized product (1.4 g, 3.5 mmol) was dissolved in anhydrous DCM (100 ml) and pure $BBr_3$ (4.6 ml, 49 mmol) was added thereto dropwise at −78° C. under an argon atmosphere. The reaction mixture was slowly heated to room temperature and then stirred for 16 hours. The reactant was quenched with water (100 ml) and the pH was neutralized to 4 to 7 with an aqueous NaOH solution. A yellow precipitate was separated by vacuum filtration, washed with water (3×10 ml), methanol (10 ml), DCM (10 ml), and anhydrous ethanol (3×10 ml), and then vacuum-dried to obtain 2-(4-(diphenylamino)phenyl)benzo[d]thiazol-6-ol.

NaH was added to THF (100 ml), 1-(3-bromopropoxy)-4-(1,2,2-triphenylvinyl)benzene (23.47 g, 0.05 mol) was added dropwise to the reaction mixture, and the previously synthesized 2-(4-(diphenylamino)phenyl)benzo[d]thiazol-6-ol (19.72 g, 0.05 mol) was added at 0° C. for 30 minutes. Stirring was performed at room temperature overnight to obtain a brown reaction mixture, which was poured into 2 M HCl-ice (60 ml). The reaction mixture was extracted with diethyl ether (3×60 ml), and the extract was washed with a saturated aqueous sodium hydrogen carbonate solution and dried with magnesium sulfate. After removing the solvent by rotary evaporation, the residue was separated and purified by gel column chromatography to obtain Compound 29 as a solid.

$^1$H NMR, δ(ppm)=8.12 (d, 1H), 7.63 (s, 1H), 7.42 (d, 6H), 7.31 (d, 2H), 7.26-7.23 (m, 8H), 7.11 (t, 3H), 7.06 (d, 1H), 7.01 (t, 4H), 6.77 (d, 2H), 6.62 (t, 2H), 6.52 (d, 2H), 6.46 (d, 4H), 3.94 (t, 4H), 2.13 (p, 2H).

Compounds 30 to 34 were prepared with different starting materials and solvents from those of the above method, and the prepared compounds are shown in Table 2.

TABLE 2
| Compound No. | Compound structure | $^1$H NMR, δ (ppm) |
|---|---|---|
| 30 | 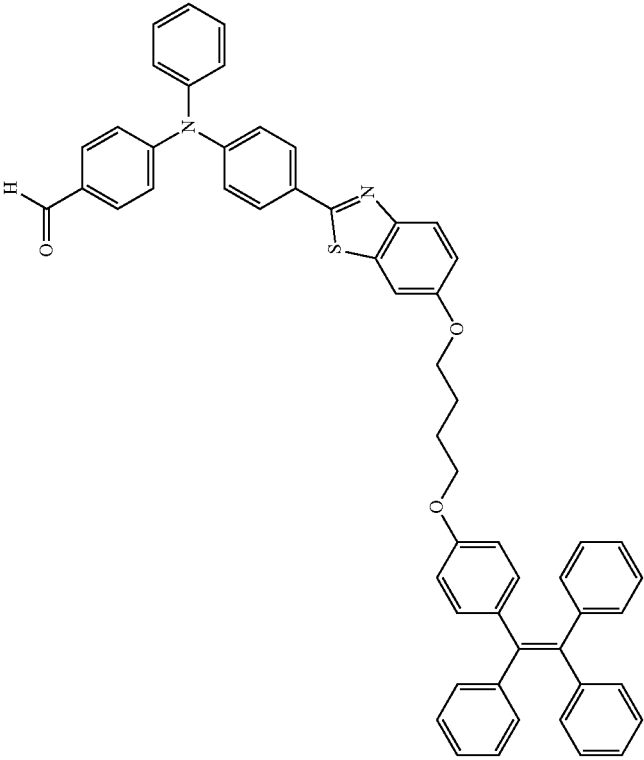 | 9.87 (s, 1H), 8.12 (d, 1H), 7.63 (s, 1H), 7.56 (d, 2H), 7.42 (d, 6H), 7.31 (d, 2H), 7.26 (t, 6H), 7.11 (t, 3H), 7.06 (d, 1H), 7.01 (t, 2H), 6.77 (d, 2H), 6.65 (d, 2H), 6.62 (t, 2H), 6.52 (d, 2H), 6.46 (d, 2H), 3.94 (t, 4H), 1.71 (p, 4H) |

TABLE 2-continued

| Compound No. | Compound structure | 1H NMR, δ (ppm) |
|---|---|---|
| 31 | 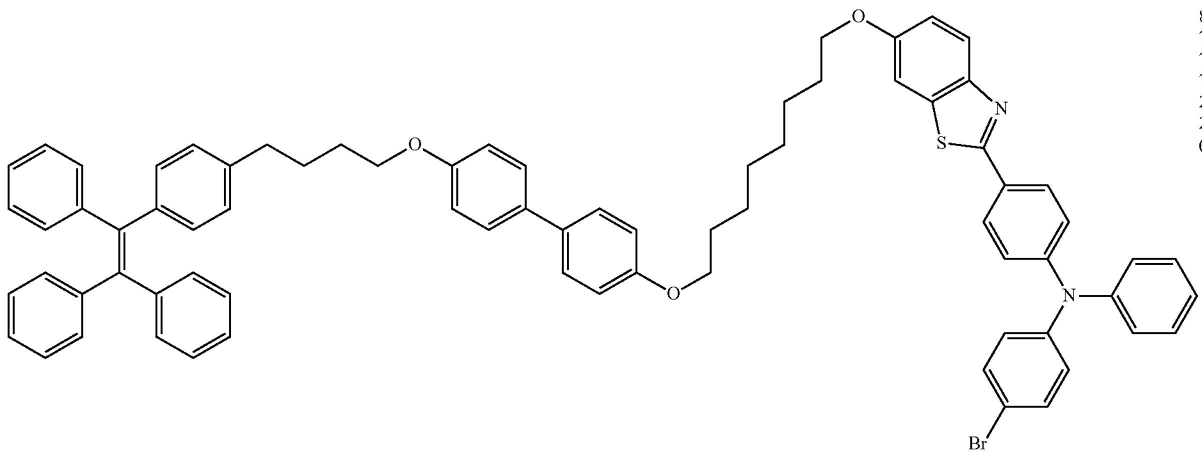 [SMILES: Brc1ccc(N(c2ccccc2)c2ccc(-c3nc4ccc(OCCCCCCCCOc5ccc(-c6ccc(OCCCCc7ccc(C(=C(c8ccccc8)c8ccccc8)c8ccccc8)cc7)cc6)cc5)cc4s3)cc2)cc1] | 8.12 (d, 1H), 7.63 (s, 1H), 7.56 (d, 4H), 7.42 (d, 6H), 7.37 (t, 6H), 7.23 (d, 2H), 7.18 (d, 2H), 7.06 (d, 1H), 7.01 (t, 2H), 6.83 (d, 4H), 6.62 (t, 2H), 6.52 (d, 2H), 6.46 (d, 2H), 6.35 (d, 2H), 3.94 (t, 4H), 2.55 (t, 2H), 1.71 (p, 4H), 1.61 (p, 2H), 1.29 (m, 8H) |
| 32 | 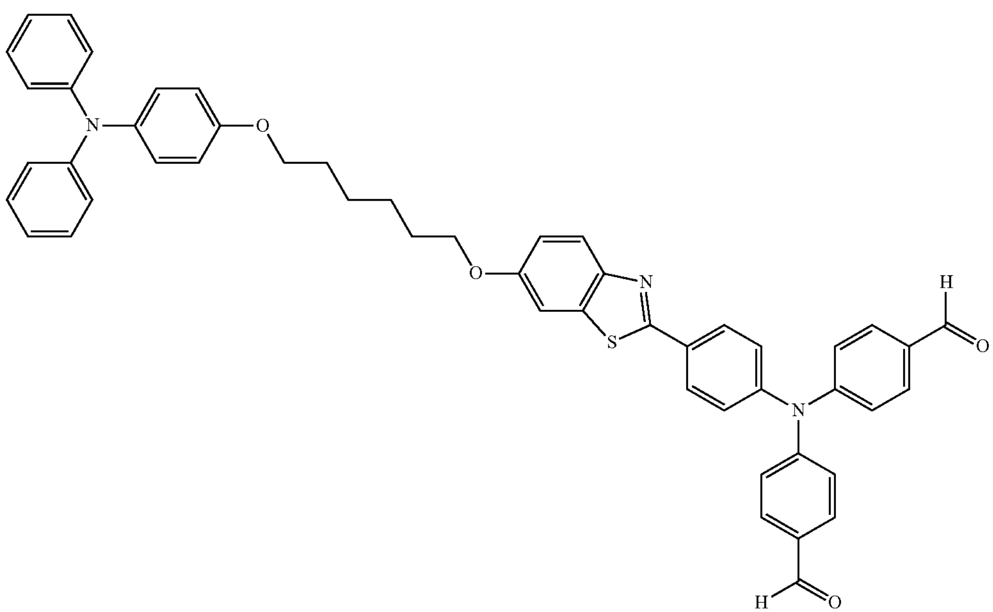 [SMILES: O=Cc1ccc(N(c2ccc(C=O)cc2)c2ccc(-c3nc4ccc(OCCCCCCOc5ccc(N(c6ccccc6)c6ccccc6)cc5)cc4s3)cc2)cc1] | 9.87 (s, 2H), 8.12 (d, 1H), 7.63 (s, 1H), 7.56 (d, 2H), 7.23 (d, 2H), 7.06 (d, 1H), 7.01 (t, 1H), 6.65 (d, 4H), 6.62 (t, 2H), 6.52 (d, 2H), 6.46 (d, 2H), 3.94 (t, 4H), 1.71 (p, 4H). |

TABLE 2-continued

| Compound No. | Compound structure | $^1$H NMR, δ (ppm) |
|---|---|---|
| 33 | 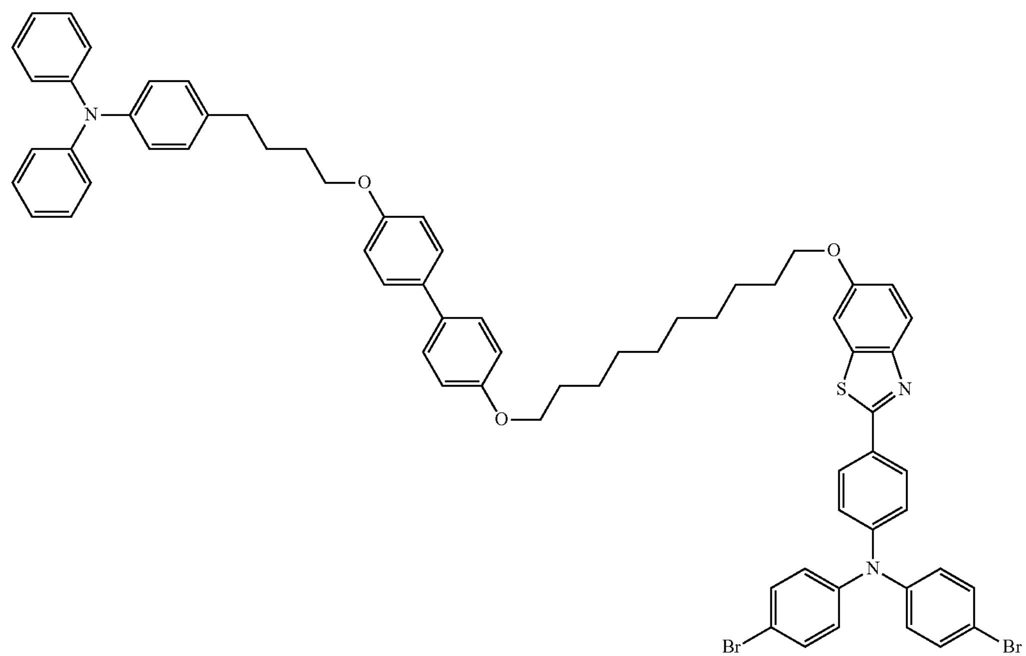 [SMILES: Brc1ccc(N(c2ccc(Br)cc2)c2ccc(-c3nc4ccc(OCCCCCCCCCCOc5ccc(-c6ccc(OCCCCc7ccc(N(c8ccccc8)c8ccccc8)cc7)cc6)cc5)cc4s3)cc2)cc1] | 8.12 (d, 1H), 7.63 (s, 1H), 7.37 (d, 6H), 7.23 (d, 2H), 7.18 (d, 4H), 7.06 (d, 1H), 7.01 (t, 4H), 6.87 (d, 2H), 6.83 (d, 4H), 6.62 (t, 2H), 6.52 (d, 2H), 6.46 (d, 2H), 6.41 (d, 2H), 6.35 (d, 4H), 3.94 (t, 6H), 2.55 (t, 2H), 1.71 (p, 6H), 1.61 (p, 2H), 1.29 (m, 12H). |

[Example 3] Preparation of Compound 34

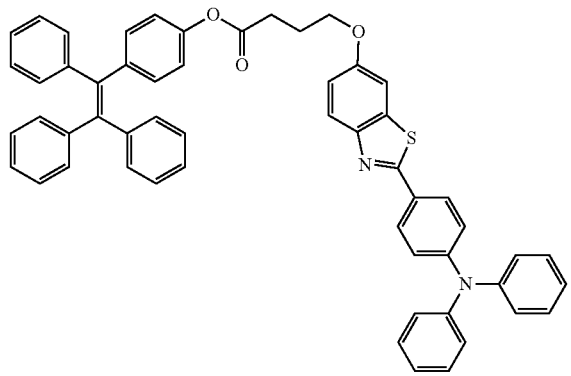 [SMILES: O=C(CCCOc1ccc2nc(-c3ccc(N(c4ccccc4)c4ccccc4)cc3)sc2c1)Oc1ccc(C(=C(c2ccccc2)c2ccccc2)c2ccccc2)cc1]

NaH was added to THF (100 ml), 4-(1,2,2-triphenylvinyl)phenyl 4-bromobutanoate (24.87 g, 0.05 mol) was added dropwise thereto, and Compound 14 (2-(4-(diphenylamino)phenyl)benzo[d]thiazol-6-ol, 19.72 g, 0.05 mol) was added thereto at 0° C. for 30 minutes. Stirring was performed at room temperature overnight to obtain a brown reaction mixture, which was poured into 2 M HCl-ice (60 ml). The reaction mixture was extracted with diethyl ether (3×60 ml), and the extract was washed with a saturated aqueous sodium hydrogen carbonate solution and brine and dried with magnesium sulfate. After removing the solvent by rotary evaporation, the residue was separated and purified by gel column chromatography to obtain Compound 34 as a solid.

$^1$H NMR, δ(ppm)=8.12 (d, 1H), 7.63 (s, 1H), 7.42 (d, 6H), 7.31 (d, 2H), 7.26 (t, 6H), 7.11 (t, 3H), 7.06 (d, 1H), 7.01 (t, 4H), 6.77 (d, 2H), 6.62 (t, 2H), 6.52 (d, 2H), 6.46 (d, 4H), 3.94 (t, 4H), 2.13 (p, 2H).

Compounds 35 to 38 were prepared with different starting materials and solvents from those of the above method, and the prepared compounds are shown in Table 3.

TABLE 3

| Compound No. | Compound structure | $^1$H NMR δ (ppm) |
|---|---|---|
| 35 | 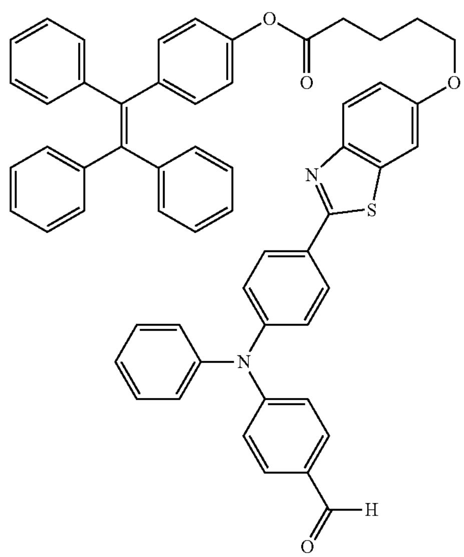 [SMILES: O=Cc1ccc(N(c2ccccc2)c2ccc(-c3nc4ccc(OCCCCC(=O)Oc5ccc(C(=C(c6ccccc6)c6ccccc6)c6ccccc6)cc5)cc4s3)cc2)cc1] | 9.87 (s, 1H), 8.12 (d, 1H), 7.63 (s, 1H), 7.56 (d, 2H), 7.42 (d, 6H), 7.39 (d, 2H), 7.26 (t, 6H), 7.23 (d, 2H), 7.11 (t, 3H), 7.07 (d, 2H), 7.06 (d, 1H), 7.01 (t, 2H), 6.62 (t, 1H), 6.52 (d, 2H), 6.46 (d, 2H), 3.94 (t, 2H), 2.23 (t, 2H), 1.98 (p, 2H), 1.71 (p, 2H), 1.56 (p, 2H) |
| 36 | 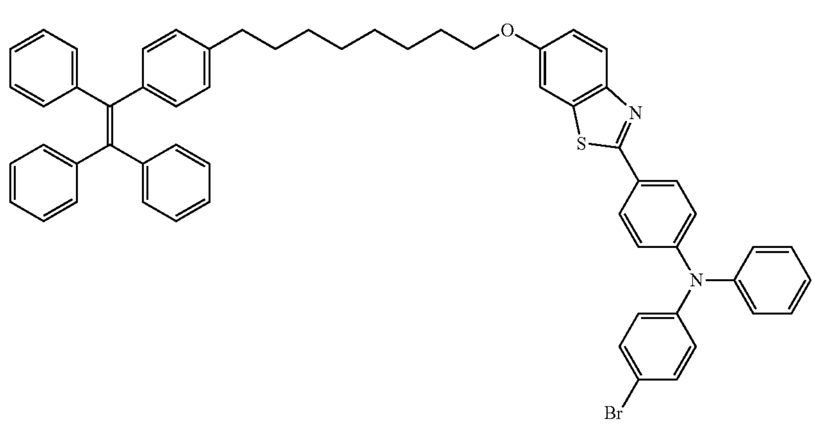 [SMILES: Brc1ccc(N(c2ccccc2)c2ccc(-c3nc4ccc(OCCCCCCCCc5ccc(C(=C(c6ccccc6)c6ccccc6)c6ccccc6)cc5)cc4s3)cc2)cc1] | 8.12 (d, 1H), 7.63 (s, 1H), 7.23 (d, 2H), 7.18 (d, 4H), 7.06 (d, 1H), 7.01 (t, 4H), 6.62 (t, 2H), 6.52 (d, 2H), 6.46 (d, 4H), 6.41 (d, 2H), 6.35 (d, 4H), 3.94 (t, 2H), 2.55 (t, 2H), 1.71 (p, 2H), 1.62 (p, 2H), 1.29 (p, 12H). |

TABLE 3-continued
| Compound No. | Compound structure | $^1$H NMR δ (ppm) |
|---|---|---|
| 37 | 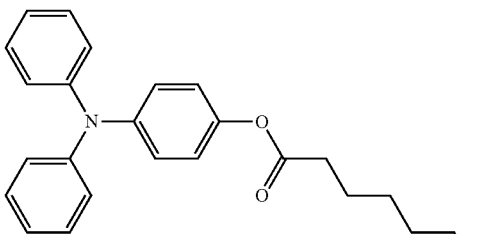 | 9.87 (s, 2H), 8.12 (d, 1H), 7.63 (s, 1H), 7.56 (d, 4H), 7.23 (d, 2H), 7.06 (d, 1H), 7.01 (t, 4H), 6.82 (d, 2H), 6.65 (d, 4H), 6.62 (t, 2H), 6.52 (d, 2H), 6.46 (d, 4H), 6.43 (d, 2H), 3.94 (t, 2H), 2.23 (t, 2H), 1.71 (p, 2H), 1.56 (p, 2H), 1.29 (p, 4H). |
| 38 | 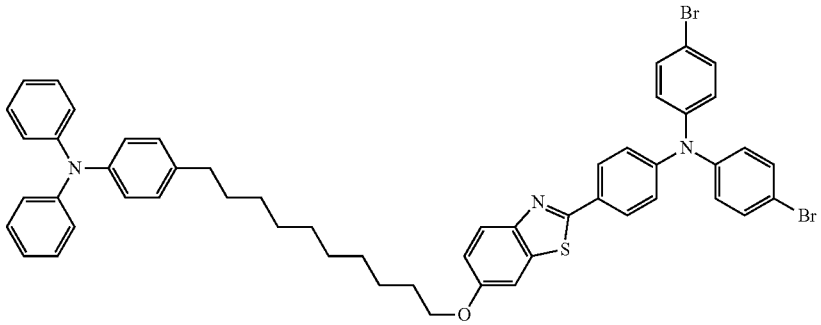 [SMILES: Brc1ccc(N(c2ccc(Br)cc2)c2ccc(-c3nc4ccc(OCCCCCCCCCCc5ccc(N(c6ccccc6)c6ccccc6)cc5)cc4s3)cc2)cc1] | 8.12 (d, 1H), 7.63 (s, 1H), 7.23 (d, 2H), 7.18 (d, 4H), 7.06 (d, 1H), 7.01 (t, 4H), 6.62 (t, 2H), 6.52 (d, 2H), 6.46 (d, 4H), 6.41 (d, 2H), 6.35 (d, 4H), 3.94 (t, 2H), 2.55 (t, 2H), 1.71 (p, 2H), 1.62 (p, 2H), 1.29 (p, 12H). |
[Example 4] Preparation of Compound 39
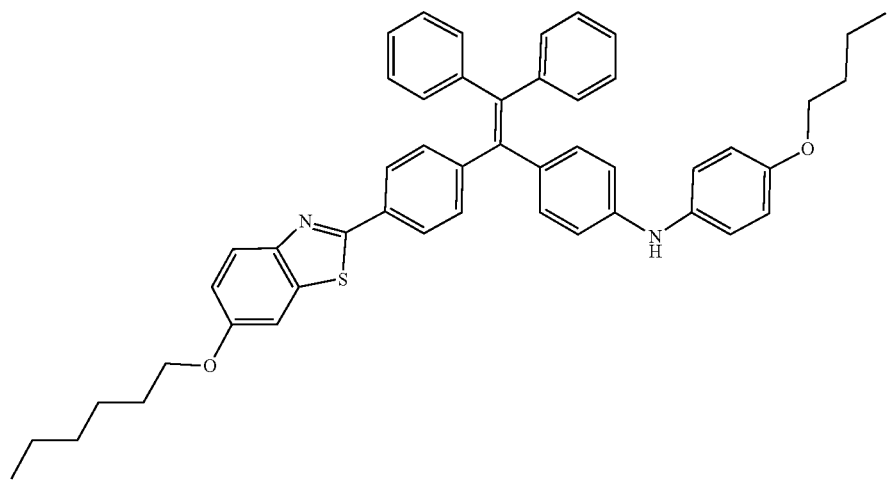 [SMILES: CCCCCCOc1ccc2nc(-c3ccc(C(=C(c4ccccc4)c4ccccc4)c4ccc(Nc5ccc(OCCCC)cc5)cc4)cc3)sc2c1]

2-(4-(4-bromophenyl-phenylamino)phenyl)benzo[d]thiazol-6-ol (10 mmol) was dissolved an anhydrous acetone under an argon atmosphere. Thereafter, potassium carbonate (2.76 g, 20 mmol) was added thereto and stirring was performed for 15 minutes. Then, 1-bromobutane (1.37 g, 10 mmol) was added thereto, stirring was performed at room temperature for 4 hours, and the solvent was removed, thereby obtaining 4-bromo-N-(4-(6-butoxybenzo[d]thiazol-2-yl)phenyl)-N-phenylbenzenamine. Thereafter, 4-bromo-N-(4-(6-butoxybenzo[d]thiazol-2-yl)phenyl)-N-phenylbenzenamine (2.55 g, 5 mmol), 4-butoxybenzenamine (1.24 g, 7.5 mmol), and tBuONa (0.77 g, 8 mmol) were added to a reactor under argon atmosphere, dissolved in anhydrous toluene (100 ml), and stirred. Thereafter, Pd(OAc)$_2$ (0.07 g, 0.5 mmol) and P(tBu)$_3$HBF$_4$ (260 mg, 1 mmol) were added to the reactor and the mixture was reacted at 110° C. for 24 hours. When the reaction was completed, the reaction mixture was cooled down to room temperature, dichloromethane was added thereto, filtration was performed, and washing was performed repeatedly with D.I. water and 1 M HCl. Then, the solvent was removed using an evaporator, and silica gel column chromatography using PE/DCM was performed to obtain Compound 39 as a solid.

$^1$H NMR, δ(ppm)=8.12 (d, 1H), 7.63 (s, 1H), 7.48 (d, 4H), 7.42 (d, 6H), 7.26 (t, 4H), 7.06 (d, 1H), 7.01 (d, 1H), 6.52 (d, 4H), 6.46 (d, 2H), 6.35 (d, 2H), 4.00 (s, 1H), 3.94 (t, 2H), 1.71 (p, 4H), 1.33 (m, 4H), 1.29 (p, 4H), 0.96 (t, 6H)

The following Compounds 40 to 42 were obtained with different starting materials and solvents from those of the above method.

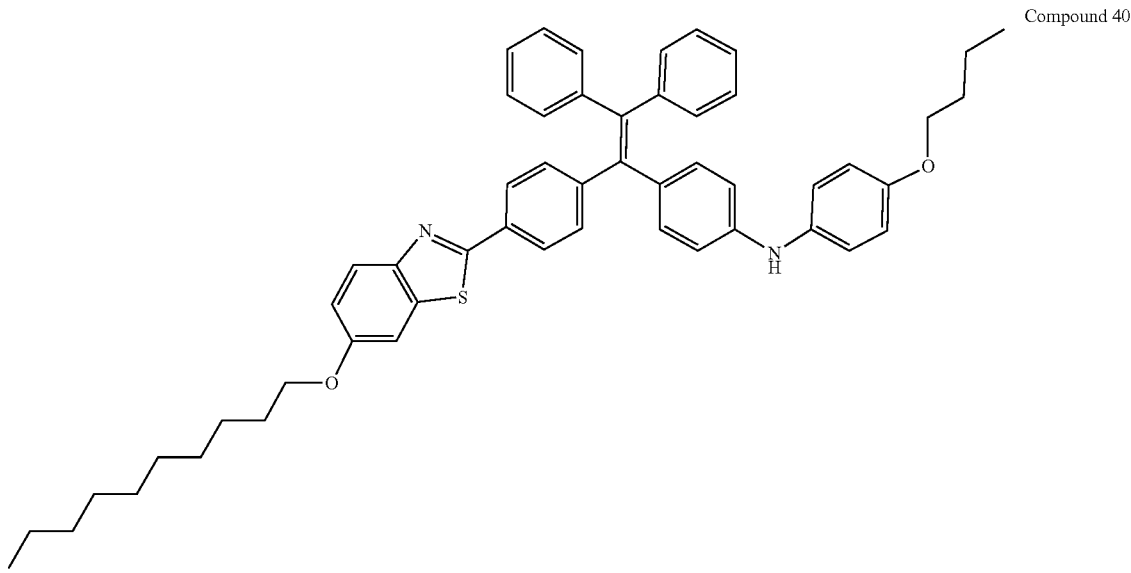 [SMILES: CCCCCCCCCCOc1ccc2nc(-c3ccc(C(=C(c4ccccc4)c4ccccc4)c4ccc(Nc5ccc(OCCCC)cc5)cc4)cc3)sc2c1]

Compound 40

$^1$H NMR, δ(ppm)=8.12 (d, 1H), 7.63 (s, 1H), 7.48 (d, 4H), 7.42 (d, 6H), 7.26 (t, 4H), 7.06 (d, 1H), 7.01 (d, 1H), 6.52 (d, 4H), 6.46 (d, 2H), 6.35 (d, 2H), 4.00 (s, 1H), 3.94 (t, 2H), 1.71 (p, 4H), 1.33 (m, 4H), 1.29 (p, 12H), 0.96 (t, 6H).

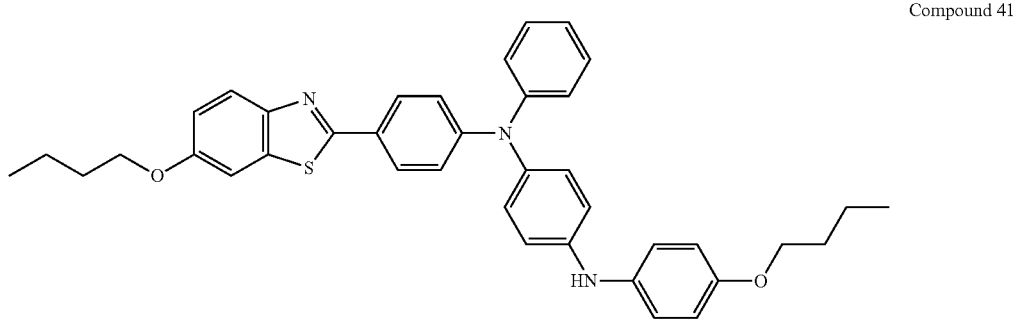 [SMILES: CCCCOc1ccc(Nc2ccc(N(c3ccccc3)c3ccc(-c4nc5ccc(OCCCC)cc5s4)cc3)cc2)cc1]

Compound 41

¹H NMR, δ(ppm)=8.12 (d, 1H), 7.63 (s, 1H), 7.42 (d, 6H), 7.31 (d, 2H), 7.23 (d, 2H), 7.06 (d, 1H), 7.01 (t, 2H), 6.62 (t, 1H), 6.52 (d, 4H), 6.46 (d, 2H), 4.00 (s, 1H), 3.94 (t, 2H), 1.71 (p, 4H), 1.33 (m, 4H), 0.96 (t, 6H).

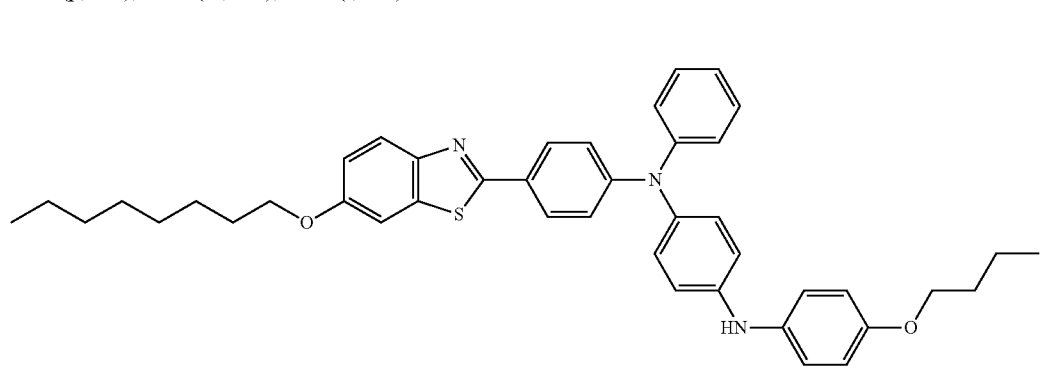

Compound 42

¹H NMR, δ(ppm)=8.12 (d, 1H), 7.63 (s, 1H), 7.23 (d, 2H), 7.06 (d, 1H), 7.01 (t, 2H), 6.62 (t, 1H), 6.52 (d, 4H), 6.46 (d, 2H), 6.35 (d, 2H), 6.21 (d, 4H), 4.00 (s, 1H), 3.94 (t, 2H), 1.71 (p, 4H), 1.33 (m, 4H), 1.29 (p, 8H), 0.96 (t, 6H).

[Example 5] Preparation of Compound 43

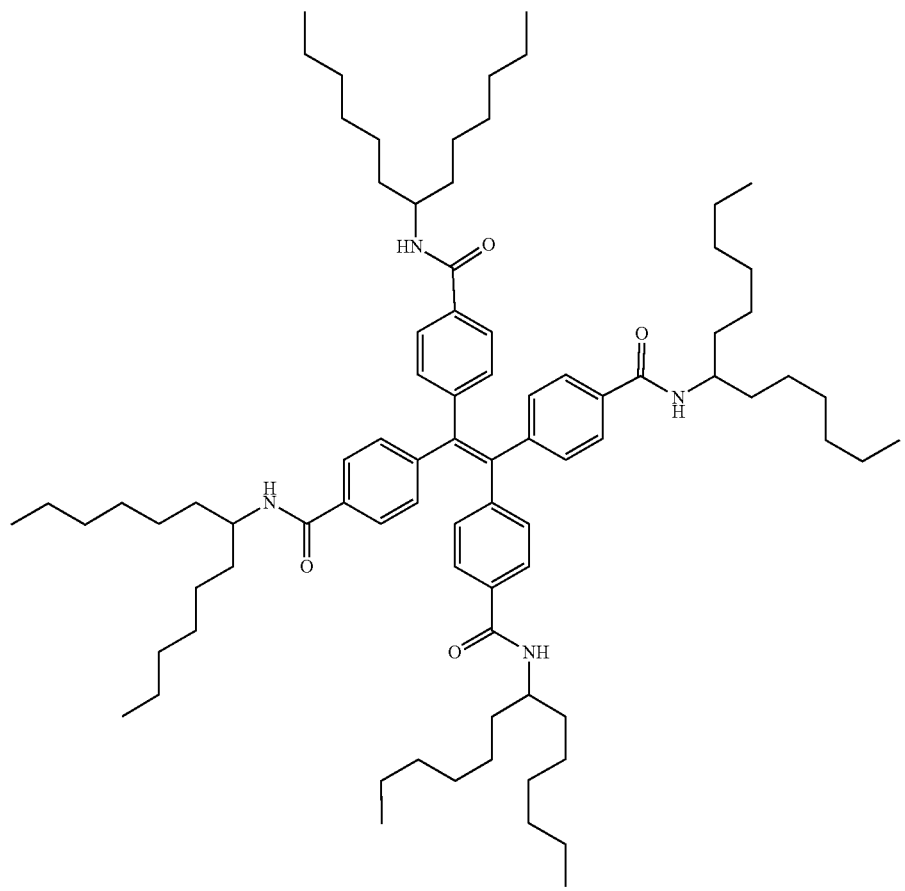 [SMILES: CCCCCCC(CCCCCC)NC(=O)c1ccc(C(=C(c2ccc(C(=O)NC(CCCCCC)CCCCCC)cc2)c2ccc(C(=O)NC(CCCCCC)CCCCCC)cc2)c2ccc(C(=O)NC(CCCCCC)CCCCCC)cc2)cc1]

4,4',4'',4'''-(1,2-ethenediylidene)tetrakis-benzoic acid (5.0 g, 9.9 mmol) and 4-(4,6-dimethoxy-1,3,5-triazin-2-yl)-4-methylmorpholinium chloride (DMTMM, 16.7 g, 60.4 mmol) were dissolved in anhydrous tetrahydrofuran, and then tridecan-7-amine (12.5 g, 62.8 mmol) was added thereto. The solution was stirred at room temperature for 12 hours, and the solvent was removed by distillation under reduced pressure. The residue was dissolved in chloroform and washed with a sodium hydrogen carbonate, a 1% hydrochloric acid solution, and water, successively, and moisture was removed by anhydrous magnesium sulfate. After removing the solvent, Compound 22 as a white solid was obtained by a filtration process.

$^1$H NMR, δ(ppm)=8.00 (s, 4H), 7.95 (d, 8H), 7.60 (d, 8H), 3.58 (p, 4H), 1.55 (q, 16H), 1.33 (m, 16H), 1.29 (p, 48H), 0.96 (t, 24H).

The following Compound 44 was obtained with different starting materials and solvents from those of the above method.

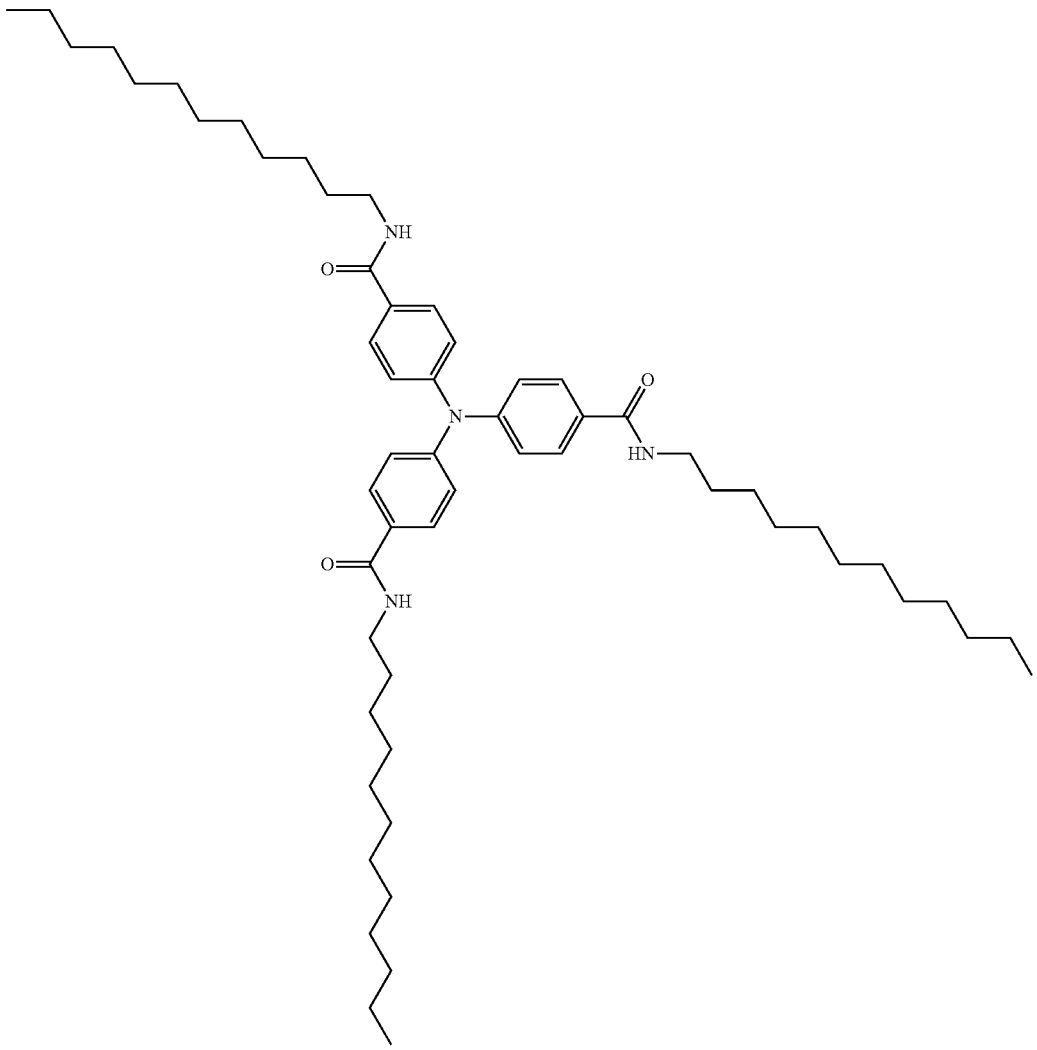

Compound 44

$^1$H NMR, δ(ppm)=8.00 (s, 3H), 7.70 (d, 6H), 6.64 (d, 6H), 3.20 (t, 6H), 1.59 (p, 6H), 1.33 (m, 6H), 1.29 (p, 48H), 0.96 (t, 9H).

[Example 6] Preparation of Compound 45

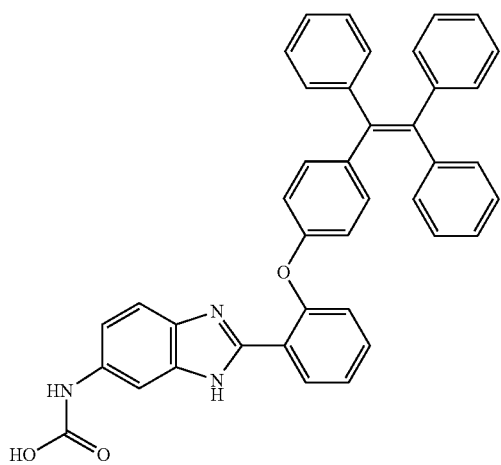 [SMILES: O=C(O)Nc1ccc2nc(-c3ccccc3Oc3ccc(C(=C(c4ccccc4)c4ccccc4)c4ccccc4)cc3)[nH]c2c1]

4 N HCl (15 ml) was added to benzene-1,2,4-triamine (10 mmol). Thereafter, 2-hydroxybenzoic acid was added thereto, and the mixture was heated to reflux for 24 hours. Then, the solution was cooled down and neutralized with 2 N NaOH, the solution was filtrated, and washing was performed with water. To the material (10 mmol) obtained by the above process, anhydrous THF was added, the temperature was lowered to 0° C., t-butylchloroformate was slowly added thereto, and stirring was performed for 2 hours. 100 ml of D.I. water was added thereto to terminate the reaction, and an organic layer was collected from the divided layers to remove the solvent, thereby obtaining a solid. The obtained solid was recrystallized using DMF to obtain (2-(2-hydroxyphenyl)-1H-benzo[d]imidazol-6-yl)carbamic acid.

DMF (5 ml) was added to a round bottom flask under an argon atmosphere, (2-(2-hydroxyphenyl)-1H-benzo[d]imidazol-6-yl)carbamic acid (1 mmol) and potassium carbonate (1.5 mmol) were dissolved therein, 1-(1-(4-bromophenyl)-2,2-diphenylvinyl)benzene (1 mmol) was added thereto, and 0.02 mmol of 4-(aminomethyl)benzoic acid and copper were added thereto as a catalyst. Stirring was performed at 110° C. for 3 hours, the mixture was cooled down, and the solvent was removed by distillation under reduced pressure. The residue was dissolved in dichloromethane, and the copper catalyst was removed by a magnet. The remaining solution was filtered, the solvent was removed by rotating distillation under reduced pressure, and separation and purification were performed by silica gel column chromatography using ethyl acetate/hexane to obtain Compound 45 as a solid.

$^1$H NMR: δ (ppm)=11.00 (s, 1H), 8.08 (s, 1H), 8.00 (s, 1H), 7.68 (d, 1H), 7.64 (d, 1H), 7.44 (d, 1H), 7.42 (d, 6H), 7.38 (d, 2H), 7.26 (t, 6H), 7.18 (t, 1H), 7.11 (t, 3H), 7.04 (t, 1H), 6.98 (d, 1H), 6.92 (d, 2H), 5.00 (s, 1H).

[Example 7] Preparation of Compound 46

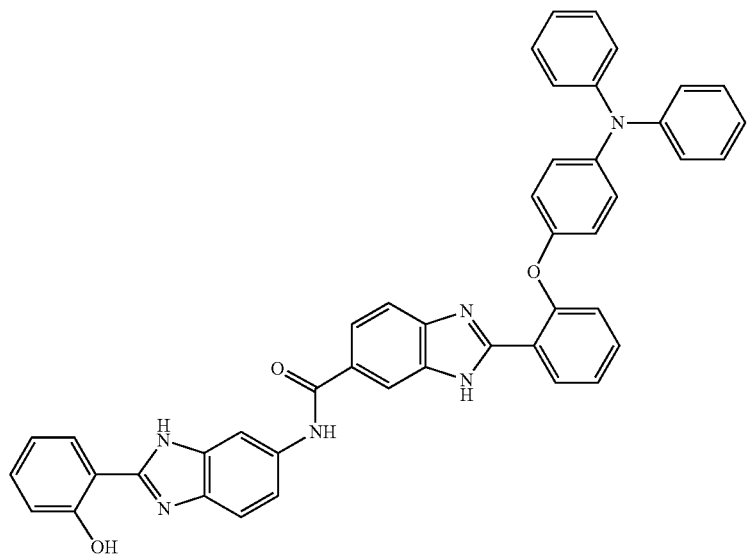 [SMILES: O=C(Nc1ccc2nc(-c3ccccc3O)[nH]c2c1)c1ccc2nc(-c3ccccc3Oc3ccc(N(c4ccccc4)c4ccccc4)cc3)[nH]c2c1]

4 N HCl(15 ml) was added to benzene-1,2,4-triamine (10 mmol). Thereafter, 2-hydroxybenzoic acid was added thereto, and the mixture was heated under reflux for 24 hours. Thereafter, the solution was cooled down and neutralized by 2 N NaOH, and then the solid was filtered and washed with water to obtain Material 1. 4 N HCl (15 ml) was added to 3,4-diaminobenzoyl chloride (10 mmol). Thereafter, 2-hydroxybenzoic acid was added thereto, and the mixture was heated under reflux for 24 hours. Thereafter, the solution was cooled down and neutralized by 2 N NaOH, and then the solid was filtered and washed with water to obtain Material 2. To Material 1 (10 mmol) obtained by the process, anhydrous THF was added, the temperature was lowered to 0° C., Material 2 (10 mmol) was slowly added thereto, and stirring was performed for 2 hours. Thereafter, 100 ml of D.I. water was added thereto to terminate the reaction, and an organic layer was collected from the divided layers to remove the solvent, thereby obtaining a solid. Thereafter, recrystallization was performed using DMF to obtain -(2-hydroxyphenyl)-N-(2-(2-hydroxyphenyl)-1H-benzo[d]imidazol-6-yl)-3H-benzo[d]imidazole-5-carboxamide. DMF (5 ml) was added to a round bottom flask under an argon atmosphere, 2-(2-hydroxyphenyl)-N-(2-(2-hydroxyphenyl)-1H-benzo[d]imidazol-6-yl)-3H-benzo[d]imidazole-5-carboxamide (1 mmol) and potassium carbonate (1.5 mmol) were dissolved therein, 1-(1-(4-bromophenyl)-2,2-diphenylvinyl)benzene (1 mmol) was added thereto, and 0.02 mmol of 4-(aminomethyl)benzoic acid and copper were added thereto as a catalyst. Stirring was performed at 110° C. for 3 hours, the mixture was cooled down, and the solvent was removed by distillation under reduced pressure. The residue was dissolved in dichloromethane, and the copper catalyst was removed by a magnet. The remaining solution was filtered, the solvent was removed by rotating distillation under reduced pressure, and silica gel column chromatography using ethyl acetate/hexane was performed to obtain Compound 46 as a solid product.

$^1$H NMR: δ (ppm)=8.39 (s, 1H), 8.08 (s, 1H), 8.00 (s, 1H), 7.95 (d, 1H), 7.88 (d, 1H), 7.68 (d, 1H), 7.64 (d, 1H), 7.44 (d, 1H), 7.31 (d, 1H), 7.18 (t, 1H), 7.05 (t, 1H), 7.04 (t, 1H), 7.01 (t, 4H), 6.98 (d, 1H), 6.88 (t, 1H), 6.79 (d, 1H), 6.67 (d, 2H), 6.62 (t, 2H), 6.46 (d, 4H), 6.42 (d, 2H), 5.00 (br, 3H).

[Example 8] Preparation of Compound 47

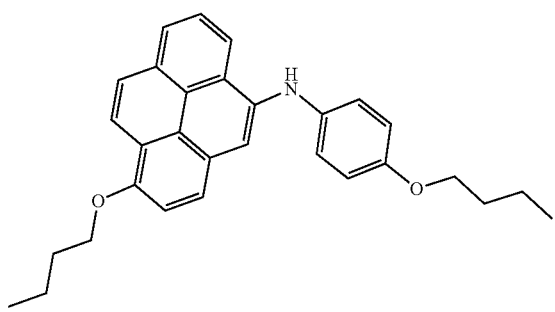 [SMILES: CCCCOc1ccc(Nc2cc3ccc(OCCCC)c4ccc5cccc2c5c34)cc1]

(4-Bromopyren-8-yl)methanol (10 mmol) was dissolved in anhydrous acetone under an argon atmosphere. Thereafter, K$_2$CO$_3$ (20 mmol) was added thereto and stirring was performed for 15 minutes. Thereafter, 1-bromobutane (10 mmol) was added thereto and stirring was performed at room temperature for 4 hours. Thereafter, 5-bromo-1-(butoxymethyl)pyrene (5 mmol), 4-butoxybenzenamine (7.5 mmol), and tBuONa (8 mmol) were added to a reactor under an argon atmosphere, dissolved in anhydrous toluene (100 ml), and stirred. Thereafter, Pd(OAc)$_2$ (0.07 g, 0.5 mmol) and P(tBu)$_3$HBF$_4$ (260 mg, 1 mmol) were added to the reactor and the mixture was reacted at 110° C. for 24 hours. Thereafter, the reactor was cooled down to room temperature, dichloromethane was added thereto, filtration was performed, and washing was performed repeatedly with D.I. water and 1 M HCl. Thereafter, the solvent was removed using an evaporator, and column chromatography using PE/DCM was used to obtain Compound 47.

$^1$H NMR: δ (ppm)=8.12-8.01 (m, 2H), 7.88-7.82 (m, 2H), 7.71 (d, 2H), 7.33 (s, 1H), 6.91 (s, 1H), 6.52 (d, 2H), 6.35 (d, 2H), 4.30 (s, 1H), 4.04-3.94 (m, 4H), 1.71 (p, 4H), 1.32 (m, 4H), 0.96 (t, 6H).

[Example 9] Preparation of Compound 48

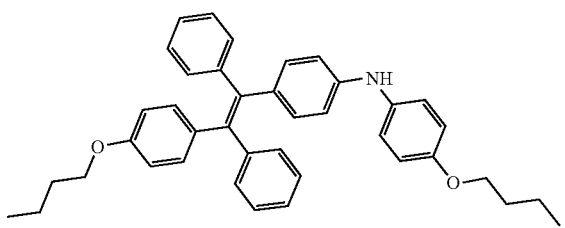 [SMILES: CCCCOc1ccc(Nc2ccc(/C(=C(\c3ccccc3)c3ccc(OCCCC)cc3)c3ccccc3)cc2)cc1]

4-((E)-2-(4-bromophenyl)-1,2-diphenylvinyl)phenol (10 mmol) was dissolved in anhydrous acetone under an argon atmosphere. Thereafter, K$_2$CO$_3$ (20 mmol) was added thereto and stirring was performed for 15 minutes. 1-Bromobutane(10 mmol) was added thereto and stirring was performed at room temperature for 4 hours to obtain 1-((E)-2-(4-bromophenyl)-1,2-diphenylvinyl)-4-butoxybenzene.

The thus-obtained 1-((E)-2-(4-bromophenyl)-1,2-diphenylvinyl)-4-butoxybenzene (5 mmol), 4-butoxybenzenamine (7.5 mmol), and tBuONa(8 mmol) were added to a reactor under an argon atmosphere, anhydrous toluene (100 ml) was dissolved therein, and stirring was performed. Thereafter, Pd(OAc)$_2$ (0.07 g, 0.5 mmol) and P(tBu)$_3$HBF$_4$ (260 mg, 1 mmol) were added to the reactor and the mixture was reacted at 110° C. for 24 hours. Thereafter, the reactor was cooled down to room temperature, dichloromethane was added thereto, filtration was performed, and washing was performed repeatedly with D.I. water and 1 M HCl. The solvent was removed using an evaporator, and column chromatography using PE/DCM was performed to prepare Compound 48.

$^1$H NMR: δ (ppm)=7.42 (d, 4H), 7.31 (d, 2H), 7.26 (t, 4H), 7.17-7.11 (m, 4H), 6.77 (d, 2H), 6.52 (d, 4H), 6.35 (d, 2H), 4.30 (s, 1H), 3.94 (t, 4H), 1.71 (p, 4H), 1.33 (m, 4H), 0.96 (t, 6H).

[Example 10] Preparation of Compound 49

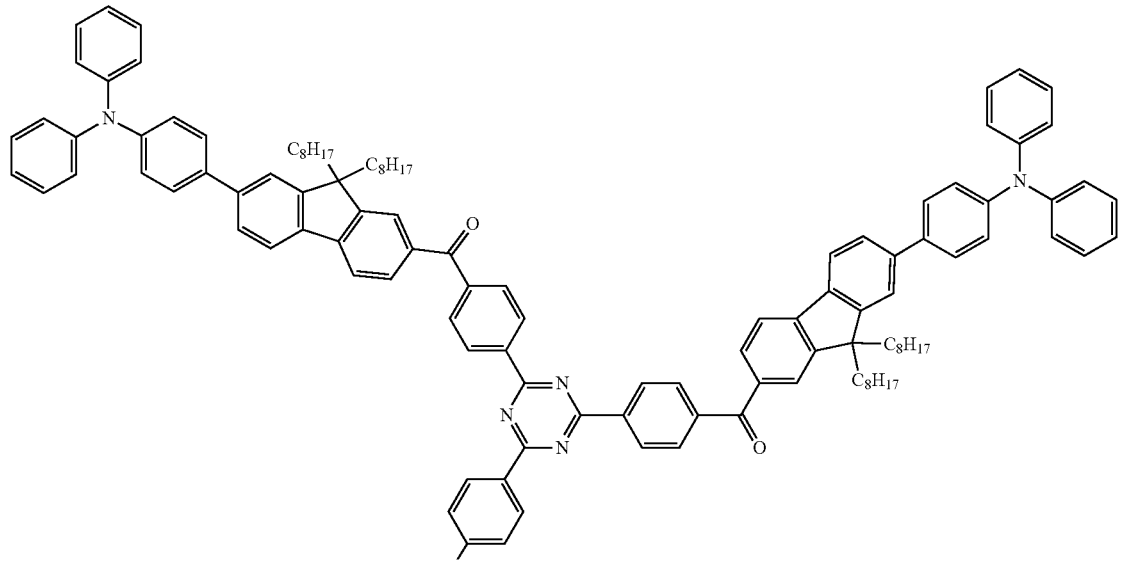

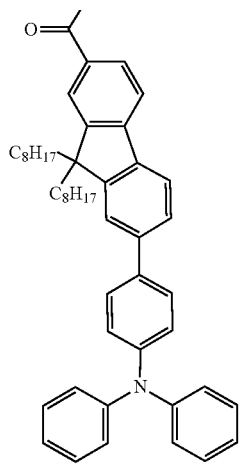

In a flask, trifluoromethanesulfonic acid 6.0 g (40 mmol) was dissolved in 40 ml of anhydrous chloroform. The solution was cooled down to 0° C., 2-bromo-7-(4-cyanophenyl)carbonyl-9,9-dioctyl-9H-fluorene 12.0 g (20 mmol) was dissolved in 120 ml of anhydrous chloroform, and titration was performed. After stirring for 30 minutes, stirring was performed at room temperature for 24 hours. Thereafter, an unreacted acid was neutralized by an ammonia solution, and a precipitate was separated by a filter. The obtained precipitate was washed with ethanol, hexane, and chloroform to obtain a triazine compound. 1.65 g (0.92 mmol) of the triazine compound and 1.37 g (3.68 mmol) of N-(4-(4,4,5,5-tetramethyl-1,3,2-dioxaborolan-2-yl)phenyl)-N-phenylbenzenamine were dissolved in 30 ml of toluene under a nitrogen atmosphere, and 5.5 ml of a $Na_2Co_3$ solution and 32 mg (0.03 mmol) of tetrakis(triphenylphosphine) palladium(0) were added thereto. The reactor was stirred at 90° C. for 36 hours. Thereafter, the reactor was cooled down to a room temperature, and extraction was performed using $CH_2Cl_2$ and distilled water. Moisture was removed by anhydrous $Na_2SO_4$, and Compound 49 was obtained by a solid-liquid extraction method.

$^1$H NMR: δ (ppm)=7.99-7.90 (m, 9H), 7.82-7.76 (m, 12H), 7.60-7.58 (m, 9H), 7.23 (d, 6H), 7.01 (t, 12H), 6.62 (t, 6H), 6.52 (d, 6H), 6.46 (d, 12H), 1.87 (t, 12H), 1.33-1.29 (m, 72H), 0.96 (t, 18H).

[Example 11] Preparation of Compounds 50 and 51

Compounds 50 and 51 were prepared with different starting materials and solvents from those of the method of Example 1.

Compound 50

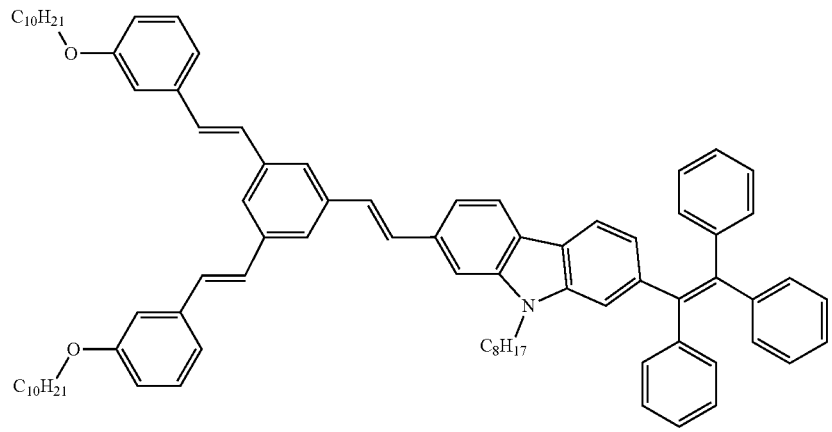

¹H NMR: δ (ppm)=7.56-7.55 (m, 3H), 7.43-7.42 (m, 9H), 7.33 (m, 3H), 7.26 (t, 6H), 7.17-7.11 (m, 7H), 6.99-6.93 (m, 10H), 6.62 (d, 2H), 3.94-3.85 (m, 6H), 1.77-1.71 (m, 6H), 1.33-1.29 (m, 38H), 0.96 (t, 9H).

Compound 51

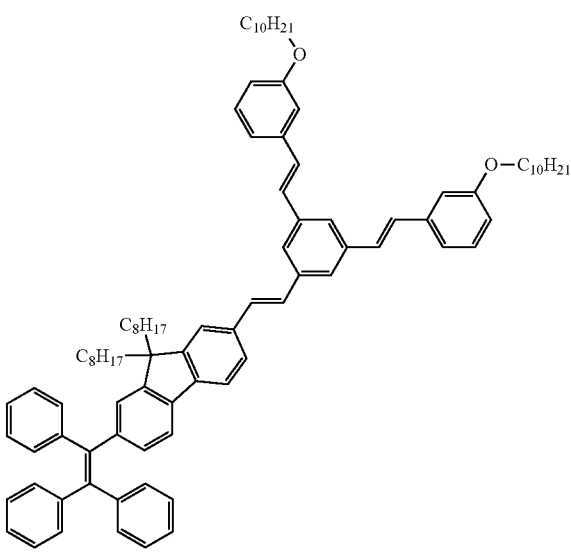

¹H NMR: δ (ppm)=7.84 (d, 3H), 7.71 (s, 2H), 7.54 (d, 2H), 7.43-7.42 (m, 9H), 7.26 (t, 6H), 7.15-7.11 (m, 5H), 6.99-6.93 (m, 10H), 6.62 (d, 2H), 3.94 (t, 6H), 1.87 (t, 4H), 1.71 (p, 4H), 1.33-1.29 (m, 52H), 0.96 (t, 12H).

[Example 12] Manufacture of Organic Electronic Element

ITO was washed using a washer for an optical cell and ethanol for 1 hour. Thereafter, the surface was made hydrophobic by 02 plasma, and was placed on a vacuum chamber with tichloro(1H, 1H, 2H, 2H-perfluoro-octyl)silane to perform surface treatment. To a solution in which dimethylacetamide and acetone were mixed at a mass ratio of 1:1, the compounds of the Examples of the present invention described in the following Table 4 were added to prepare solutions. Coating was performed using a spin coater for 1 minute at 1500 rpm with an acceleration time of 3 seconds to obtain a ferroelectric fluorescent self-assembly compound layer of 100 nm. Thereafter, gold was deposited on the ferroelectric fluorescent self-assembly compound layer to manufacture an organic electronic element. The results of measuring the polarization property and the light-emitting property of the thus-manufactured organic electronic element are shown in the following Table 4.

A P-E curve using Compound 1 of the present invention was determined, and is shown in FIG. 1.

An electric field of 0.1 to 500 kV/cm was applied to the specifically manufactured electronic elements of Examples 11 and 13 at room temperature for 10 to 20 minutes to derive a polarization hysteresis curve, and the presence of piezoelectricity and a remanent polarization property (Pr) were calculated from the derived hysteresis curve.

TABLE 4

| Compound of the present invention | Experiment method | Additive (wt % relative to ferroelectric light-emitting compound) | Temperature (° C.)/drying time (h) | Pr(mC/m²) | Light-emitting maximum wavelength (nm) |
|---|---|---|---|---|---|
| Compound 1 | Example 12 | — | 80/1 h | 5 | 480 |
| Compound 3 | Example 12 | — | 100/1 h | 8 | 477 |
| Compound 7 | Example 12 | — | 120/2 h | 1 | 440 |
| Compound 19 | Example 12 | — | 100/1 h | 4 | 387 |
| Compound 28 | Example 12 | — | 70/1 h | 20 | 408 |
| Compound 30 | Example 12 | — | 60/1 h | 20 | 446 |
| Compound 35 | Example 12 | — | 80/1 h | 25 | 450 |
| Compound 44 | Example 12 | — | 80/1 h | 20 | 430 |
| Compound 43 | Example 12 | — | 90/1 h | 30 | 474 |

TABLE 4-continued

| Compound of the present invention | Experiment method | Additive (wt % relative to ferroelectric light-emitting compound) | Temperature (° C.)/drying time (h) | $Pr(mC/m^2)$ | Light-emitting maximum wavelength (nm) |
|---|---|---|---|---|---|
| Compound 1 | Example 14 | PVDF-TrFE (5) CBP (20) THABF4 (5) | 135/1.5 h | 10 | 472 |
| Compound 1 | Example 14 | PVK (15), CBP (20) THABF$_4$ (5) | 120/1 h | 2 | 485 |
| Compound 3 | Example 14 | PVDF-TrFE (5) CBP (20) THABF$_4$ (5) | 130/1.5 h | 12 | 470 |
| Compound 7 | Example 14 | PVK (15), CBP (20) THABF$_4$ (5) | 100/2 h | 0.8 | 475 |
| Compound 14 | Example 14 | PVK (15), CBP (20) THABF$_4$ (5) | 70/1 h | 0.3 | 446 |
| Compound 19 | Example 14 | PVK (15), CBP (20) THABF$_4$ (5) | 100/1 h | 3 | 388 |
| Compound 40 | Example 14 | PVK (15), CBP (20) THABF$_4$ (5) | 80/1 h | 5 | 449 |

As shown in Table 4, it was found that the ferroelectric fluorescent self-assembly compound of the present invention shows ferroelectricity and also has excellent light-emitting property.

[Example 13] Manufacture of Organic Electronic Element

Patterned ITO was washed using a washer for an optical cell and ethanol for 1 hour. Thereafter, the surface was made hydrophobic by 02 plasma, and was placed on a vacuum chamber with tichloro(1H, 1H, 2H, 2H-perfluoro-octyl) silane to perform surface treatment. 3 g of poly(vinylidene fluoride-co-hexafluoropropylene) (PVDF-HFP) and 2.28 g of the compound of Example 1 (Compound 1) of the present invention were added to a mixed solvent in which dimethylacetamide and acetone were mixed at a mass ratio of 1:1 to prepare a ferroelectric fluorescent self-assembly compound solution. Spin coating was performed using a spin coater at 1800 rpm for 30 seconds with an acceleration time of 3 seconds to prepare a ferroelectric fluorescent self-assembly compound layer of 35 Thereafter, an Au electrode of 100 nm was deposited on the ferroelectric fluorescent self-assembly compound layer to manufacture an organic electronic element. A Ps value of the thus-manufactured tautomer light-emitting element was 3 mC/m$^2$, and the light-emitting property measured by a fluorescence measurement device is shown in FIG. 1, and a maximum light emission wavelength was shown at 475 nm.

[Example 14] Manufacture of Organic Electronic Element

In Example 13, an organic electronic element including a first electrode, a second electrode opposite to the first electrode, and an organic layer interposed between the first electrode and the second electrode was manufactured, in which the organic layer included the compound of the Example of the present invention described in Table 4 or an ionic compound thereof; a CBP host material and a tetraethylammonium tetrafluoroborate (THABF$_4$) electrolyte and the thickness of the organic layer was 100 nm, and the organic layer and the electrodes were included in the organic electronic element. A blue green electroluminescence was shown at an applied voltage of 6 V or more.

The results of measuring the polarization property and the light-emitting property of the thus-manufactured organic electronic element are shown in the above Table 4.

The ferroelectric fluorescent self-assembly compound of the present invention has ferroelectricity by introducing a specific skeleton and a specific functional group to induce self-assembly and does not have a deteriorated light-emitting property by using an aggregation-induced emission enhancement (AIEE).

The ferroelectric fluorescent self-assembly compound of the present invention has maximized polarization by molecular arrangement to have excellent ferroelectricity and piezoelectricity and an improved light-emitting property.

An organic electronic element including the ferroelectric fluorescent self-assembly compound of the present invention and an electronic device including the organic electronic element have an excellent light-emitting property and the light-emitting property may be easily controlled.

As described above, though the exemplary embodiments of the present invention have been described in detail, a person skilled in the art may make various variations of the present invention without departing from the spirit and the scope of the present invention, as defined in the claims which follow. Accordingly, any modification of the following Examples of the present invention may not depart from the technique of the present invention.

What is claimed is:

1. A ferroelectric fluorescent self-assembly compound which is represented by the following Chemical Formulae 13:

[Chemical Formula 13]

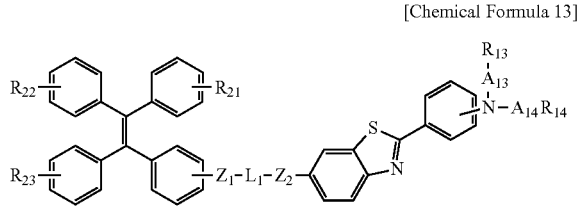

wherein
$Z_1$ to $Z_4$ are independently of one another a single bond, —O—, —OCO—, —COO—, —NH—, —CONH—, —NHCO—, or C2-C6 alkenylene;
$L_1$ and $L_2$ are independently of each other a single bond, C1-C10 alkylene, C2-C10 alkenylene, or C6-C12 arylene;
$A_{13}$ and $A_{14}$ are independently of each other C6-C30 arylene;
$R_{13}$ and $R_{14}$ are independently of each other hydrogen, a halogen, C4-C25 alkoxy, CHO, or NHCOOH; and
$R_{21}$ to $R_{23}$ are independently of one another hydrogen, a halogen, C1-C30 alkoxy, or

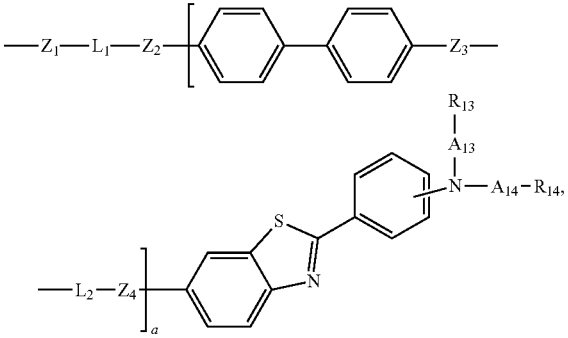

in which a is an integer of 0 or 1.

2. A ferroelectric fluorescent self-assembly compound which is represented by the following Chemical Formula 14:

[Chemical Formula 14]

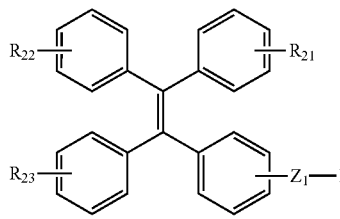 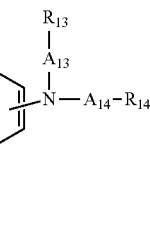

wherein
$Z_1$ to $Z_4$ are independently of one another a single bond, —O—, —OCO—, —COO—, —NH—, —CONH—, —NHCO—, or C2-C6 alkenylene;
$L_1$ and $L_2$ are independently of each other a single bond, C1-C10 alkylene, C2-C10 alkenylene, or C6-C12 arylene;
$A_{13}$ and $A_{14}$ are independently of each other C6-C30 arylene;
$R_{13}$ and $R_{14}$ are independently of each other hydrogen, a halogen, C4-C25 alkoxy, CHO, or NHCOOH; and
$R_{21}$ to $R_{23}$ are independently of one another hydrogen, a halogen, C1-C30 alkoxy, or

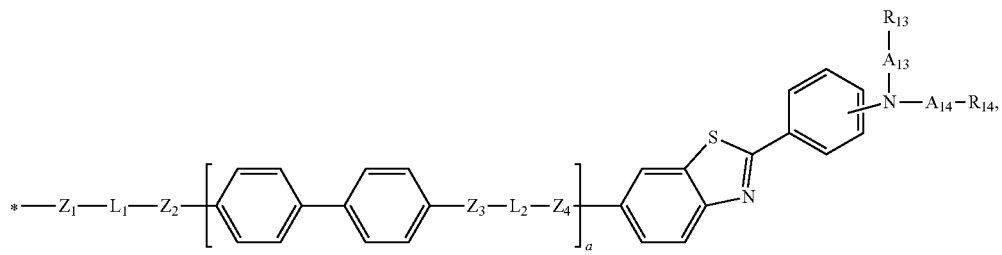

in which a is an integer of 0 or 1.

3. The ferroelectric fluorescent self-assembly compound of claim 2, wherein in Chemical Formula 14, $Z_1$ to $Z_4$ are independently of one another a single bond, —O—, or —OCO—;

$L_1$ and $L_2$ are independently of each other a single bond or C2-C10 alkenylene;

$A_{13}$ and $A_{14}$ are independently of each other C6-C12 arylene;

$R_{13}$ and $R_{14}$ are independently of each other hydrogen, a halogen, CHO, or NHCOOH; and $R_{21}$ to $R_{23}$ are independently of one another hydrogen, C4-C25 alkoxy, or

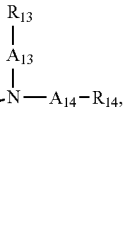

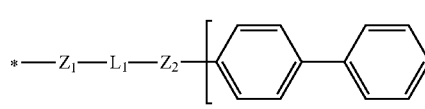

in which a is an integer of 0 or 1.

4. The ferroelectric fluorescent self-assembly compound of claim 1, wherein the ferroelectric fluorescent self-assembly compound is selected from the following compounds:

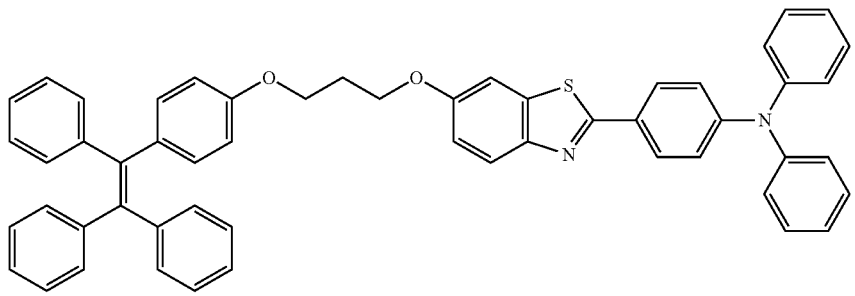

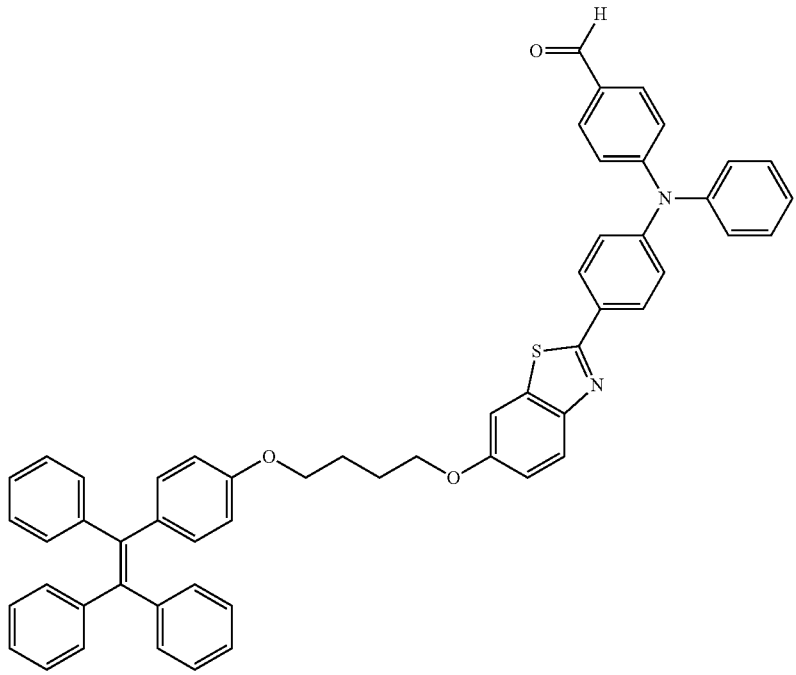

193

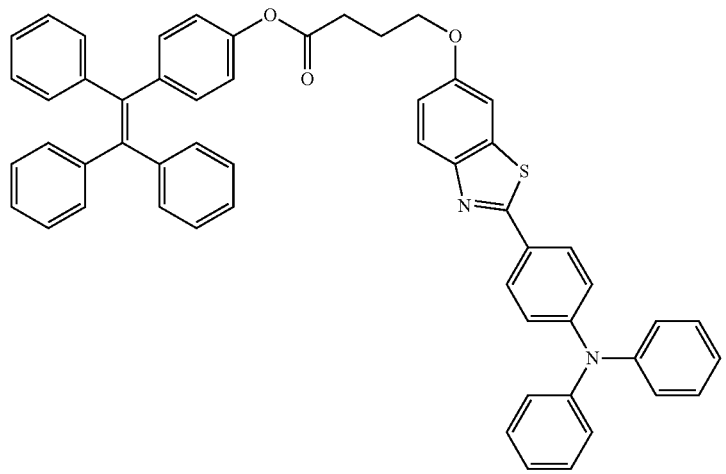

-continued

194

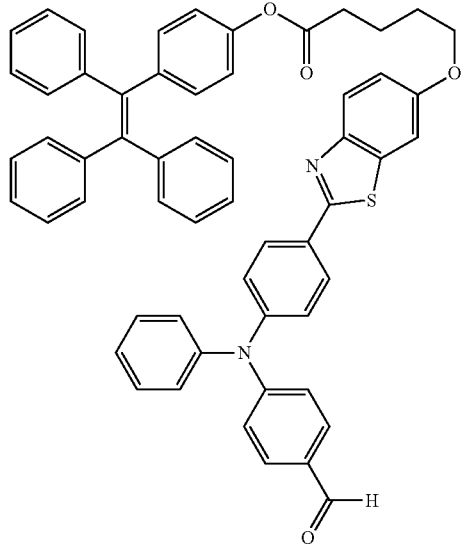

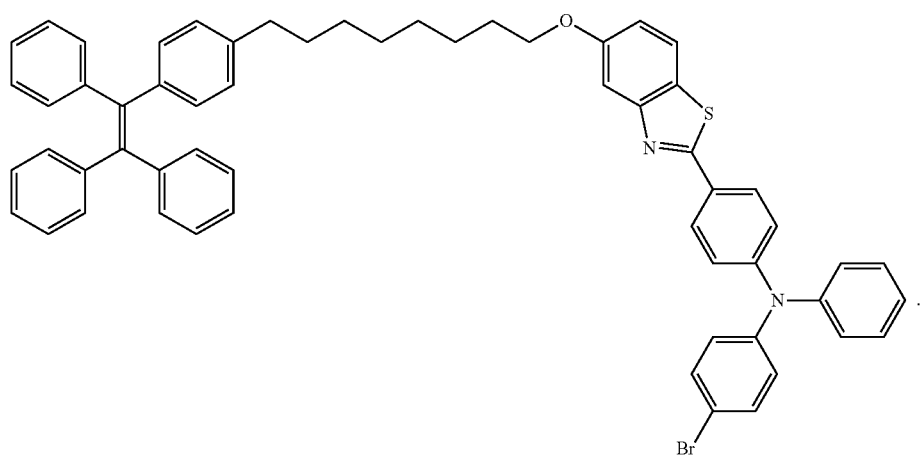

5. An organic electronic element comprising the ferroelectric fluorescent self-assembly compound of claim 1.

6. The organic electronic element of claim 5, wherein the organic electronic element is an organic light-emitting element, an organic solar cell, an organic thin film transistor, an organic electroluminescence element, an organic sensor, or a capacitor.

7. The organic electronic element of claim 5, wherein the ferroelectric fluorescent self-assembly compound is included in an organic layer of the organic electronic element.

8. An electronic device comprising the organic electronic element of claim 5.

9. The ferroelectric fluorescent self-assembly compound of claim 1, wherein in Chemical Formula 13,
$Z_1$ to $Z_4$ are independently of one another a single bond, —O—, or —OCO—;
$L_1$ and $L_2$ are independently of each other a single bond or C2-C10 alkenylene;
$A_{13}$ and $A_{14}$ are independently of each other C6-C12 arylene;

$R_{13}$ and $R_{14}$ are independently of each other hydrogen, a halogen, CHO, or NHCOOH; and $R_{21}$ to $R_{23}$ are independently of one another hydrogen, C4-C25 alkoxy, or

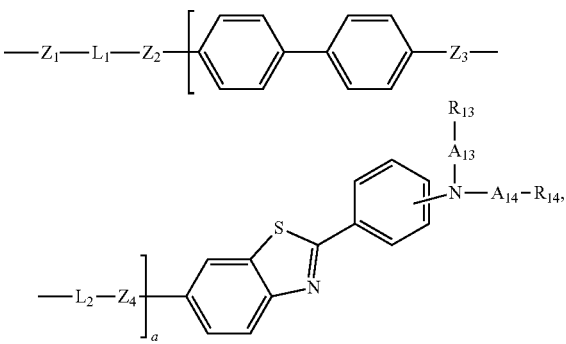

in which a is an integer of 0 or 1.

10. The ferroelectric fluorescent self-assembly compound of claim 2, wherein the ferroelectric fluorescent self-assembly compound is:
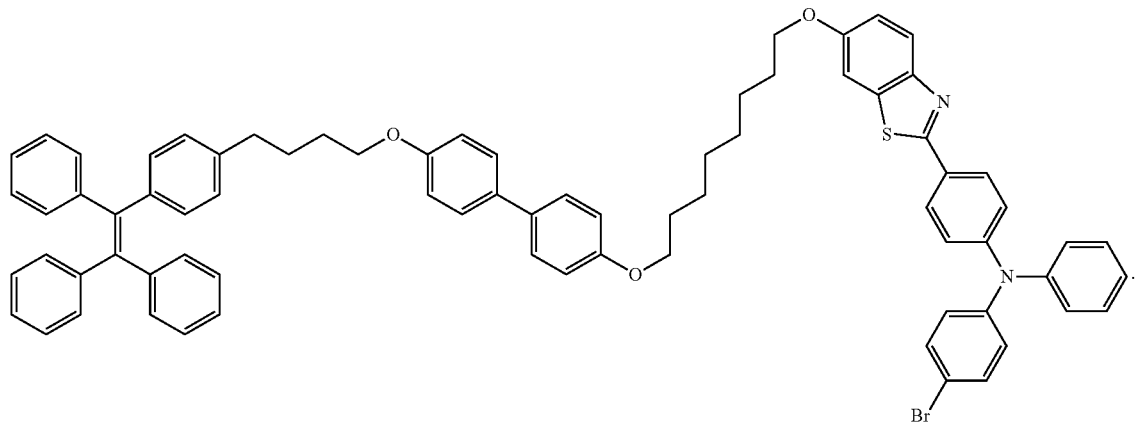 [SMILES: Brc1ccc(N(c2ccccc2)c2ccc(-c3nc4ccc(OCCCCCCCCOc5ccc(-c6ccc(OCCCCc7ccc(C(=C(c8ccccc8)c8ccccc8)c8ccccc8)cc7)cc6)cc5)cc4s3)cc2)cc1]
11. A ferroelectric fluorescent self-assembly compound, wherein the ferroelectric fluorescent self-assembly compound is:
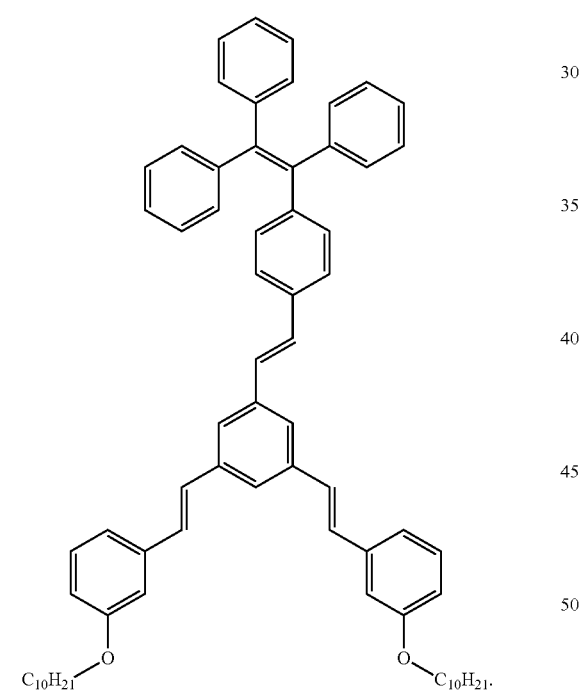
* * * * *